(12) United States Patent
Jodele et al.

(10) Patent No.: US 11,840,564 B2
(45) Date of Patent: Dec. 12, 2023

(54) DOSING ALGORITHM FOR COMPLEMENT INHIBITOR

(71) Applicant: Children's Hospital Medical Center, Cincinnati, OH (US)

(72) Inventors: Sonata Jodele, Montgomery, OH (US); Tsuyoshi Fukuda, Cincinnati, OH (US); Kana Mizuno, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 1129 days.

(21) Appl. No.: 15/580,053

(22) PCT Filed: May 27, 2016

(86) PCT No.: PCT/US2016/034547
§ 371 (c)(1),
(2) Date: Dec. 6, 2017

(87) PCT Pub. No.: WO2016/200627
PCT Pub. Date: Dec. 15, 2016

(65) Prior Publication Data
US 2019/0202899 A1    Jul. 4, 2019

Related U.S. Application Data

(60) Provisional application No. 62/172,987, filed on Jun. 9, 2015.

(51) Int. Cl.
| | | |
|---|---|---|
| C07K 16/18 | (2006.01) | |
| G16H 20/17 | (2018.01) | |
| G01N 33/68 | (2006.01) | |
| A61K 39/00 | (2006.01) | |
| A61P 9/10 | (2006.01) | |
| A61P 37/02 | (2006.01) | |

(52) U.S. Cl.
CPC ............ C07K 16/18 (2013.01); A61P 9/10 (2018.01); A61P 37/02 (2018.01); G01N 33/6893 (2013.01); G16H 20/17 (2018.01); A61K 2039/505 (2013.01); A61K 2039/545 (2013.01); C07K 2317/24 (2013.01); C07K 2317/76 (2013.01); C07K 2317/94 (2013.01)

(58) Field of Classification Search
CPC .......... A61B 5/72; G01N 33/53; G01N 33/48; G16H 20/10; G16H 10/40; G16C 20/30
See application file for complete search history.

(56) References Cited

U.S. PATENT DOCUMENTS

| | | | |
|---|---|---|---|
| 6,355,245 B1 | 3/2002 | Evans et al. | |
| 7,700,098 B2 | 4/2010 | Ferlin et al. | |
| 8,999,340 B2 | 4/2015 | Margo | |
| 9,447,176 B2 | 9/2016 | Rother et al. | |
| 9,494,601 B2 | 11/2016 | McKnight et al. | |
| 2006/0234285 A1 | 10/2006 | Gentz et al. | |
| 2007/0116710 A1 | 5/2007 | Bell et al. | |
| 2009/0269356 A1 | 10/2009 | Epstein et al. | |
| 2011/0212900 A1 | 9/2011 | Ikezoe et al. | |
| 2012/0237515 A1 | 9/2012 | Bell et al. | |
| 2014/0371133 A1* | 12/2014 | Francois | A61P 19/00 514/1.7 |
| 2015/0050671 A1 | 2/2015 | Wippermann et al. | |
| 2015/0174243 A1 | 6/2015 | Magro | |
| 2016/0046709 A1 | 2/2016 | Welcher et al. | |
| 2016/0194386 A1 | 7/2016 | Jodele et al. | |
| 2016/0300037 A1* | 10/2016 | Mould | G16H 50/20 |
| 2016/0326244 A1 | 11/2016 | De Min et al. | |
| 2018/0142015 A1 | 5/2018 | de Min et al. | |

FOREIGN PATENT DOCUMENTS

| | | |
|---|---|---|
| WO | WO 2004/034988 A2 | 4/2004 |
| WO | WO 2014/003744 A1 | 1/2014 |
| WO | WO 2015/039126 A1 | 3/2015 |
| WO | WO 2015/070041 A1 | 5/2015 |
| WO | WO 2016/200627 A1 | 12/2016 |

OTHER PUBLICATIONS

Jodele, S. et al; "Eculizumab Therapy in Children with Severe Hematopoietic Stem Cell Transplantation—Associated Thrombotic Microangiopathy", Biology of Blood and Marrow Transplantation, vol. 20, Issue 4, 2014, pp. 518-525 (Year: 2014).*
Dirks NL, Meibohm B. "Population pharmacokinetics of therapeutic monoclonal antibodies". Clin Pharmacokinet Oct. 1, 2010; 49(10):633-59. (Year: 2010).*
Bai, S. et al. A Guide to Rational Dosing of Monoclonal Antibodies. Clin Pharmacokinet 51, 119-135 (2012). (Year: 2012).*
Mehvar R. Estimation of pharmacokinetic parameters based on the patient-adjusted population data. Am J Pharm Educ. 2006;70(5):96 (Year: 2006).*
Mould, D. (2016), "Why therapeutic drug monitoring is needed for monoclonal antibodies and how do we implement this?". Clin. Pharmacol. Ther., 99: 351-354 (Year: 2016).*
Munnink, O. et al; "Therapeutic drug monitoring of monoclonal antibodies in inflammatory and malignant disease—translating TNF-α experience to oncology". Clin. Pharmacol. Ther. (2015) p. 419-431 (Year: 2015).*

(Continued)

*Primary Examiner* — Olivia M. Wise
(74) *Attorney, Agent, or Firm* — Nicole M. Tepe

(57) ABSTRACT

Described are methods and systems for the treatment of individuals having a disorder characterized by complement system dysregulation. The described methods and systems may be used for a variety of purposes, including for example, establishing one or both of a general or personalized dosing schedule for treatment using a complement inhibitor, establishing a dosage schedule sufficient to maintain an effective amount of complement inhibitor, establishing general dosing schedules for novel complement modifying agents and identifying a treatment regimen and/or dose eliminating the possibility of under dosing medication, and treatment regimen and/or dose for reducing or preventing toxicity in a patient.

3 Claims, 22 Drawing Sheets

(56) References Cited

OTHER PUBLICATIONS

Wolff K. (2015) Pharmacokinetics. In: Stolerman I.P., Price L.H. (eds) Encyclopedia of Psychopharmacology. Springer, Berlin, Heidelberg, pp. 1200-1415. (Year: 2015).*
Benet, L. Z. et al; "Basic Principles of Pharmacokinetics", Toxicologic Pathology, vol. 23, No. 2, 1995, pp. 115-123 (Year: 1995).*
Barnett, A. Nicholas R., et al. "The use of eculizumab in renal transplantation." Clinical transplantation 27.3 (2013): E216-E229 (Year: 2013).*
Soliris® (eculizumab) Prescribing information, pp. 1-24, 2011 Revision. (Year: 2011).*
Anderson, B.J., et al., "Tips and traps analyzing pediatric PK data," Pediatric Anesthesia, 2011, 21:222-37, 16 pgs.
Cho, B-S., et al., "Validation of Recently Proposed Consensus Criteria for Thrombotic Microangiopathy After Allogeneic Hematopoietic Stem-Cell Transplantation," Transplantation, 2010, 90:918-26, 9 pgs.
De Fontbrune, F.S., et al., "Use of Eculizumab in Patients with Allogeneic Stem Cell Transplant-Associated Thrombotic Microangiopathy: A Study From the SFGM-TC," Trannsplantation, Sep. 2015, 99(9):1953-9, 7 pgs.
Dietrich, S., et al., "Endothelial Vulnerability and Endothelial Damage are Associated with Risk of Graft-versus-Host Disease and Response to Steroid Treatment," Biol Blood Marrow Transplant, 2013, 19:22-7, 6 pgs.
Feng, S., et al., "Partial ADAMTS13 deficiency in atypical hemolytic uremic syndrome," Blood, 2013, 122:1487-93, 7 pgs.
Jodele, S., et al., "A new paradigm: Diagnosis and management of HSCT-associated thrombotic microangiopathy as a multi-system endothelial injury," Blood Rev., May 2015, 29(3):191-204, 37 pgs.
Jodele, S., et al., "Abnormalities in the alternative pathway of complement in children with hematopoietic stem cell transplant-associated thrombotic microangiopathy," Blood, 2013, 122:2003-7, 5 pgs.
Jodele, S., et al., "Diagnostic and risk criteria for HSCT-associated thrombotic microangiopathy: a study in children and young adults," Blood, 2014, 124:645-53, 9 pgs.
Jodele, S., et al., "Eculizumab Therapy in Children with Severe Hematopoietic Stem Cell Transplantation-Associated Thrombotic Microangiopathy," Biology of Blood and Marrow Transplantation, Journal of the American Society for Blood and Marrow Transplantation, Apr. 2014, 20(4):518-525, 8 pgs.
Jodele, S., et al., "Refined diagnostic and risk criteria for HSCT-associated thrombotic microangiopathy: a prospective study in children and young adults," Blood, Jul. 2014, 124(4):645-653, 9 pgs.
Jodele, S., et al., "The genetic fingerprint of susceptibility for transplant-associated thrombotic microangiopathy," Blood, 2016, 127:989-996, 8 pgs.
Jodele, S., et al., "Variable eculizumab clearance requires pharmacodynamic monitoring to optimize therapy for thrombotic microangiopathy after hematopoietic stem cell transplantation," Biol. Blood Marrow Transplant, Feb. 2016, 22(2):307-315, 29 pgs.
Keating, G.M., "Eculizumab: A Review of Its Use in Atypical Haemolytic Uraemic Syndrome," Drugs, 2013, 73:2053-66, 14 pgs.
Kim, S.S., et al., "Hematopoietic stem cell transplant-associated thrombotic microangiopathy: review of pharmacologic treatment options," Transfusion, 2015, 55:452-8, 7 pgs.
Kojouri, K., et al., "Thrombotic microangiopathy following allogeneic hematopoietic stem cell transplantation," Curr Opin Oncol, 2007, 19:148-54, 7 pgs.
Labrador, J., et al., "Risk factors for thrombotic microangiopathy in allogeneic hematopoietic stem cell recipients receiving GVHD prophylaxis with tacrolimus plus MTX or sirolimus," Bone Marrow Transplant, May 2014, 49(5):684-90, 7 pgs.
Laskin, B.L., et al., "Renal Arteriolar C4d Deposition: A Novel Characteristic of Hematopoietic Stem Cell Transplantation-Associated Thrombotic Microangiopathy," Transplantation, Jul. 2013, 96(2):217-23, 15 pgs.
Legendre, C.M., et al., "Eculizumab in Atypical Hemolytic-Uremic Syndrome," N Engl J Med, 2013, 369:1379-80, 4 pgs.
Legendre, C.M., et al., "Terminal Complement Inhibitor Eculizumab in Atypical Hemplytic-Uremic Syndrome," N Engl J Med, 2013, 368:2169-81, 13 pgs.
Mckeage, K., "Eculizumab: A Review of Its Use in Paroxysmal Nocturnal Haemoglobinuria," Drugs, 2011, 71:2327-45, 19 pgs.
Meri, S., "Complement activation in diseases presenting with thrombotic microangiopathy," European Journal of Internal Medicine, 2013, 24:496-502, 7 pgs.
Nakamae, H., et al., "Risk Factor Analysis for Thrombotic Microangiopathy after Reduced-Intensity or Myeloablative Allogeneic Hematopoietic Stem Cell Transplantation," American Journal of Hematology, 2006, 81:525-31, 7 pgs.
Peffault De Latour, R., et al., "Assessing complement blockade in patients with paroxysmal nocturnal hemoglobinuria receiving eculizumab," Blood, 2015, 125:775-83, 9 pgs.
Pio, R., et al., "Complement inhibition: a promising concept for cancer treatment," Seminars in Immunology, Feb. 2013, 25(1):54-64, 27 pgs.
Prasad, K., et al., "Prevention of bacterial meningitis: An overview of Cochrane systematic reviews," Respiratory Medicine, 2007, 101:2037-43, 7 pgs.
Rachakonda, S.P., et al., "Single-Nucleotide Polymorphisms Within the Thrombomodulin Gene (THBD) Predict Mortality in Patients with Graft-Versus-Host Disease," J Clin Oncol, 2014, 32(30):3421-7, 9 pgs.
Ricklin, D., et al., "Complement in Immune and Inflammatory Disorders: Pathophysiological Mechanisms," J Immunol, 2013, 190:3831-8, 8 pgs.
Rickun, D., et al., "TMA: beware of complements," Blood, 2013, 122:1997-9, 3 pgs.
Schmidtko, J., et al., "Treatment of Atypical Hemolytic Uremic Syndrome and Thrombotic Microangiopathies: A Focus on Eculizumab," Am J Kidney Dis, 2013, 61:289-99, 11 pgs.
Shah, N., et al., "Role of ADAMTS13 in the management of thrombotic microangiopathies including thrombotic thrombocytopenic purpura (TTP)," Br J Haematol, 2013, 163:514-9, 6 pgs.
Shayani, S., et al., "Thrombotic Microangiopathy Associated with Sirolimus Level after Allogeneic Hematopoietic Cell Transplantation with Tacrolimus/Sirolimus-Based Graft-Versus-Host Disease Prophylaxis," Biol Blood Marrow Transplant, 2013, 19:298-304, 7 pgs.
Uderzo, C., et al., "Risk Factors and Severe Outcome in Thrombotic Microangiopathy After Allogeneic Hematopoietic Stem Cell Transplantation," Transplantation, 2006, 82:638-44, 7 pgs.
Van Den Born, B-J., et al., "Association Between Thrombotic Microangiopathy and Reduced ADAMTS13 Activity in Malignant Hypertension," Hypertension, 2008, 51:862-6, 15 pgs.
Willems, E., et al., "Comparison of thrombotic microangiopathy after allogeneic hematopoietic cell transplantation with high-dose or nonmyeloablative conditioning," Bone Marrow Transplant, 2010, 45:689-93, 5 pgs.
Youden W.J., Ph.D. "Index for Rating Diagnostic Tests," Cancer, 1950, 3:32-5, 4 pgs.
Zheng, S., et al., "Model-Based Assessment of Dosing Strategies in Children for Monoclonal Antibodies Exhibiting Target-Mediated Drug Disposition," CPT: Pharmacometrics & Systems Pharmacology, 2014, 3:e138, 10 pgs.
International Search Report and Written Opinion dated Sep. 9, 2016 for Application No. PCT/US2016/034547, 12 pgs.
U.S. Appl. No. 62/172,987, filed Jun. 9, 2015.
Allinovi, M., et al., "Thrombotic microangiopathy induced by interferon beta in patients with multiple sclerosis: three cases treated with eculizumab," Clin Kidney J, 2017, 10(5):625-631, 7 pgs.
Baghbanian, S.M., et al., "Thrombotic microangiopathy associated with interferon-beta treatment in patients with multiple sclerosis," Iran J Neurol, 2018, 17(2):89-90, 2 pgs.
Baker, K. F., et al., "Novel therapies for immune-mediated inflammatory diseases: What can we learn from their use in rheumatoid arthritis, spondyloathritis, systemic lupus erythematosus, psoriasis, Crohn's disease and ulcerative colitis?" Ann Rheum Dis, Feb. 2018, 77(2):175-187, 13 pgs.

(56) References Cited

OTHER PUBLICATIONS

Billiau, A., "Interferon-γ: Biology and Role in Pathogenesis," Adv Immunol, 1996, 62:61-130, 70 pgs.
Bracaglia, C., et al. "Elevated circulating levels of interferon-γ and interferon-γ-induced chemokines characterize patients with macrophage activation syndrome complicating systemic juvenile idiopathic arthritis," Ann Rheum Dis, 2017, 76:166-172, 7 pgs.
Chen, J., et al., "Genome-Wide Signatures of Transcription Factor Activity: Connecting Transcription Factors, Disease, and Small Molecules," PLoS Comput Biol, 2013; 9(9):e1003198, 12 pgs.
Diamedix, EZ Complement Cells—CH50 Test, for In Vitro Diagnostic Use, Product Information Sheet, dated Jan. 1, 2014, download Dec. 17, 2018 from http://diamedix.com/wp-contect/uploads/2015/10/PI-EZ-Complement-CH50-789-001Rev6-June15.pdf, 3 pgs.
Essaghir, A., et al., "Transcription factor regulation can be accurately predicted from the presence of target gene signatures in microarray gene expression data," Nucleic Acids Research, 2010, 38(11):e120, 11 pgs.
Furie, R., et al. "Anifrolumab, an Anti-Interferon-α Receptor Monoclonal Antibody, in Moderate-to-Severe Systemic Lupus Erythematosus" Arthritis & Rheumatology, 2017, 69(2):376-386, 11 pgs.
Gloude, N.J., et al., "Endothelial Injury, Neutrophil Extracellular Traps, and Complement Activation in Thrombotic Microangiopathy and GVHD," Abstracts / Biology of Blood and Marrow Transplantation, 2017, 23(3):S232-S233, Abstract 310, 2 pgs.
Gloude, N.J., et al, "Thrombotic Microangiopathy Can Occur Before Transplant in Children with HLH," Abstracts / Biology of Blood and Marrow Transplantation, 2017, 23(3):S233-S234, Abstract 311, 2 pgs.
Horiuchi, T., et al., "Complement-targeted therapy: development of C5- and C5a-targeted inhibition," Inflammation and Regeneration, 2016, 36:11, 5 pgs.
Jia, H., et al., "Endothelial cell functions impaired by interferon in vitro: Insights into the molecular mechanism of thrombotic microangiopathy associated with interferon therapy," Thromb Res, 2018, 163:105-116, 12 pgs.
Kanehisa, M., et al., KEGG: new perspectives on genomes, pathways, diseases and drugs, Nucleic Acids Research, 2017, 45:D353-D361, 9 pgs.
Magro, C.M., et al, "Degos Disease: A C5b-9/Interferon-α—Mediated Endotheliopathy Syndrome" Am J Clin Pathol, 2011, 135:599-610, 12 pgs.
Pachlopnik Schmid, J., et al., "Neutralization of IFNγ defeats haemophagocytosis in LCMV-infected perforin- and Rab27a-deficient mice," EMBO Mol Med, 2009, 1:112-124, 13 pgs.
Riggs, J.M., et al, "Characterisation of anifrolumab, a fully human anti-interferon receptor antagonist antibody for the treatment of systemic lupus erythematosus," Lupus Science & Medicine, 2018, 5:e000261, 11 pgs.
Schoenborn, J.R., et al., "Regulation of Interferon-γ During Innate and Adaptive Immune Responses," Chapter 2, Adv Immunol, 2007, 96:41-101, 61 pgs.
Subramanian, A., et al., "Gene set enrichment analysis: a knowledge-based approach for interpreting genome-wide expression profiles," PNAS, 2005, 102:15545-15550, 6 pgs.
Tokunaga, R., et al, "CXCL9, CXCL10, CXCL11/CXCR3 axis for immune activation—a target for novel cancer therapy," Cancer Treat Rev, 2018, 63:40-47, 19 pgs.
Xu, X-J., et al., "Diagnostic Accuracy of a Specific Cytokine Pattern in Hemophagocytic Lymphohistiocytosis in Children," J Pediatr, 2012, 160:984-990, 8 pgs.
Zhang, S-Y., et al. "Inborn errors of interferon (IFN)-mediated immunity in humans: insights into the respective roles of IFN-α/β, IFN-γ, and IFN-λ in host defense," Immunol Rev, 2008, 226:29-40, 12 pgs.
European Office Action, Summons to attend oral proceedings pursuant to Rule 115(1) EPC, dated Jan. 16, 2019 for Application No. EP 14843902.9, 18 pgs.
European Search Report, Extended, and Written Opinion dated Nov. 12, 2020 for Application No. EP 20164737.7, 11 pgs.

U.S. Appl. No. 16/766,327, filed May 22, 2020, by Jodele, entitled: "Compositions for Interferon Blockade and Methods of Using Same."
U.S. Appl. No. 62/593,401, filed Dec. 1, 2017, by Jodele, entitled: "Interferon pathway blockade to treat endothelial injury and thrombotic microangiopathies."
CH50 Eq, Enzyme Immunoassay Kit; For in-vitro diagnostic use only; Product code: MK095, The Binding Site Group, Ltd., Birmingham, UK, Sep. 21, 2009, pp. 1-3, 6 pgs.
"Importance of measuring blood concentration of drugs: Basic knowledge of TDM (monitoring)," Hiroshima Medical Association, Hiroshima, Japan, May 15, 2011, No. 542, pp. 2-5, 13 pgs.
Japanese Office Action, Notice of Reasons for Refusal, dated Sep. 26, 2019 for Application No. JP 2016-542879, 8 pgs.
Aldoss O, et al., "Pericardial effusion after pediatric hematopoietic cell transplant," Pediatr Transplant, 2013;17:294-9, 6 pgs.
Aljitawios, et al., "Late-onset intestinal perforation in the setting of posttransplantation microangiopathy: a case report," Transplant Proc, 2010; 42:3892-3, 2 pgs.
Arai Y, et al., "Serum neutrophil extracellular trap levels predict thrombotic microangiopathy after allogeneic stem cell transplantation," Biol Blood Marrow Transplant, 2013; 19:1683-9, 7 pgs.
Au W-Y, et al., "Successful treatment of thrombotic microangiopathy after haematopoietic stem cell transplantation with rituximab," Br J Haematol, 2007; 137:475-8, 4 pgs.
Batts Ed, et al., "Diagnosis and treatment of transplantation-associated thrombotic microangiopathy: real progress or are we still waiting?" Bone Marrow Transplant, 2007; 40:709-19, 11 pgs.
Bauer, R.J., et al., "A Survey of Population Analysis Methods and Software for Complex Pharmacokinetic and Pharmacodynamic Models with Examples," The AAPS Journal, 2007, 9(1, Article7):E60-E83, 24 pgs.
Biedermann BC., "Vascular endothelium and graft-versus-host disease," Best Pract Res Clin Haematol, 2008; 21:129-38, 10 pgs.
Brukamp K, et al., "Nephrotic syndrome after hematopoietic cell transplantation: do glomerular lesions represent renal graft-versus-host disease?" Clin J Am Soc Nephrol, 2006; 1:685-94, 10 pgs.
Carella AM, et al., "Rituximab for allo-SCT-associated thrombotic thrombocytopenic purpura," Bone Marrow Transplant, 2008; 41:1063-5, 3 pgs.
Carmona A, et al., "Distinct deleterious effects of cyclosporine and tacrolimus and combined tacrolimus-sirolimus on endothelial cells: protective effect of defibrotide," Biol Blood Marrow Transplant, 2013; 19:1439-45, 7 pgs.
Carreras E, et al., "The role of the endothelium in the short-term complications of hematopoietic SCT" Bone Marrow Transplant, 2011; 46:1495-502, 8 pgs.
Cataland SR, et al., "Biomarkers of the alternative pathway and terminal complement activity at presentation confirms the clinical diagnosis of aHUS and differentiates aHUS from TTP," Blood, Jun 12, 2014; 123(24):3733-8, 7 pgs.
Chalandon Y, et al., "Prevention of veno-occlusive disease with defibrotide after allogeneic stem cell transplantation," Biol Blood Marrow Transplant, 2004; 10:347-54, 8 pgs.
Chang A, et al., "Spectrum of renal pathology in hematopoietic cell transplantation: a series of 20 patients and review of the literature," Clin J Am Soc Nephrol, 2007; 2:1014-23, 10 pgs.
Changsirikulchai S, et al., "Renal thrombotic microangiopathy after hematopoietic cell transplant: role of GVHD in pathogenesis," Clin J Am Soc Nephrol, 2009; 4:345-53, 9 pgs.
Cho BS, et al., "Clinical impact of thrombotic microangiopathy on the outcome of patients with acute graft-versus-host disease after allogeneic hematopoietic stem cell transplantation," Bone Marrow Transplant, 2008; 41:813-20, 8 pgs.
Choi CM, et al., "Thrombotic microangiopathy in haematopoietic stem cell transplantation: diagnosis and treatment," Drugs, 2009; 69:183-98, 17 pgs.
Colvin RB., "Antibody-mediated renal allograft rejection: diagnosis and pathogenesis," J Am Soc Nephrol, 2007; 18:1046-56, 11 pgs.
Cooke KR, et al., "The contribution of endothelial activation and injury to end-organ toxicity following allogeneic hematopoietic stem cell transplantation," Biol Blood Marrow Transplant, 2008; 14:23-32, 10 pgs.

(56) References Cited

OTHER PUBLICATIONS

Corbacioglu S, et al., "Defibrotide for prophylaxis of hepatic veno-occlusive disease in paediatric haemopoietic stem-cell transplantation: an open-label, phase 3, randomised controlled trial," Lancet, 2012; 379:1301-9, 9 pgs.

Crovetto F, et al., "The genetics of the alternative pathway of complement in the pathogenesis of HELLP syndrome," The Journal of Maternal-Fetal & Neonatal Medicine: The Official Journal of the European Association of Perinatal Medicine, the Federation of Asia and Oceania Perinatal Societies, the International Society of Perinatal Obstet, 2012; 25:2322-5, 5 pgs.

Cutler C, et al., "Sirolimus and thrombotic microangiopathy after allogeneic hematopoietic stem cell transplantation," Biol Blood Marrow Transplant, 2005; 11:551-7, 7 pgs.

Dandoy CE, et al., "Pulmonary hypertension after hematopoietic stem cell transplantation," Biol Blood Marrow Transplant, 2013, 19:1546-56, 11 pgs.

Dierickx D, et al., "Thrombotic microangiopathy following intestinal transplantation: a single center experience," Transplant Proc, 2010; 42:79-81, 3 pgs.

Eremina V, et al., "VEGF inhibition and renal thrombotic microangiopathy," N Engl J Med, 2008; 358:1129-36, 12 pgs.

Falkner B, et al., Summary of the fourth report on the Diagnosis, Evaluation, and Treatment of High Blood Pressure in Children and Adolescents, Hypertension, 2004; 44:387-388, 2 pgs.

Fuge R, et al., "The clinical features, risk factors and outcome of thrombotic thrombocytopenic purpura occuring after bone marrow transplantation," Br J Haematol, 2001; 113:58-64, 7 pgs.

Fujino M, et al., "Intestinal thrombotic microangiopathy induced by FK506 in rats," Bone Marrow Transplant, 2007; 39:367-72, 6 pgs.

Galie N, et al., "Guidelines for the Diagnosis and Treatment of Pulmonary Hypertension: The Task Force for the Diagnosis and Treatment of Pulmonary Hypertension of the European Society of Cardiology (ESC) and the European Respiratory Society (ERS), endorsed by the International Society of Heart and Lung Transplantation (ISHLT)," European Heart Journal, 2009: 30:2493-537, 45 pgs.

Gatault, P., et al., "Therapeutic drug monitoring of eculizumab: Rationale for an individualized dosing schedule," mAbs, 2015, 7(6):1205-1211, 7 pgs.

George, J.N., et al., "Thrombotic microangiopathy after allogeneic bone marrow transplantation: a pathologic abnormality associated with diverse clinical syndromes," Bone Marrow Transplantation, Jun. 2004: 33(11):1073-1074, XP055352969, 2 pgs.

George JN, et al., "Thrombotic thrombocytopenic purpura-hemolytic uremic syndrome following allogeneic HPC transplantation: a diagnostic dilemma," Transfusion, 2004; 44:294-304, 11 pgs.

Glezerman IG, et al., "Chronic kidney disease, thrombotic microangiopathy, and hypertension following T cell-depleted hematopoietic stem cell transplantation," Biol Blood Marrow Transplant, 2010; 16:976-84, 9 pgs.

Goodwin JE, et al., "Glucocorticoid-induced hypertension," Pediatr Nephrol, 2012; 27:1059-66, 8 pgs.

Gooley TA, et al., "Reduced mortality after allogeneic hematopoietic-cell transplantation," N Engl J Med, 2010; 363:2091-101, 11 pgs.

Gralwohl, A., et al., "Current trends in hematopoietic stem cell transplantation in Europe" Blood, Oct. 2002, 100(7):2374-2386, 14 pgs.

Haines HL, et al., "Blood, and not urine, BK viral load predicts renal outcome in children with hemorrhagic cystitis following hematopoietic stem cell transplantation," Biol Blood Marrow Transplant, 2011; 17:1512-9, 8 pgs.

Hale GA, et al., "Hemolytic uremic syndrome after bone marrow transplantation: clinical characteristics and outcome in children," Biol Blood Marrow Transplant, 2005; 11:912-20, 9 pgs.

Health Resources and Services Administration, US Department of Health and Human Services, "Transplant Activity Report," Apr. 15, 2017, 3 pgs.

Hewamana S, et al., "Intestinal perforation secondary to haematopoietic stem cell transplant associated thrombotic microangiopathy," Eur J Haematol, 2009; 83:277, 1 pg.

Hingorani S, et al., "Urinary cytokines after HCT: evidence for renal inflammation in the pathogenesis of proteinuria and kidney disease," Bone Marrow Transplant, 2014; 49:403-9, 7 pgs.

Hingorani S., "Chronic kidney disease after liver, cardiac, lung, heart-lung, and hematopoietic stem cell transplant," Pediatr Nephrol, 2008; 23:879-88, 10 pgs.

Hingorani SR, et al., "Albuminuria in hematopoietic cell transplantation patients: prevalence, clinical associations, and impact on survival," Biol Blood Marrow Transplant, 2008; 14:1365-72, 8 pgs.

Ho VT, et al., "Blood and marrow transplant clinical trials network toxicity committee consensus summary: thrombotic microangiopathy after hematopoietic stem cell transplantation," Biol Blood Marrow Transplant, 2005; 11:571-5, 5 pgs.

Hoffmeister PA, et al., "Hypertension in long-term survivors of pediatric hematopoietic cell transplantation," Biol Blood Marrow Transplant, 2010; 16:515-24, 10 pgs.

Holmes LV, et al., "Determining the population frequency of the CFHR3/CFHR1 deletion at 1q32," PloS one, 2013; 8:e60352, 7 pgs.

Houtchens J, et al., "Diagnosis and management of pulmonary arterial hypertension," Pulmonary medicine, 2011; 2011:845-864, 14 pgs.

Imhof BA, Aurrand-Lions M. Angiogenesis and inflammation face off. Nature medicine. 2006;12:171-2, 2 pgs.

Inamoto Y, et al., "Clinicopathological manifestations and treatment of intestinal transplant associated microangiopathy," Bone Marrow Transplant, 2009; 44:43-9, 7 pgs.

Inker LA, et al., "Estimating glomerular filtration rate from serum creatinine and cystatin C," N Engl Med, 2012; 367:20-9, 15 pgs.

Ishikawa Y, et al., "Transplantation-associated thrombotic microangiopathy after steroid pulse therapy for polyserositis related to graft-versus-host disease," Clin Exp Nephrol, 2011; 15:179-183, 5 pgs.

Jodele S, et al., "Does early initiation of therapeutic plasma exchange improve outcome in pediatric stem cell transplant-associated thrombotic microangiopathy?" Transfusion, 2013; 53:661-7, 8 pgs.

Jodele S, et al., "Pulmonary arterial hypertension in pediatric patients with hematopoietic stem cell transplant-associated thrombotic microangiopathy," Biol Blood Marrow Transplant, 2013; 19:202-7, 6 pgs.

Jodele S, et al., "Successful early intervention for hyperacute transplant-associated thrombotic microangiopathy following pediatric hematopoietic stem cell transplantation," Pediatr Transplant, 2012; 16:E39-42, 4 pgs.

Keir L, et al., "Advances in our understanding of the pathogenesis of glomerular thrombotic microangiopathy," Pediatr Nephrol, 2011; 26:523-33, 11 pgs.

Kersting S, et al., "Acute renal failure after allogeneic myeloablative stem cell transplantation: retrospective analysis of incidence, risk factors and survival," Bone Marrow Transplant, 2007; 39:359-65, 7 pgs.

Kielstein JT, et al., "Best supportive care and therapeutic plasma exchange with or without eculizumab in Shiga-toxin-producing E. coli O104:H4 induced haemolytic-uraemic syndrome: an analysis of the German STEC-HUS registry," Nephrol Dial Transplant, 2012; 27:3807-15, 9 pgs.

Kurniati NF, et al., "Pleiotropic effects of angiopoietin-2 deficiency do not protect mice against endotoxin-induced acute kidney injury," Nephrol Dial Transplant, 2013; 28:567-75, 9 pgs.

Lapeyraque AL, et al., "Eculizumab in severe Shiga-toxin-associated HUS," N Engl J Med, 2011; 364:2561-3, 3 pgs.

Laskin BL, et al., "Cystatin C-estimated glomerular filtration rate in pediatric autologous hematopoietic stem cell transplantation," Biol Blood Marrow Transplant, 2012; 18:1745-52 8 pgs.

Laskin BL, et al., "Early clinical indicators of transplant-associated thrombotic microangiopathy in pediatric neuroblastoma patients undergoing auto-SCT," Bone Marrow Transplant, 2011; 46:682-9, 8 pgs.

Laskin BL, et al., "Small vessels, big trouble in the kidneys and beyond: hematopoietic stem cell transplantation-associated thrombotic microangiopathy," Blood. 2011; 118:1452-62, 12 pgs.

(56) References Cited

OTHER PUBLICATIONS

Lerner D, et al., "Pericardial effusion in pediatric SCT recipients with thrombotic microangiopathy," Bone Marrow Transplant, Jun. 2014; 49(6):862-3, 2 pgs.

Licht C, et al., "Successful plasma therapy for atypical hemolytic uremic syndrome caused by factor H deficiency owing to a novel mutation in the complement cofactor protein domain 15," Am J Kidney Dis 2005; 45:415-21, 7 pgs.

Lopes Da Silva R, et al., "BK virus encephalitis with thrombotic microangiopathy in an allogeneic hematopoietic stem cell transplant recipient," Transpl Infect Dis. 2011;13:161-7, 8 pgs.

Lovric S, et al., "Removal of elevated circulating angiopoietin-2 by plasma exchange—a pilot study in critically ill patients with thrombotic microangiopathy and anti-glomerular basement membrane disease," Thrombosis and Haemostasis, 2010; 104:1038-43, 6 pgs.

Marr H, et al., "Successful treatment of transplant-associated microangiopathy with rituximab," N Z Med J, 2009; 122:72-4, 3 pgs.

Martinez MT, et al., "Transplant-associated microangiopathy (TAM) in recipients of allogeneic hematopoietic stem cell transplants," Bone Marrow Transplant, 2005; 36:993-1000, 8 pgs.

Menne J, et al., "Validation of treatment strategies for enterohaemorrhagic *Escherichia coli* O104:H4 induced haemolytic uraemic syndrome: case-control study," BMJ, 2012; 345:e4565, 13 pgs.

Mii A, et al. "Renal thrombotic microangiopathy associated with chronic humoral graft versus host disease after hematopoietic stem cell transplantation," Pathol Int, 2011; 61:34-41, 8 pgs.

Mii A, et al., "Renal thrombotic microangiopathy associated with chronic graft-versus-host disease after allogeneic hematopoietic stem cell transplantation," Pathol Int, 2011; 61:518-27, 10 pgs.

Milan A, et al., "Echocardiographic indexes for the non-invasive evaluation of pulmonary hemodynamics," Journal of the American Society of Echocardiography: Official Publication of the American Society of Echocardiography, 2010; 23:225-39; quiz 332-4, 15 pgs.

Mohammed J, et al., "Cardiac tamponade in diarrhoea-positive haemolytic uraemic syndrome," Nephrol Dial Transplant, 2009; 24:679-81, 3 pgs.

Moulder JE, et al., "Captopril and losartan for mitigation of renal injury caused by single-dose total-body irradiation," Radiation Research, 2011; 175:29-36, 8 pgs.

Nadasdy T., "Thrombotic microangiopathy in renal allografts: the diagnostic challenge," Current opinion in organ transplantation, 2014; 19(3);283-292, 10 pgs.

Naina IW, et al., "Thrombotic microangiopathy during peripheral blood stem cell mobilization," J Clin Apher, 2009; 24:259-61, 3 pgs.

Nakamura Y, et al., "Nephrotic syndrome associated with thrombotic microangiopathy following allogeneic stem-cell transplantation for myelodysplastic syndrome," Br J Haematol, 2007; 136:857-9; author reply 9-60, 3 pgs.

Narimatsu H, et al., "Intestinal thrombotic microangiopathy following reduced-intensity umbilical cord blood transplantation," Bone Marrow Transplant, 2005; 36:517-23, 7 pgs.

Nehus EJ, et al., "Performance of cystatin C-based equations in a pediatric cohort at high risk of kidney injury," Pediatr Nephrol, 2013; 28:453-461, 9 pgs.

Nishida T, et al., "Intestinal thrombotic microangiopathy after allogeneic bone marrow transplantation: A clinical imitator of acute enteric graft-versus-host disease," Bone Marrow Transplant, 2004; 33:1143-50, 8 pgs.

Noris M, et al., "Atypical hemolytic-uremic syndrome," N Engl J Med, 2009; 361:1676-87, 12 pgs.

Noris M, et al., "STEC-HUS, atypical HUS and TTP are all diseases of complement activation," Nature reviews Nephrology, 2012; 8:622-33, 12 pgs.

Norkin M, et al., "Large pericardial effusion as a complication in adults undergoing SCT," Bone Marrow Transplant, 2011; 46:1353-6, 4 pgs.

O'Donnell PH, et al., "BK virus infection is associated with hematuria and renal impairment in recipients of allogeneic hematopoetic stem cell transplants," Biol Blood Marrow Transplant, 2009; 15:1038-48 e1, 12 pgs.

Orth D, et al., "Shiga toxin activates complement and binds factor H: evidence for an active role of complement in hemolytic uremic syndrome," J Immunol, 2009; 182:6394-400, 7 pgs.

Parikh CR, et al., "Acute renal failure independently predicts mortality after myeloablative allogeneic hematopoietic cell transplant," Kidney Int, 2005; 67:1999-2005, 8 pgs.

Passweg, J.R., et al., "Hematopoietic stem cell transplantation in Europe 2014: more than 40,000 transplants annually," Bone Marrow Transplantation, 2016, 51:786-792, 7 pgs.

Peffault De Latour, et al., "Successful use of eculizumab in a patient with post-transplant thrombotic microangiopathy," Br J Haematol, Jan. 7, 2013; 161:279-298, 2 pgs.

Perkowska-Ptasinska A, et al., "Thrombotic nephropathy and pulmonary hypertension following autologous bone marrow transplantation in a patient with acute lymphoblastic leukemia: case report," Transplant Proc, 2006; 38:295-6, 2 pgs.

Peyvandi F, et al., "Prospective study on the behaviour of the metalloprotease ADAMTS13 and of von Willebrand factor after bone marrow transplantation," Br J Haematol, 2006; 134:187-95 9 pgs.

Piscitelli D, et al., "Unusual case report of thrombotic microangiopathy of the small bowel following liver transplantation, a possible immunosuppressant-induced disease with histological and ultrastructural findings," TheScientificWorldJournal. 2009; 9:1031-4, 5 pgs.

Platzbecker U, et al., "Graft-versus-host disease prophylaxis with everolimus and tacrolimus is associated with a high incidence of sinusoidal obstruction syndrome and microangiopathy: results of the EVTAC trial," Biol Blood Marrow Transplant, 2009; 15:101-8, 8 pgs.

Rabinovitch M., "Molecular pathogenesis of pulmonary arterial hypertension," The Journal of clinical investigation, 2012; 122:4306-13, 9 pgs.

Rajpal JS, et al., "Improved survival over the last decade in pediatric patients requiring dialysis after hematopoietic cell transplantation," Biol Blood Marrow Transplant, 2013; 19:661-5, 5 pgs.

Reti M, et al., "Complement activation in thrombotic thrombocytopenic purpura," Journal of Thrombosis and Haemostasis: JTH, 2012; 10:791-8, 8 pgs.

Richardson PG, et al., "Defibrotide for the treatment of severe hepatic veno-occlusive disease and multiorgan failure after stem cell transplantation: a multicenter, randomized, dose-finding trial," Biol Blood Marrow Transplant, 2010; 16:1005-17, 13 pgs.

Rodriguez R, et al., "A phase II pilot study of tacrolimus/sirolimus GVHD prophylaxis for sibling donor hematopoietic stem cell transplantation using 3 conditioning regimens," Blood, 2010; 115:1098-105, 9 pgs.

Rosenthal J, et al., "Transplant-associated thrombotic microangiopathy in pediatric patients treated with sirolimus and tacrolimus," Pediatr Blood Cancer, 2011; 57:142-6, 10 pgs.

Roth C, et al., "The posterior reversible encephalopathy syndrome: what's certain, what's new?" Practical Neurology, 2011; 11:136-144, 9 pgs.

Ruutu T, et al., "Diagnostic criteria for hematopoietic stem cell transplant-associated microangiopathy: results of a consensus process by an International Working Group," Haematologica, 2007; 92:95-100, 6 pgs.

Sadeghi B, et al., "Early-phase GVHD gene expression profile in target versus non-target tissues: kidney, a possible target?" Bone Marrow Transplant, 2013; 48:284-93, 10 pgs.

Sagrista-Sauleda J, et al., "Diagnosis and management of pericardial effusion," World Journal of Cardiology, 2011; 3:135-43, 9 pgs.

San T, et al., "Protective effect of defibrotide on perfusion induced endothelial damage," Thrombosis research, 2000; 99:335-41, 7 pgs.

Schroder H., "Defibrotide Protects Endothelial Cells, but not L929 Tumour Cells, from Tumour Necrosis Factor-α-mediated Cytotoxicity," The Journal of Pharmacy and Pharmacology, 1995; 47:250-2, 3 pgs.

(56) References Cited

OTHER PUBLICATIONS

Schwartz GJ, et al., "Glomerular filtration rate measurement and estimation in chronic kidney disease," Pediatr Nephrol, 2007; 22:1839-48, 10 pgs.
Schwimmer J, et al., "De novo thrombotic microangiopathy in renal transplant recipients: a comparison of hemolytic uremic syndrome with localized renal thrombotic microangiopathy," Am J Kidney Dis, 2003; 41:471-9, 9 pgs.
Siami K, et al., "Thrombotic microangiopathy after allogeneic hematopoietic stem cell transplantation: an autopsy study," Transplantation, 2008; 85:22-8, 7 pgs.
Song D, et al., "The spectrum of renal thrombotic microangiopathy in lupus nephritis," Arthritis Research & Therapy, 2013; 15:R12, 12 pgs.
Spector, et al., "Associations of blood lead with estimated glomerular filtration rate using MDRD, CKD-EPI and serum cystatin C-based equations," Nephrol Dial Transplant, Jan. 19, 2011, 26:2786-2792, 8 pgs.
Staykov D, et al., "Posterior Reversible Encephalopathy Syndrome," Journal of Intensive Care Medicine, 2012; 27:11-24, 14 pgs.
Sucak GT, et al., "Treatment of sinusoidal obstruction syndrome with defibrotide: a single-center experience," Transplant Proc, 2007; 39:1558-63, 6 pgs.
Takatsuka H, et al., "Complications after bone marrow transplantation are manifestations of systemic inflammatory response syndrome," Bone Marrow Transplant, 2000; 26:419-26, 9 pgs.
Tati R, et al., "Complement activation associated with ADAMTS13 deficiency in human and murine thrombotic microangiopathy," J Immunol, 2013; 191:2184-93, 11 pgs.
Thurman JM, et al., "Alternative pathway of complement in children with diarrhea-associated hemolytic uremic syndrome," Clin J Am Soc Nephrol, 2009; 4:1920-4, 5 pgs.
Tichelli A, et al., "Vascular endothelium as 'novel' target of graft-versus-host disease," Best Pract Res Clin Haematol, 2008; 21:139-48, 10 pgs.
Totina A, et al., "Atypical hemolytic-uremic syndrome in a child presenting with malignant hypertension," Clinical pediatrics, 2013; 52:183-6, 5 pgs.
Tsai HM., "Untying the knot of thrombotic thrombocytopenic purpura and atypical hemolytic uremic syndrome," Am J Med, 2013; 126:200-9, 10 pgs.
Uderzo C, et al., "Impact of thrombotic thrombocytopenic purpura on leukemic children undergoing bone marrow transplantation," Bone Marrow Transplant, 2000; 26:1005-9, 5 pgs.
Ueda N, et al., "Predictive Value of Circulating Angiopoietin-2 for Endothelial Damage-Related Complications in Allogeneic Hematopoietic Stem Cell Transplantation," Biology of Blood and Marrow Transplantation, 2014; 20:1335-40, 6 pgs.
Van Der Plas RM, et al., "von Willebrand factor proteolysis is deficient in classic, but not in bone marrow transplantation-associated, thrombotic thrombocytopenic purpura," Blood, 1999; 93:3798-802, 6 pgs.
Waters AM, et al. "aHUS caused by complement dysregulation: new therapies on the horizon," Pediatr Nephrol, 2011; 26:41-57, 17 pgs.
Worel N, et al., "ABO-incompatible allogeneic hematopoietic stem cell transplantation following reduced-intensity conditioning: close association with transplant-associated microangiopathy," Transfus Apher Sci, 2007; 36:297-304, 8 pgs.
Wuhl E, et al., "Strict blood-pressure control and progression of renal failure in children," N Engl J Med, 2009; 361:1639-50, 12 pgs.
Yamada-Fujiwara M, et al., "Diagnosis of intestinal graft-versus-host disease and thrombotic microangiopathy after allogeneic stem cell transplantation," The Tohoku Journal of Experimental Medicine, 2012; 227:31-7, 8 pgs.

Canadian Office Action dated Jan. 25, 2017 for Application No. CA 2,921,856, 4 pgs.
Canadian Office Action dated Feb. 8, 2018 for Application No. CA 2,921,856, 4 pgs.
Canadian Office Action dated Nov. 30, 2018 for Application No. CA 2,921,856, 5 pgs.
Extended European Search Report and Opinion dated Mar. 20, 2017 for Application No. EP 14843902.9, 9 pgs.
European Exam Report dated Jan. 25, 2018 for Application No. 14843902.9, 4 pgs.
European Search Report, Supplementary, and Written Opinion dated Dec. 17, 2018 for Application No. EP 1680827.3, 8 pgs.
International Search Report and Written Opinion dated Dec. 31, 2014 for Application No. PCT/US2014/055922, 12 pgs.
International Search Report and Written Opinion dated Feb. 7, 2019 for Application No. PCT/US2018/062210, 12 pgs.
Japanese Office Action dated Nov. 30, 2018 for Application No. 2016-542879, 6 pgs.
Japanese Office Action dated Nov. 30, 2018 for Application No. 2016-542879, 9 pgs. English Translation.
U.S. Appl. No. 61/878,119, filed Sep. 16, 2013.
Ghosh, S., et al., "Interfering with interferons in inflammatory bowel disease," Gut Microbiota, British Medical Assoc, 2006, 55(8):1071-1073, 3 pgs.
Khosla, J., et al., "Hematopoietic stem cell transplant-associated thrombotic microangiopathy: current paradigm and novel therapies," Bone Marrow Transplantation, 2018, 53:129-137, 9 pgs.
Kundra, A., et al., "Interferon induced thrombotic microangiopathy (TMA): Analysis and concise review," Critical Reviews in Oncology/Hematology, Elsevier, 2017, 112:103-112, 10 pgs. (XP029945081).
Kundra, A., et al., "Interferon induced thrombotic microangiopathy (TMA): Analysis and concise review," Critical Reviews in Oncology/Hematology, Science Direct, 2017, 112:103-112, 21 pgs. (XP55825262).
"Total Complete Activity," Wikipedia, downloaded Nov. 6, 2021 from https://en.wikipedia.org/w.index.php?title=Total_complement_activity&oldid=1026475679, last updated Jun. 2, 2021, 2 pgs.
European Search Report, Partial, and Provisional Written Opinion dated Jul. 28, 2021 for Application No. EP 18883814.8, 14 pgs.
European Search Report, Supplementary, and Written Opinion dated Oct. 29, 2021 for Application No. EP 18883814.8, 12 pgs.
Japanese Office Action, Notice of Reasons for Refusal, dated Aug. 2, 2021 for Application No. JP 2019-234471, 8 pgs.
Gloude, N.J., et al., "Thinking Beyond HLH: Clinical Features of Patients with Concurrent Presentation of Hemophagocytic Lymphohistiocytosis and Thrombotic Microangiopathy," J Clin Immunol, 2020, 40(5):699-707, 9 pgs.
Mizuno, K., et al., "Integration of Pharmacodynamic Biomarker with Modeling & Simulation for Eculizumab Precision Dosing in Pediatric Patients with Hematopoietic Stem Cell Transplant Associated-Thrombotic Microangiopathy," Abstracts from the 11$^{th}$ American Conference of Pharmacometrics (ACoP11), vol. 2, Nov. 9-13, 2020, TUE-045, ISSN:2688-3953, XP093033648, 3 pgs.
International Search Report and Written Opinion dated Apr. 3, 2023 for Application No. PCT/US2022/053603, 9 pgs.
Japanese Office Action, Decision of Dismissal of Amendment, dated Jun. 13, 2022 for Application No. JP 2019-234471, 2 pgs.
Japanese Office Action, Decision of Refusal, dated Jun. 13, 2022 for Application No. JP 2019-234471, 4 pgs.
Japanese Office Action, Reconsideration Report by Examiner before Appeal, dated Jan. 4, 2023 for Application No. JP 2019-234471, Appeal No. 2022-016367, 2 pgs.
Japanese Office Action, Notice of Reasons for Refusal, dated Jan. 11, 2023 for Application No. JP 2022-014712, 2 pgs.

\* cited by examiner

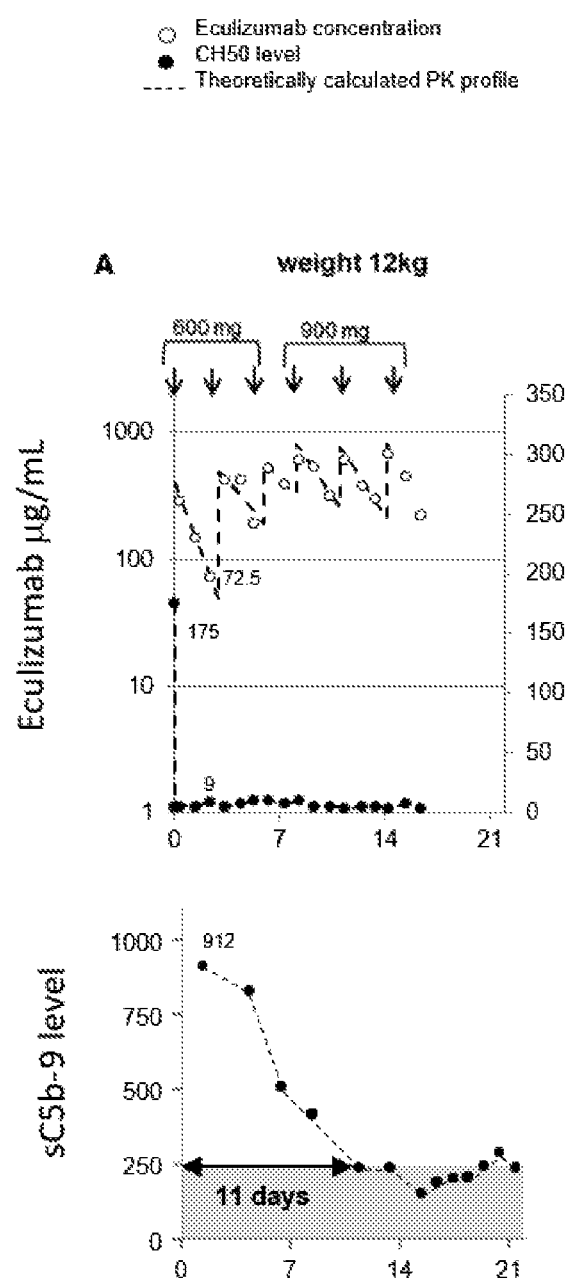

| Patient weight | Induction dose | Maintenance dose |
|---|---|---|
| 40 kg and over | 900 mg | 1200 mg every 2 weeks |
| 30 kg to less than 40 kg | 600 mg | 900 mg every 2 weeks |
| 20 kg to less than 30 kg | 600 mg | 600 mg every 2 weeks |
| 10 kg to less than 20 kg | 600 mg | 300 mg every 2 weeks |
| 5 kg to less than 10 kg | 300 mg | 300 mg every 2 weeks | ns
DOSING ALGORITHM FOR COMPLEMENT INHIBITOR

CROSS-REFERENCE TO RELATED APPLICATIONS

This application claims priority to and the benefit of U.S. Provisional Application 62/172,987, Dosing Algorithm for Eculizumab, Jodele et al, filed Jun. 9, 2015, the contents of which are incorporated in their entirety by reference.

BACKGROUND

Personalized dosing using complement inhibitor is not currently performed, but would be the best strategy for disease control for various disease states. For example, personalized dosing could be used to either avoid thrombotic microangiopathy (TMA) induced organ injury or revert TMA induced organ injury. While in certain circumstances, complement inhibitor is a necessary treatment, the lack of personalized dosing yields less than ideal results, and in many cases, can actually put the patient at risk for ineffective treatment. Further, dosing with complement inhibitor can be very expensive. Thus, inefficient dosing not only can lead to significant financial waste, but worse, puts the patient at risk of a delayed improvement of disease or even death, where effective administration of complement inhibitor is not achieved.

One or more of the aforementioned problems is addressed by Applicant's invention.

BRIEF SUMMARY

Described are methods and systems for the treatment of individuals having a disorder characterized by complement system dysregulation. The described methods and systems may be used for a variety of purposes, including for example, establishing one or both of a general or personalized dosing schedule for treatment using a complement inhibitor, establishing a dosage schedule sufficient to maintain an effective amount of complement inhibitor, establishing general dosing schedules for novel complement modifying agents and identifying a treatment regimen and/or dose eliminating the possibility of under dosing medication, and treatment regimen and/or dose for reducing or preventing toxicity in a patient.

BRIEF DESCRIPTION OF THE DRAWINGS

FIG. 1A. Relationship between serum eculizumab serum concentration and CH50 suppression. A total of 365 pairs of serum eculizumab concentrations and CH50 levels from 18 patients are displayed on this plot. Each individual subject is marked in a different shade. The x-axis shows eculizumab concentrations in log-scale. The y-axis shows the percent of pretreatment (normal) CH50 serum concentration determined by the assay, where CH50 values in each patient were normalized by their individual pretreatment CH50 value. The 6 observations with asterisks were CH50 levels when the eculizumab concentration was below the limit of detection (<10 mg/mL) during therapy. FIG. 1B. Dashed horizontal line marks 10% of CH50 normal value. Dashed vertical line represents the suggested therapeutic serum eculizumab concentration of >99 mg/mL.

(FIG. 14B) Observed versus individual predicted eculizumab concentrations estimated by the post-hoc Bayesian method. (FIG. 14C) Conditional weighted residuals versus population model predicted eculizumab concentrations. (FIG. 14D) Conditional weighted residuals versus time after dose. Open circles represent the observations in (FIG. 14A) and (FIG. 14B), and conditional weighted residuals in (FIG. 14C) and (FIG. 14D). The dashed and solid lines in (FIG. 14A) and (FIG. 14B) represent the identity line. The solid lines represent the linear regression lines.

DETAILED DESCRIPTION

Figure 1A:
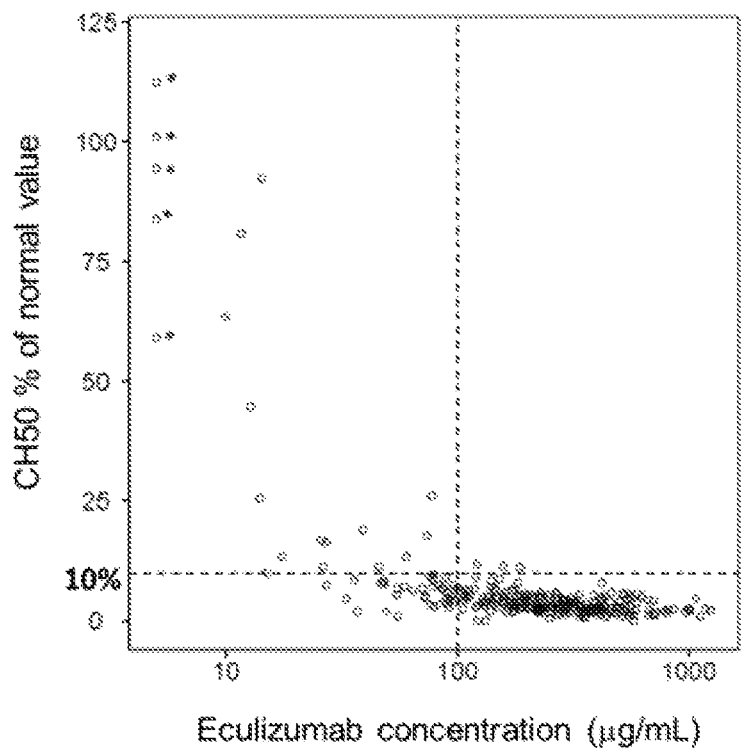
FIG. 1A-B.

The instant disclosure relates generally to the use of complement inhibitors, for example, in a disease state in which sC5b-9 is a variable that can be used as a marker of effectiveness of the complement inhibitor to be administered to an individual in need thereof. Applicant has found that, by measuring sC5b-9 and body weight in an individual, a dosing schedule can be effectively determined on an individual basis (for example, as a means of personalized medicine), addressing one or more problems in the art as described above. The disclosed methods and systems allow for determination of a dose or dosing schedule that avoids one or more of the following problems: under-dosing medication that results in a decrease of complement inhibitor below a therapeutic concentration in the blood levels of a patient resulting in a lack of clinical effectiveness, an initial and/or follow-up dose that provides an unnecessarily complicated dosing schedule that compromises patient compliance or ease of administration (such as based on access to treatment), waste of the therapeutic due to over administration or too high of a dose, and toxicity as a result of overmedication of a patient receiving a complement inhibitor.

Applicant has found that measurement of sC5b-9 permits the generation of general guidelines that can be used to establish dosing scheduled for new complement inhibitors (for example dosing schedule to be listed in new medication insert packets) and also guide treatment in an individual based on initial sC5b-9 levels and body weight, or, with the use of more sophisticated methods and real-time processing of data, generation of a personalized dose and/or dosing schedule. The methods described herein allow for both general guidelines that can be used to propose dosing regimens for new complement blockers (for example, a dosing listing in a medication insert packet) and also a personalized dosing schedule for a specific patient in a specific clinical situation (personalized dosing). Both the general guidelines and personalized dose/dosing schedule provided by Applicant's discovery may be used to dramatically improve patient care and improve the likelihood of survival in a patient in need of such treatment.

In a further aspect, Applicant's invention addresses the problem of failing to identify potential therapeutic agents as a result of ineffective dosing. Potential complement inhibitors under development may not be properly assessed for efficacy due to an insufficient initial dose and/or follow up dosing, such that proper, therapeutic levels are not achieved and/or maintained in particular clinical situations. For example, a drug dosing schedule may be established based on patients that have a different disease, or in normal "well patients" that have different clearance of the drug. As a result, the resulting dosing schedule for a different disease or in patients having the disease may be incorrect or inefficient. The instant disclosure may further address this need, providing a means by which a dose and dosing schedule can be optimized for an individual, thereby allowing proper assessment of the therapeutic benefit of a new complement inhibitor for use as a medical treatment.

In a yet further aspect, Applicant's disclosure relates to methods of identifying an appropriate dose of a complement inhibitor, administering an appropriate dose of a complement inhibitor, identifying and/or carrying out an effective dosing schedule, and systems for employing the described methods.

In one aspect, a method of treating an individual having a disorder characterized by complement dysregulation where terminal complement activity is measured by the level of terminal soluble complex activity (sC5b-9) in blood is disclosed. The method may comprise the steps of measuring with an assay an sC5b-9 concentration in the individual and measuring body weight in the individual, and administering a complement inhibitor to the individual based on the measurements of body weight and sC5b-9 concentration. The body weight and sC5b-9 measurements may be carried out prior to administration of the complement inhibitor. In one aspect, the assay used to determine the sC5b-9 concentration measures sC5b-9 levels in a blood sample of the individual.

In one aspect, the method may comprise the step of determining the point in time at which a decline in a blood concentration of the therapeutic agent will be below a therapeutic level for that particular agent in the individual, using the following Equation I:

$$Cp = Dose/Vd * e^{-(CL/Vd)*t}$$

$$CL = 98.6 \times (WT/70)^{0.75} \times (preC5b9/422)^{0.73}$$

$$Vd = 5.72 \times (WT/70)^{1.0}$$

wherein
Cp=Plasma concentration (μg/ml) at "t";
Dose=initial dose (mg);
e=a mathematical constant, approximately equal to 2.71828;
t=time after the dose (hour);
WT=Body weight (in kg); and
preC5b9=soluble C5b-9 level prior to treatment.

After the initial administration of complement inhibitor, one or more subsequent doses of the compliment inhibitor may be provided to the individual, wherein the one or more subsequent dose is administered at a point in time (t) at which the compliment inhibitor serum concentration is predicted to fall below said therapeutic level, as provided by the equation above.

The measurements can be taken before starting therapy with the initial dose of complement inhibitor. That is, patients weight and sC5b-9 level can be obtained and the algorithm will be used before starting therapy to determine when the blood levels drop below a therapeutic level and a second dose of the therapeutic needs to be given.

In another aspect, a "rolling algorithm" method may be used, wherein the dosing schedule may be recalculated when a new value of sC5b-9 is obtained from the patient. This allows for a continuous therapy that can be evaluated and adjusted in real time as the condition of the patient changes.

In one aspect, the complement inhibitor may be a terminal complement inhibitor at C5. For example, the complement inhibitor may be eculizumab. The complement inhibitor may be an inhibitor at other complement cascade sites in Lectin, Classical, or Alternative complement pathways where terminal complement activation (as measured by sC5b-9 level in the blood) indicates presence or activity of the disease and may be used as a marker to determine the effectiveness of particular therapeutic agent in altering complement activation level.

In one aspect, the complement inhibitor may be eculizumab. In this aspect, the therapeutic level is at least about 99 μg/mL. In further aspects, therapeutic level for new complement altering agents can be determined by using Applicant's previously proposed methods measuring blood total complement activity (CH50), therapeutic agent blood level, terminal complement activation by blood sC5b-9 level and clinical response, as published in Variable Eculizumab Clearance Requires Pharmacodynamic Monitoring to Optimize Therapy for Thrombotic Microangiopathy after Hematopoietic Stem Cell Transplantation. Jodele S, Fukuda T, Mizuno K, Vinks A A, Laskin B L, Goebel J, Dixon B P, Chima R S, Hirsch R, Teusink A, Lazear D, Lane A, Myers K C, Dandoy C E, Davies S M. Biol Blood Marrow Transplant. 2016 February; 22(2):307-15. doi: 10.1016/j.bbmt.2015.10.002. Epub 2015 Oct. 9. PMID: 26456258 and Eculizumab therapy in children with severe hematopoietic stem cell transplantation-associated thrombotic microangiopathy. Jodele S, Fukuda T, Vinks A, Mizuno K, Laskin B L, Goebel J, Dixon B P, Teusink A, Pluthero F G, Lu L, Licht C, Davies S M. Biol Blood Marrow Transplant. 2014 April; 20(4):518-25. doi: 10.1016/j.bbmt.2013.12.565. Epub 2013 Dec. 25. PMID: 24370861

The disorder characterized by an increase in soluble terminal complement complex activity (sC5b-9) may be any one of a variety of different complement-associated disorders. Complement-associated disorders include any medical disorder, the treatment of which would benefit directly or indirectly from inhibition of the complement system. The disorders are generally characterized by inappropriate regulation of the complement system such as inappropriate: (i) activation of the complement system or (ii) duration of an activated complement system in a subject. Complement-associated disorders include, but are not limited to, hematopoietic stem cell transplant-associated TMA (TA-TMA), solid organ transplant associated TMA (for example, but not limited to, kidney transplant, liver transplant, heart transplant, lung transplant, muti-visceral organ transplant), inflammatory and autoimmune disorders. A complement-associated disorder can be, e.g., antibody mediated rejection (ABMR), donor-specific antibody (DSA) triggered tissue injury, chronic inflammation, inflammatory diseases, degenerative diseases, immunosuppression, angiogenesis, cancer (Pio et al., "Complement inhibition in cancer therapy," Seminars in Immunology 25 (2013) 54-64), RA; antiphospholipid antibody syndrome (APS); lupus nephritis; ischemia-reperfusion injury; aHUS; typical (also referred to as diarrheal or infectious) hemolytic uremic syndrome (tHUS); DDD; neuromyelitis optica (NMO); multifocal motor neuropathy (MMN); MS; macular degeneration (e.g., AMD); HELLP syndrome; TTP; spontaneous fetal loss; Pauci-immune vasculitis; epidermolysis bullosa; recurrent fetal loss; and traumatic brain injury. In some embodiments, the complement-associated disorder is a complement-associated vascular disorder such as a cardiovascular disorder, myocarditis, a cerebrovascular disorder, a peripheral (e.g., musculoskeletal) vascular disorder, a renovascular disorder, a mesenteric/enteric vascular disorder, vasculitis, Henoch-Schδelein purpura nephritis, systemic lupus erythematosus-associated vasculitis, vasculitis associated with rheumatoid arthritis, immune complex vasculitis, Takayasu's disease, dilated cardiomyopathy, diabetic angiopathy, Kawasaki's disease (arteritis), venous gas embolus (VGE), and restenosis following stent placement, rotational atherectomy, and percutaneous transluminal coronary angioplasty (PTCA). Additional complement-associated disorders include, without limitation, myasthenia gravis (MG), cold agglutinin disease (CAD), dermatomyositis, paroxysmal cold hemoglobinuria (PCH), Graves' disease, atherosclerosis, Alzheimer's disease, systemic inflammatory response sepsis, septic shock, spinal cord injury, glomerulonephritis, Hashimoto's thyroiditis, type I diabetes, psoriasis, pemphigus, autoimmune hemolytic anemia (AIHA), idiopathic thrombocytopenic purpura (ITP), Goodpasture syndrome, Degos disease, catastrophic APS (CAPS), sickle cell disease (for example, for treatment of vaso-occlusive crisis with complement blockade) and Extracorporeal Membrane Oxygenation (ECMO) or hemodialysis circuit induced complement activation.

In one aspect, the administration of the therapeutic agent may be discontinued when an outcome selected from no active hematologic TMA symptoms, improvement in affected organ function, sustained normal plasma sC5b-9 concentration, CH50 suppression <10% of normal values for longer than two weeks without drug redosing, and combinations thereof is observed.

In one aspect, the methods may include the step of administering an additional dose of complement inhibitor at the predicted time serum concentration falls below the desired concentration. In a further aspect, where a clinical event known to affect clearance is observed, such clinical event may be assayed and/or assigned a value to recalculate a dosing schedule. Clinical events and interventions that have a potential to alter therapeutic agent concentration in the blood (for example, but not limited to clinically significant blood loss, large volume blood product infusion, administration of complement factors containing products, administration of plasma containing products, therapeutic plasma exchange) may require recalculation of dosing schedule for certain individual based of clinical indicators and laboratory test values using to monitor patients with complement mediated disorder.

In one aspect, a system using the disclosed methods may be employed. The system may comprise a device designed to carry out one or more steps of the disclosed methods. The device may take a variety of forms, for example, a computer or device, for example, a handheld device. The device may employ a system in which measurements assayed by the clinician or a laboratory may be inputted into the system and a personalized treatment schedule for the individual will be displayed. The system may have the further capability to receive additional information concerning clinical features (such as blood loss, for example) that may compromise a treatment schedule, such that the resulting personalized treatment schedule is adjusted based on this additional information. A non-limiting example of output to be used by a clinician is shown in FIGS. 17A and 17B.

Figure 17A:
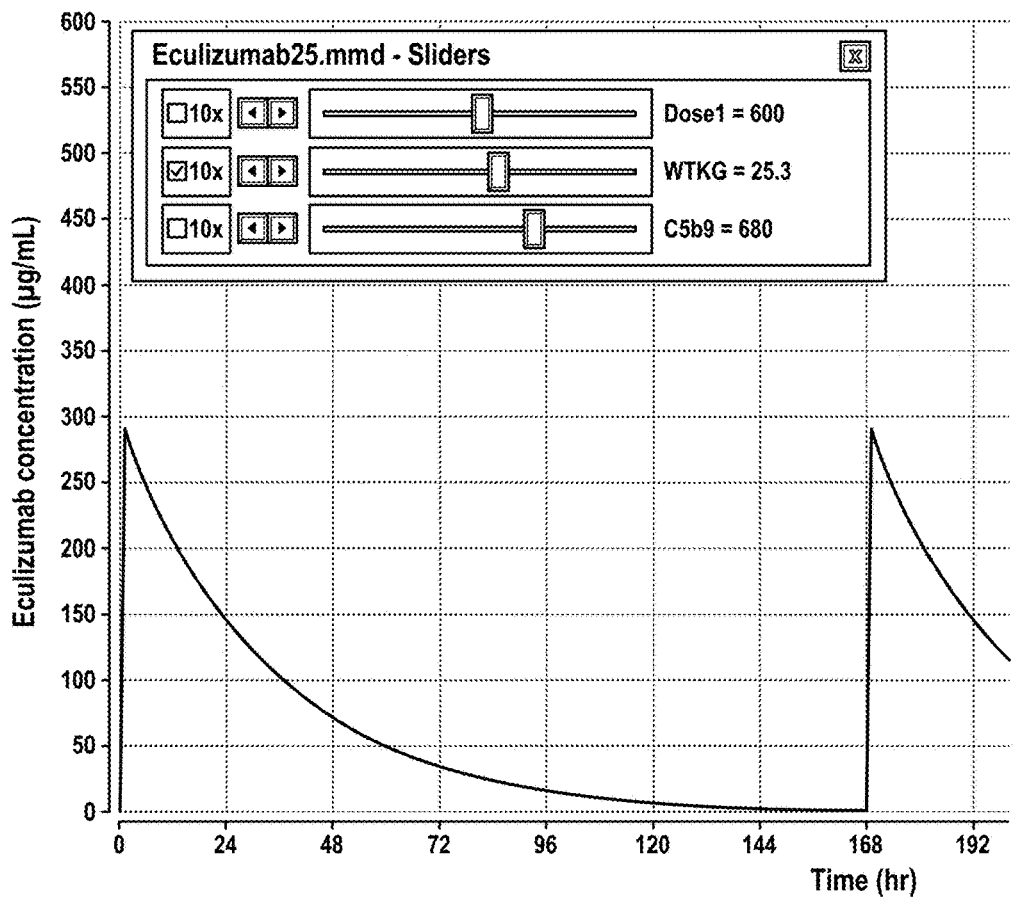
FIGS. 17A-B. depict examples of eculizumab clearance after first dose in two different HSCT patients using proposed algorithm. The Y axis shows eculizumab serum concentration (μg/mL) and the X axis shows time in hours after first eculizumab dose administration. Hour 0 is eculizumab administration time, hour 168 is time for weekly dosing in the current medication insert packet for eculizumab.
Figure 17B:
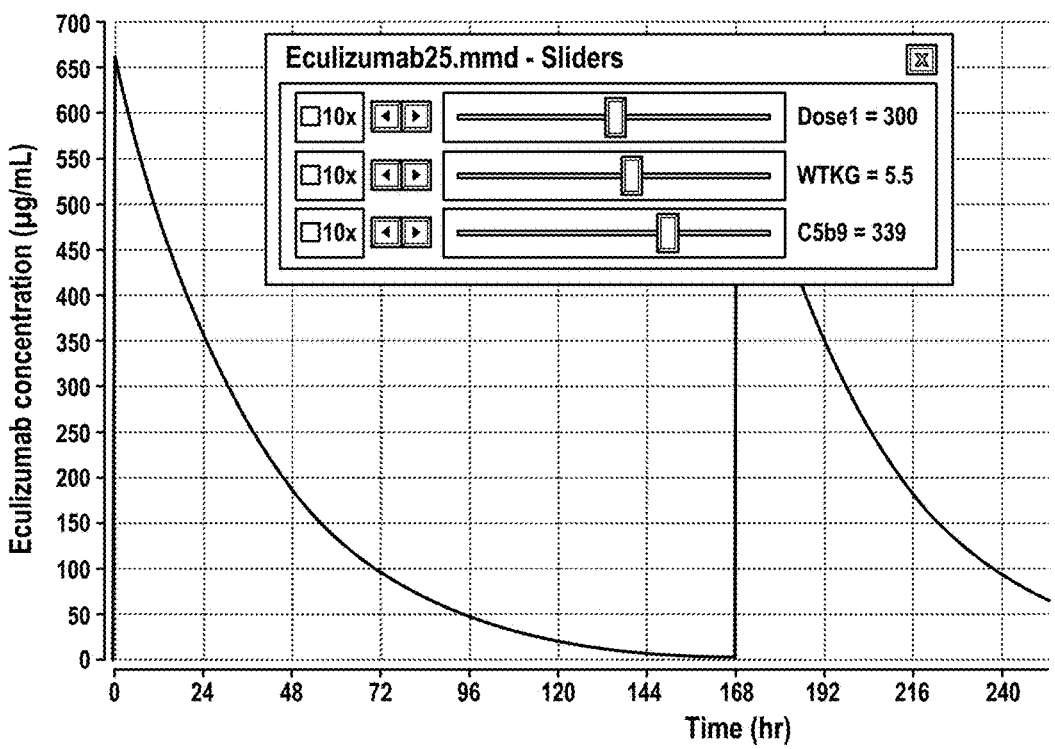

FIGS. 17A and 17B depict personalized eculizumab clearance for two specific patients. The top part of each panel indicates data provided for PK/PD calculation in algorithm slider display: patient's weight (kg), plasma sC5b-9 level (ng/mL) and eculizumab dose (mg). Patient 1, shown in FIG. 17A depicts the following: Patient's weight is 25.3 kg, pre-therapy sC5b-9 level is 680 ng/mL and the first eculizumab dose is 600 mg. FIG. 17A shows that after the first eculizumab dose, the drug peak level is 290 μg/mL (above therapeutic). The drug clearance curve generated using the disclosed methods indicates that the eculizumab drug level will drop below a therapeutic level of 100 μg/mL in approximately 36 hours after drug administration. It is evident that this patient will have lower than therapeutic drug level from hour 36 until hour 168 using the currently recommended eculizumab dosing scheduling. This inadequate dose will allow uncontrolled complement activation. FIG. 17B depicts Patient 2 data: Patient's weight is 5.5 kg, pre-therapy sC5b-9 level is 339 ng/mL, and the first eculizumab dose is 300 mg. FIG. 17B shows that after the first eculizumab dose, drug peak level is >650 μg/mL (above therapeutic). The drug clearance curve generated indicates that the eculizumab drug level will drop below the therapeutic level of 100 μg/mL 72 hours after drug administration. It is evident that this patient will have lower than therapeutic drug level from hour 72 until hour 168 if the clinician is using the currently recommended dosing schedule. This inadequate dose will allow uncontrolled complement activation.

These two examples from HSCT patients treated with eculizumab illustrate how such factors as pre-treatment plasma sC5b-9 level and patient's actual weight affect eculizumab clearance. It also illustrates that application of standardized dosing regimen would be significantly under dosing both patients and compromising clinical care. This particular display of drug clearance allows the user to adjust timing of the dose based on desired drug level as the personalized drug clearance curve is displayed over the time and not at one particular time point. For example, if the desired drug level for patient 1 is 150 μg/mL, then the second dose would be given in 24 hours, based on the personalized dosing curve generated.

The system may further employ additional fields related to patient care such as patient identification and disease and treatment related information, as well as alerts and calendars to assist in care.

In one aspect, a dosing table is disclosed. The dosing table may be used for determining the time in which a complement inhibitor will fall below therapeutically effective levels. The table may take a variety of different forms, for example, as shown in Table 8. The table may include a first region or area that specifies an initial amount of complement inhibitor administered, a second region or area that specifies a range of sC5b-9 levels, a third region or area that specifies a range of body weights, and a fourth region or area that specifies a time period in which the complement inhibitor is expected to fall within a therapeutically effective level. The time period is calculated based on Equation I as described above. In one aspect, the dosing table may be packaged with a complement inhibitor.

Examples

While the foregoing invention may be used for administration of complement inhibitor in general in a variety of disease states, the following is a non-limiting example illustrating use with the complement inhibitor eculizumab. The anti-C5 antibody complement inhibitor eculizumab is a terminal complement inhibitor suitable as a therapeutic option for HSCT-associated TMA. As described herein, Applicant has examined the pharmacokinetics and pharmacodynamics (PK/PD) of eculizumab in children and young adult HSCT recipients with TMA and activated complement to determine drug dosing requirements. Prospectively collected laboratory samples and clinical data from 18 HSCT recipients with high-risk TMA (from the pilot study) presenting with complement activation who were treated with eculizumab were analyzed, the data later validated with an additional 11 patients. Complete data set from 10 patients in this cohort was used for pilot PK/PD data. Applicant measured eculizumab serum concentrations, total hemolytic complement activity (CH50), and plasma sC5b-9 concentrations. Population PK/PD analyses correlated eculizumab concentrations with complement blockade and clinical response and determined inter-individual differences in PK parameters. Applicant also compared transplant survival in patients treated with eculizumab (n=18, pilot study) to patients with the same high-risk TMA features who did not receive any targeted therapy during a separate prospective observational study (n=11). In the PK analysis, Applicant found significant inter-patient variability in eculizumab clearance, ranging from 16 to 237 mL/hr/70 kg in the induction phase. The degree of complement activation measured by sC5b-9 concentrations at the start of therapy, in addition to actual body weight, were significant determinants of eculizumab clearance and disease response. Sixtyone percent of treated patients had complete resolution of TMA and were able to safely discontinue eculizumab without disease recurrence. Overall survival was significantly higher in treated subjects compared to untreated patients (56% versus 9%, p=0.003). Complement blocking therapy is associated with improved survival in HSCT patients with high-risk TMA who historically have dismal outcomes, but eculizumab pharmacokinetics in HSCT recipients differ significantly from reports in other diseases like atypical hemolytic uremic syndrome and paroxysmal nocturnal hemoglobinurina. Applicant found that he disclosed eculizumab dosing algorithm, including pre-treatment plasma sC5b-9 concentrations, patient's actual body weight, and the first eculizumab dose (mg), accurately determined eculizumab concentration-time profiles for HSCT recipients with high-risk TMA. This algorithm may be used to guide eculizumab treatment and ensure that future efficacy studies use the most clinically appropriate and cost-efficient dosing schedules.

Thrombotic microangiopathy (TMA) is a common complication after hematopoietic stem cell transplantation (HSCT).[1-4] The reported incidence of TMA after HSCT varies from 0-74% in retrospective studies.[5] Applicant's recent prospective observational study, using rigorous monitoring for microangiopathy, identified TMA in 39% of patients.[6] Consistent with the literature, the clinical presentation of TMA ranged from mild (laboratory test changes only) to severe life-threatening disease.[7-11] Half of the patients with TMA in the study had severe multi-visceral disease contributing to dismal transplant outcomes in untreated patients.

Figure 7:
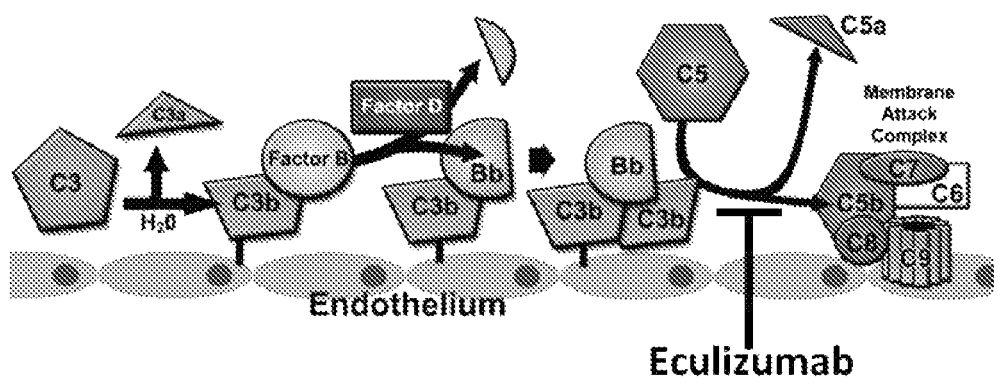
FIG. 7 displays terminal complement blockade at C5, including alternative complement pathway dysregulation in endothelial injury and the mechanism of action of eculizumab Activation of C3 by hydrolysis leads to formation of C3b with a reactive thioester moiety, which covalently binds to an endothelial cell surface. C3b binding is enhanced on injured endothelial cells. Once C3b is bound to the cell surface, Factor B binds to C3b and is cleaved by Factor D to its enzymatically active fragment Bb. The C3bBb complex serves as a C3 convertase, generating more molecules of C3b, which can in turn complex with new molecules of Bb, leading to amplification of this pathway. C3bBb bound to a second molecule of C3b (C3bBb·C3b) serves as a C5 convertase, which cleaves C5 into C5a and C5b. This fragment of C5b serves as a nidus for the formation of the lytic membrane attack complex (C5b-9) on the endothelial cell surface, furthering endothelial cell injury. Eculizumab is a humanized monoclonal antibody that is a terminal complement inhibitor. Eculizumab inhibits the cleavage of C5 to C5a and C5b by the C5 convertase, which prevents the generation of the terminal complement complex C5b-9 preventing endothelial damage by membrane attack complex.

Traditional risk factors for TMA include endothelial injury from conditioning chemotherapy, radiation, calcineurin inhibitors, or infections.[12-15] However, there is increasing evidence that complement is involved in the pathophysiology of HSCT-associated TMA and ensuing renal injury. In a recently published prospective study by Applicant, HSCT recipients with proteinuria and terminal complement activation, defined as elevated plasma concentrations of the soluble terminal complement complex (sC5b-9), in addition to hematologic markers of TMA, had very poor survival (<20%) and were classified as having high-risk TMA[16]. In contrast, patients with hematologic TMA markers but without evidence of complement activation or proteinuria all survived despite not receiving any targeted interventions, and were classified as having low-risk TMA. Following this prospective study, all HSCT recipients with high-risk TMA were offered eculizumab therapy in light of the known poor prognosis. Eculizumab is a humanized monoclonal antibody against the complement component C5 that prevents endothelial damage by blocking formation of the membrane attack complex FIG. 7. Applicant initially noted a lag in clinical response in the first six patients observed, despite achieving an eculizumab serum concentration expected to be therapeutic of >99 μg/mL.[17] Applicant performed population based pharmacokinetic and pharmacodynamic (PK/PD) analyses in an extended cohort of children and young adults receiving HSCT who were treated with eculizumab, using plasma sC5b-9 concentrations as a marker of TMA disease activity to establish dosing and monitoring regimens for future prospective efficacy studies.

Methods

Study Subjects

All consecutive HSCT recipients who received eculizumab[18] for high-risk TMA from January 2012 to June 2014 were included in the PK/PD analyses. All study subjects had high-risk TMA features including plasma sC5b-9 concentrations above normal (>244 ng/mL) and nephrotic range proteinuria (random urine protein/creatinine ratio >2 mg/mg) present at the time of TMA diagnosis, in addition to hematologic TMA markers (schistocytes, elevated lactate dehydrogenase (LDH), reduced haptoglobin, de novo anemia and thrombocytopenia) as previously determined by Applicant.[6] Clinical and laboratory data were prospectively captured from the electronic medical record into HSCT databases. The institutional review board approved the study. Informed consent was obtained from all study subjects.

Response Assessment

A hematologic response to eculizumab was defined as normalization of LDH, resolution of the need for red blood cell (RBC) and platelet transfusions, and disappearance of schistocytes. A complete clinical response was defined as resolution of organ failure, normalization of the hematologic parameters noted above combined with a doubling of the cystatin C-estimated glomerular filtration rate (eGFR) and improvement of proteinuria to values below the nephrotic range, as defined by a random spot urine protein-to-creatinine ratio <2 mg/mg and normalization of plasma sC5b-9.[17] Discontinuation of therapy was considered successful if there was no TMA recurrence eight weeks after the last eculizumab dose with normal sC5b-9 and CH50 values.

Eculizumab Blood Concentration and Complement Testing

Soluble terminal complement complex activity (sC5b-9) was measured in plasma by enzyme-linked immunosorbent assay (normal plasma concentration is below 244 ng/mL). CH50 was measured in serum using a hemolytic assay (normal 101-300 units). ADAMTS13 activity (normal >67%) was measured at the time of TMA diagnosis to rule out thrombotic thrombocytopenic purpura.[19] Eculizumab serum concentrations were measured as a clinical test.[20] Recommended therapeutic eculizumab concentrations during eculizumab induction therapy was >99 μg/mL based on recent publications in patients with aHUS[21] and by Cambridge Biomedical laboratory recommendations for clinical testing.

Eculizumab Treatment Protocol

Eculizumab dosing was performed using CH50 monitoring as previously published.[1] CH50 was measured prior to starting eculizumab to assure that the patient did not have underlying hypocomplementemia that would preclude the use of CH50 for complement blockade monitoring and was then measured daily during therapy. The first eculizumab dose was based on weight as recommended for children with aHUS.[20] In brief, patients weighing <40 kg started with 600 mg intravenously and patients weighing ≥40 kg started with 900 mg intravenously. Subsequent dose adjustments were as follows: if CH50 after the first eculizumab dose remained suppressed (<10% of normal) for at least six days, the subsequent dose was administered on the seventh day and then weekly while maintaining CH50<10%.[22,23] If CH50 increased above 10% of normal sooner than six days, the next dose was given when CH50 elevation above 10% normal was documented. If there was no adequate CH50 suppression after intensifying dosing interval or there was no hematologic response for longer than ten days, the eculizumab dose was increased by 300 mg/dose. After establishing the required dosing schedule to maintain adequate CH50 suppression, induction therapy was continued until patients achieved a hematologic TMA response and had a documented eculizumab serum concentration >99 μg/mL, at which point a maintenance schedule was started.[17] Complete blood counts (including schistocytes) and LDH were monitored daily. Haptoglobin, urinalyses, random urine protein/creatinine ratio, and cystatin C-eGFR were monitored weekly. Eculizumab serum concentrations were measured daily during induction therapy, and plasma sC5b-9 was monitored at least three times per week during therapy. In addition, Applicant measured plasma sC5b-9 weekly starting prior to HSCT therapy until clinical TMA diagnosis to evaluate the relationship between the first plasma sC5b-9 elevation and appearance of hematologic signs of TMA. Eculizumab serum concentration results were not available in real-time for drug dose adjustments in the pilot cohort, but were used later for PK/PD analysis to correlate eculizumab serum concentrations with sC5b-9 and CH50 values and clinical response.

Eculizumab induction dosing was continued until hematologic TMA response was achieved and CH50 remained suppressed below 10% of normal for four weeks, at which point a maintenance schedule was started by giving the same dose every two weeks while maintaining CH50<10%.[1] When CH50 remained suppressed for longer than two weeks during the maintenance therapy without drug re-dosing and without active TMA signs eculizumab therapy was stopped. TMA laboratory markers, serum CH50 and plasma sC5b-9 continued to be monitored 2-3 times per week for at least eight weeks. All patients received antibacterial prophylaxis against *Neisseria meningitidis* until at least eight weeks after discontinuation of eculizumab and until normalization of CH50, since meningococcal vaccination does not provide protection in severely immunocompromised HSCT patients.[24]

Eculizumab Pharmacokinetic and Pharmacodynamics Analysis

Standard PK analyses were performed using a one compartment model to obtain eculizumab PK parameters such as systemic clearance (CL) and volume of distribution (Vd), as previously described.[17] Population PK modeling was performed using NONMEM version 7.2 (ICON Development Solutions, Ellicott City, MD, USA) to characterize population PK parameters, focusing on the induction phase ($1^{st}$ dose), and to identify significant covariates for eculizumab PK parameters. A one compartment PK model was used as the structural base model. Total body weight (BW, also expressed as "WT")) and plasma sC5b-9 concentration at initiation of the therapy were tested as potential covariates for each PK parameter in the covariate analysis. Selection of covariates was based on a significant reduction of the objective function value (OFV) by stepwise forward inclusion ($p<0.05$), backward elimination ($p<0.01$), and by graphical evaluation of goodness-of-fit plots. The eculizumab serum concentration required to suppress CH50 to <10% of normal (complete blockade) was determined based on a receiver operating characteristic (ROC) curve to maximize the Youden's Index which is defined as specificity+sensitivity−1 (FIG. 7).[25]

Post-Transplant Survival

Since high-risk TMA has very high mortality and all patients presenting with high-risk features during the study period received eculizumab therapy, a direct comparison of treated and untreated patients with the same disease risk was not able to be performed. Instead, to preliminarily assess outcomes among HSCT recipients treated with eculizumab for high-risk TMA (n=18), Applicant performed a survival analysis using untreated subjects as a comparator group who were consecutive (unselected) cases with the same high-risk TMA features (n=11) from a separate prospective observational study aiming to determine TMA risk stratification.[6]

Simulation of Eculizumab Serum Concentrations-Time Profiles

Eculizumab concentration-time profiles were simulated in this patient population using various pre-treatment plasma sC5b-9 concentrations (ng/mL) using Berkley Madonna software (www.berkeleymadonna.com/) based on PK model and PK parameter estimates developed by Applicant.

Statistical Analysis

Median (interquartile range) and frequencies (percent) were used to describe continuous and categorical variables, respectively. Differences by group for continuous and categorical variables were determined using Fisher exact and Wilcoxon tests, respectively. Survival curves were estimated using the Kaplan-Meier method. Log-rank tests were used to assess the difference in overall survival by group. Analyses were performed using R version 3.1.3. All statistical tests were two-sided and significance was assessed at $p<0.05$.

Results

Study Subjects

TABLE 1

Study demographics and disease characteristics. Data shown as median (interquartile range) or n(%).

| | Treated with eculizumab n = 18 | Untreated subjects n = 11 | p-value |
|---|---|---|---|
| Transplant characteristics | | | |
| Age (years)# | 4.6 (2-15.2) | 8.2 (1.8-11.8) | 0.9 |
| Actual weight (kg) | 17 (13.5-44.5) | 15.4 (12.6-44) | 0.77 |
| Male gender | 11 (61.1%) | 7 (63.6%) | 1 |
| Race | | | 0.4 |
| Caucasian | 13 (72.2%) | 6 (54.5%) | |
| Non-Caucasian | 5 (27.8%) | 5 (45.5%) | |
| Underlying diagnosis | | | 0.03 |
| Bone marrow failure | 0 (0%) | 3 (27.3%) | |
| Immune Deficiency | 9 (50%) | 6 (54.5%) | |
| Malignancy | 8 (44.4%) | 1 (9.1%) | |
| Other | 1 (5.6%) | 1 (9.1%) | |
| Donor type | | | 0.04 |
| Related | 1 (5.6%) | 4 (36.4%) | |
| Unrelated | 13 (72.2%) | 7 (63.6%) | |
| Autologous | 4 (22.2%) | 0 (0%) | |
| Stem cell source | | | 1 |
| Bone Marrow | 13 (72.2%) | 7 (63.6%) | |
| PBSCs | 4 (22.2%) | 3 (27.3%) | |
| Cord Blood | 1 (5.6%) | 1 (9.1%) | |
| HLA Match | | | 0.11 |
| Matched | 4/14 (22.2%) | 7/11 (63.6%) | |
| Mismatched | 10/14 (55.6%) | 4/11 (36.4%) | |
| Conditioning Regimen | | | 0.44 |
| Myeloablative | 12 (66.7%) | 5 (45.5%) | |
| Reduced intensity | 6 (33.3%) | 6 (54.5%) | |
| Cyclosporine GVHD prophylaxis | 14/14 (100%) | 11/11 (100%) | 1 |
| GVHD (grade 3-4) | 9 (50%) | 6 (54.5%) | 0.70 |
| Disease features at TMA diagnosis | | | |
| TMA diagnosis (day after HSCT) | 30 (18-55.5) | 26 (17-38.5) | 0.79 |
| Blood sC5b-9 (normal <244 ng/ml) | 373.5 (301-744) | 458.5 (324.2-708.4) | 0.24 |
| Cystatin C estimated GFR (mg/ml) | 29.5 (17.8-46) | 45 (34.5-56) | 0.77 |

TABLE 1-continued

Study demographics and disease characteristics. Data shown as median (interquartile range) or n(%).

| | Treated with eculizumab n = 18 | Untreated subjects n = 11 | p-value |
|---|---|---|---|
| Urine random protein/creatinine ratio | 10.3 (6.5-20.8) | 2.6 (2.5-3.3) | <0.0001 |
| Renal replacement therapy | 7 (38.9%) | 4 (36.4%) | 1 |
| Hypertension | 18 (100%) | 11 (100%) | 1 |
| Pericardial effusion | 15 (83.3%)* | 9 (81.8%)** | 1 |
| PRES | 2 (11%) | 1 (9.1%) | 1 |
| CNS bleed | 1 (5.6%) | 0 (0%) | 1 |
| Pulmonary hypertension | 3 (16.7%) | 2 (18%) | 1 |
| Gastrointestinal bleeding | 11 (61%) | 7 (63.6%) | 1 |
| Respiratory failure | 2 (11%) | 1 (9.1%) | 1 | three subjects in treated group and two in untreated group were young adults 19-29 years of age.
*4/15 (26.7%) and **1/9 (11%) had cardiac tamponade.
GVHD, graft versus host disease;
TMA, thrombotic microangiopathy;
GFR, glomerular filtration rate;
PRES: posterior reversible encephalopathy syndrome;
CNS, central nervous system.

Most subjects were children younger than 18 years of age, but the eculizumab treatment group included three young adults and the untreated group had two young adults 19-29 years of age. The degree of terminal complement activation, organ injury, and incidence of acute stage 3-4 graft versus host disease (GVHD) was similar in treated patients (n=18) and untreated patients (n=11). All 29 subjects had a normal plasma sC5b-9 concentration (<244 ng/mL) prior to starting transplant chemotherapy. Plasma sC5b-9 became elevated above normal a median of three days after HSCT (range day −9 to day +13, where day 0 is day of stem cell infusion) in the 18 subjects treated with eculizumab, and continued to rise until eculizumab therapy was initiated. Hematologic TMA signs in these patients appeared at median day +30 after HSCT (range day +18 to day +56). ADAMTS13 activity was >10% in all 29 study subjects (median of 53%, range 29-95%) at TMA diagnosis. All patients had a normal INR (International normalized ratio of prothrombin time of blood coagulation) and negative direct antibody test (DAT).

Pharmacokinetic and Pharmacodynamic Analyses

Figure 1B:
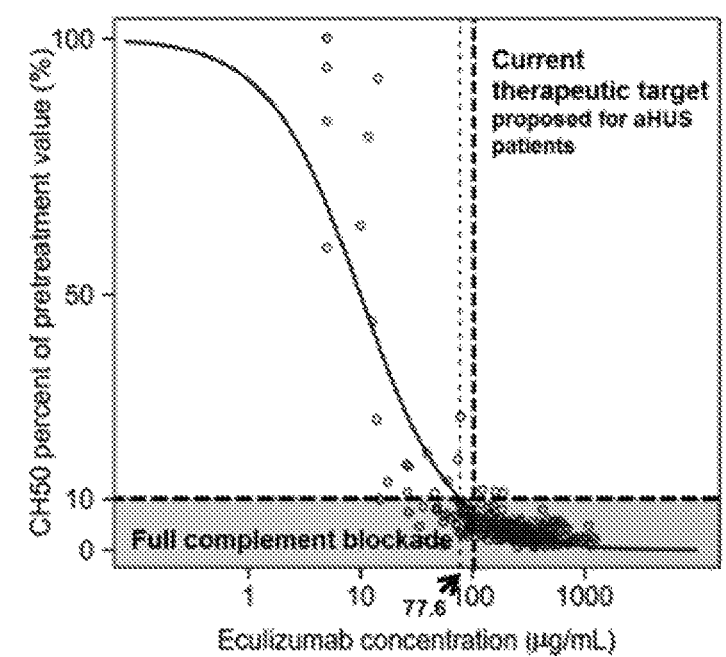

A total of 824, 316 and 401 observations were available for CH50, sC5b9 and eculizumab concentrations, respectively. First, Applicant determined that a serum eculizumab concentration of >99 μg/mL was sufficient to suppress total hemolytic activity (CH50) to <10% of the normal value during induction therapy (FIG. 1), but the time that complement activity remained blocked after each drug dose was quite variable between subjects, and in the same subject over time, indicating variable eculizumab clearance. A decline of eculizumab serum concentration to <99 μg/mL as drug was cleared from the circulation was correlated with a rising CH50, as expected, indicating incomplete complement blockade (FIG. 1). Based on this observation, Applicant further examined serum eculizumab concentration-time profiles with the goal of identifying co-variates that contributed to the inter-individual variability in eculizumab clearance seen during the course of the therapy in order to propose dosing strategies that would allow sustained complement blockade (CH50<10%).

Figure 2:
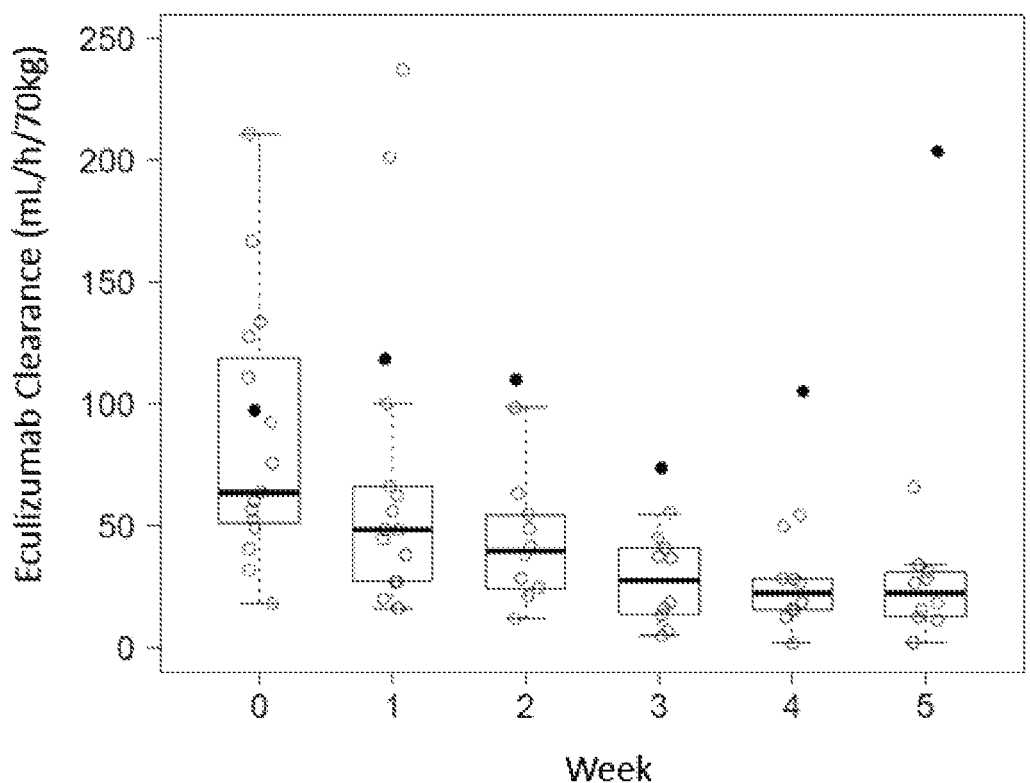
FIG. 2. Eculizumab clearance during the first 5 weeks of therapy. Open circles show individual clearance values standardized by body actual body weight using allometric scaling. Individual clearance estimates were plotted weekly using the pharmacokinetic analysis. Box plot shows 25th, 50th, and 75th percentiles with range. Eculizumab clearance is highest at the start of the therapy and declines by week 5 to become nearly equal to the eculizumab clearance reported during maintenance therapy in patients in aHUS or PHN. Shaded circles represent the clearance trajectory in a patient with severe gastrointestinal bleeding. These clearances were excluded from summary statistics and are displayed here to illustrate high drug clearance in a patient with clinically significant blood loss and high blood product support.

Applicant analyzed changes in systemic eculizumab clearance during the first five weeks of therapy by performing PK analyses (FIG. 2).[26] Apparent systemic clearances were normalized by allometrically scaled body weight to account for body size differences and to allow comparison across the range of patients' age.[27] Applicant found significant inter-patient variability in eculizumab clearance, ranging from 16 to 237 mL/hr/70 kg during the induction phase. Mean drug clearance normalized for weight during the first week of therapy was 3.5-fold higher than during the fifth week (86.0 mL/hr/70 kg-patient versus 24.4 mL/hr/70 kg-patient). In a previous clinical trial for adults with aHUS, population pharmacokinetic analysis found that eculizumab had a volume of distribution of 6.14 L and a clearance of 14.6 mL/h in a patient with aHUS who weighed 70 kg. In contrast, modeling in a PNH patient weighing 70 kg found the mean clearance of eculizumab was 22 mL/h and the mean volume of distribution was 7.7 L.[18,28,29] Interestingly, mean drug clearance during the fifth week of therapy in HSCT recipients was still higher (24.4 ml/h/70 kg) than mean clearance reported in patients with aHUS (13.9 mL/hr/70 kg) or PNH (21.7 mL/hr/70 kg) receiving maintenance therapy. It is important to note that HSCT recipients with severe and persistent gastrointestinal bleeding requiring >20 mL/kg/day of red cell transfusions and >10 ml/kg/day of apheresis platelets had high drug clearance during all five weeks of therapy, suggesting that specific clinical events such as severe blood loss can further accelerate drug clearance, emphasizing the need for continuous PD monitoring to optimize complement blockade.

Figure 3:
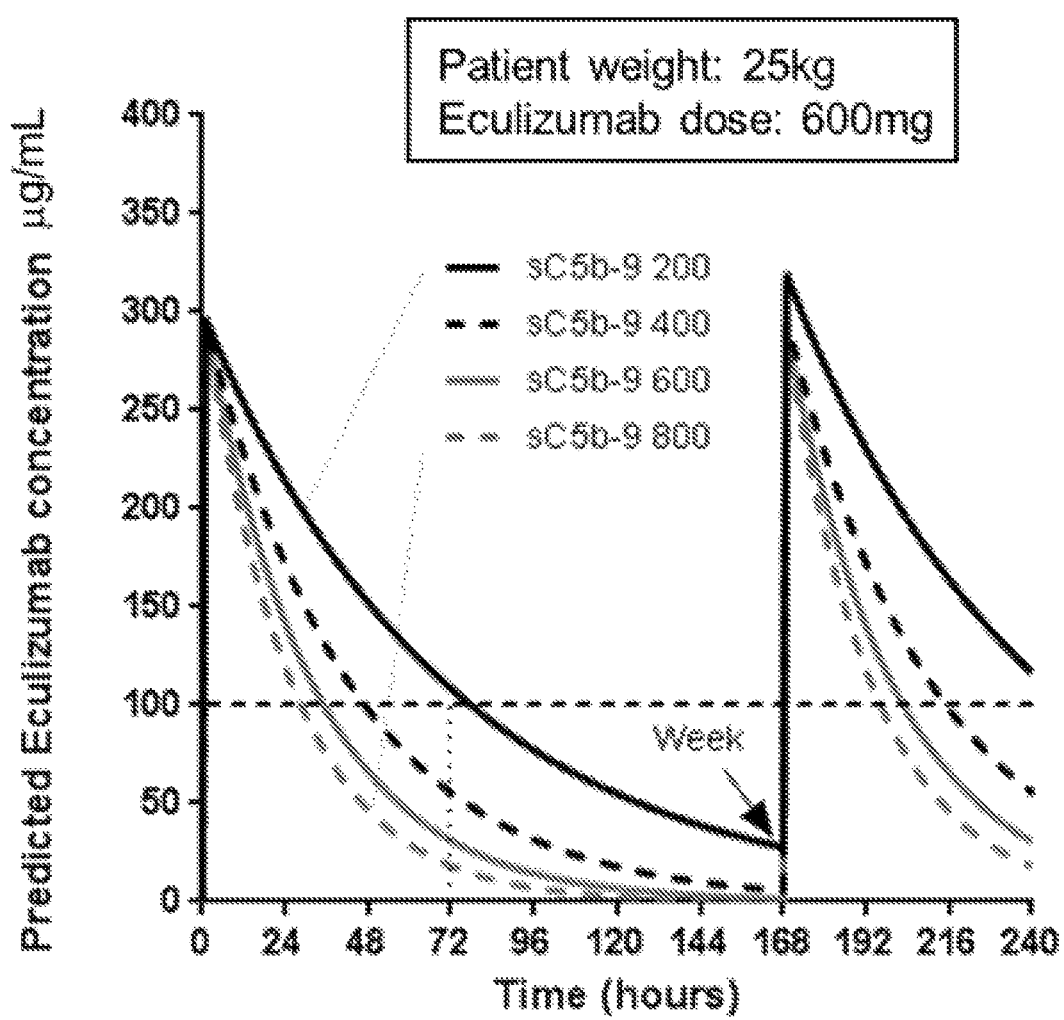
FIG. 3. Pretreatment plasma sC5b-9 concentration predicts eculizumab clearance. Representative case of eculizumab serum concentrations-time profiles simulated with mean population estimates are shown (Table 2) for 25-kg HSCT recipient receiving the eculizumab induction dose of 600 mg every 7 days as currently recommended for the same weight patient with aHUS. The y-axis shows predicted eculizumab serum concentration. The x-axis shows time in hours from the first eculizumab dose administered (hour 0) to the second dose given in 1 week (hour 168). The horizontal dotted line marks the suggested therapeutic eculizumab target above >99 µg/mL required for complement blockade. Eculizumab serum concentration-time clearance curves are marked in different shades and line types representing different plasma sC5b-9 concentration (from 200 to 800 ng/mL) at the start of eculizumab therapy (normal plasma sC5b-9 concentration is 74 to 244 ng/mL). Eculizumab elimination rate increases along with increasing plasma sC5b-9 concentration. This algorithm using patient's actual weight, initial eculizumab dose (mg), and plasma sC5b-9 concentration value at the start of therapy allows prediction of the time when eculizumab serum concentration declines below required therapeutic level and when next medication dose should be given to sustain complement blockade.
Figure 8A:
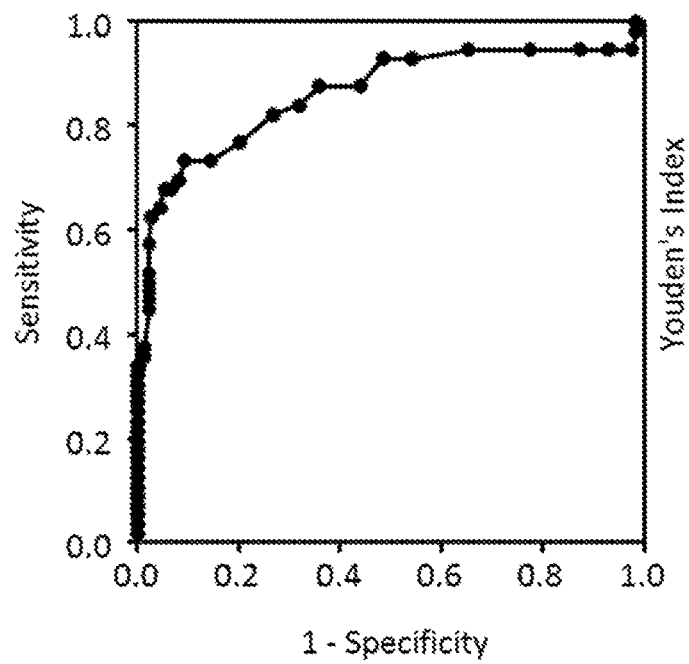
FIG. 8. A total of 279 pairs of serum eculizumab concentration and CH50 levels were used for this analysis. The CH50 levels measured daily by the hemolysis assay with normal CH50 values being 101-300 Each daily CH50 value was correlated with eculizumab serum concentrations measured in the same sample. Eculizumab serum concentration was counted as zero for pre-treatment (baseline) CH50 before starting the drug. Eculizumab levels may be obtained using an ELISA-based method for the measurement of the serum level of eculizumab as would be readily understood by one of ordinary skill in the art. The correlation between the CH50 and the serum eculizumab concentration was determined based on the ROC curve to maximize the Youden's Index which is defined as specificity+sensitivity−1. According to the analysis, a CH50<15.5 units for this particular assay would indicate that the eculizumab level is >99 μg/mL (b). All eculizumab concentrations were classified into two groups above and below the CH50 cutoff (c). The y-axis shows eculizumab concentrations in log-scale. The x-axis shows the CH50 level groups. Horizontal lines represent medians. Posterior statistical analysis was performed to evaluate the difference in eculizumab concentration between the two groups by the Mann-Whitney U test. Knowing that eculizumab concentration of >99 μg/mL is required to completely block complement as shown in FIG. 1, the target CH50 for clinical monitoring would be <15.5 units using the hemolysis assay.
Figure 8B:
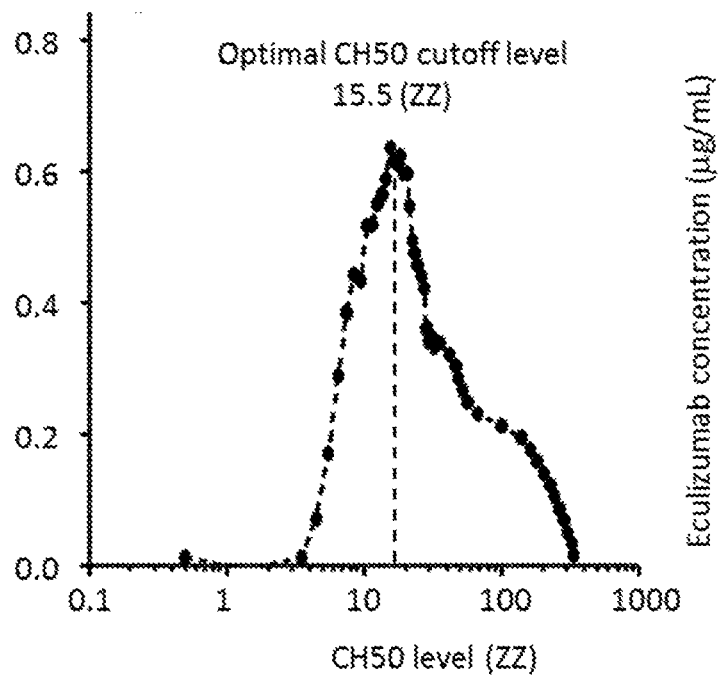
Figure 8C:
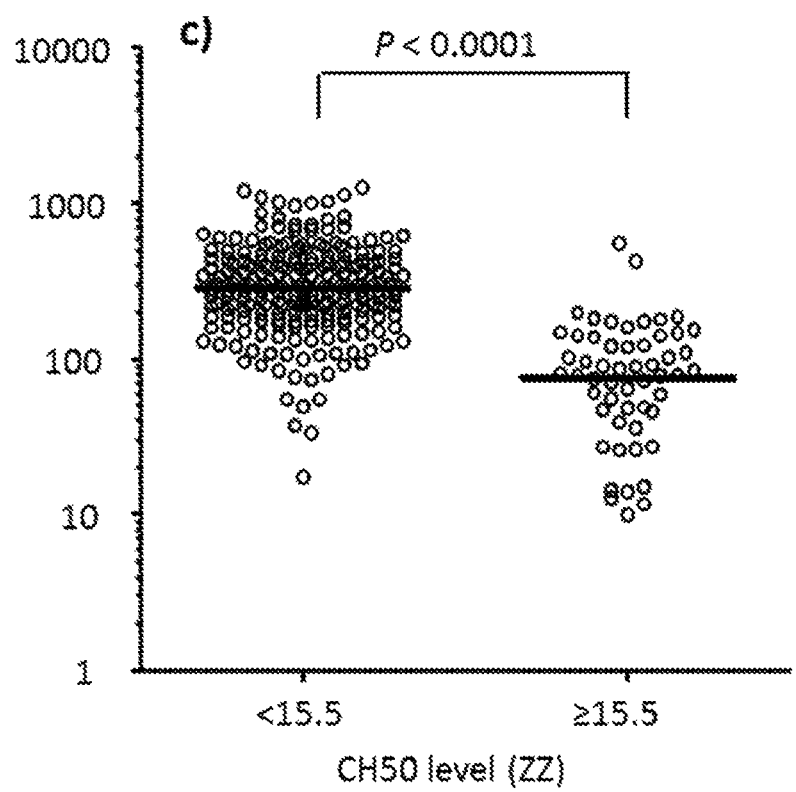
Figure 9:
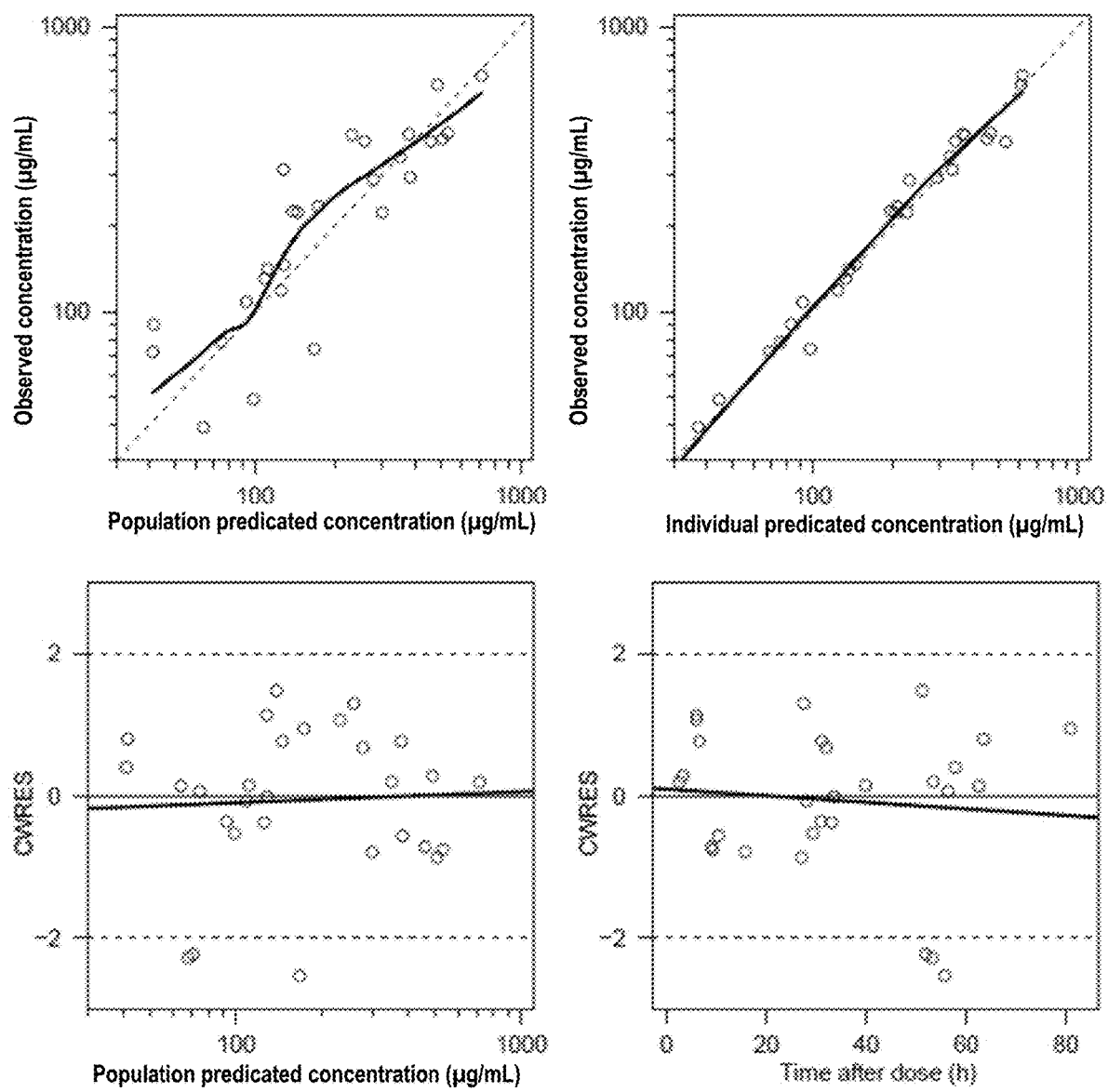
FIG. 9. Observed eculizumab concentrations versus the population model predicted eculizumab concentrations; observed eculizumab concentrations versus individual eculizumab predicted concentrations estimated by the post-hoc Bayesian method; conditional weighted residuals (CWRES) versus population predicted eculizumab concentrations, and CWRES versus time after the dose.
Figure 10:
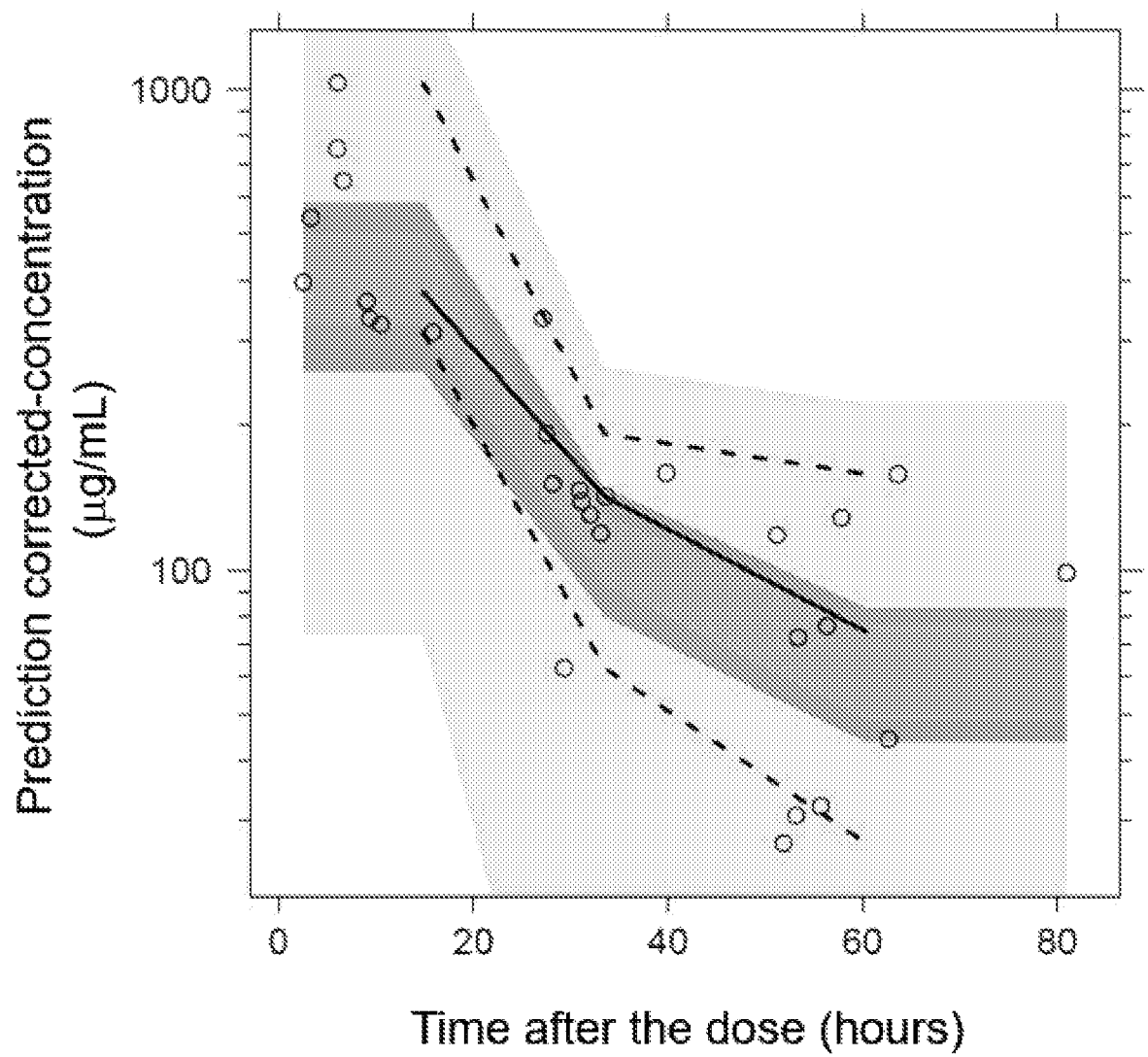
FIG. 10. Open symbols represent prediction corrected-observed concentrations. Solid line represents the observed median value and lower and upper dashed lines represent the observed 5th and 95th percentiles, respectively. Shaded areas indicate the confidence intervals of the 5th, 50th and 95th percentile of the simulated values.

Applicant's analysis identified that pre-treatment plasma sC5b-9 concentration was a significant covariate for initial eculizumab clearance in addition to the patient's actual body weight. The mean pre-treatment plasma sC5b-9 concentration in the study cohort was 422 ng/mL (normal <244 ng/ml). PK modeling showed that 70 kg subject with sC5b-9 of 422 ng/mL will have a mean eculizumab clearance of 98.6 mL/hr with a mean volume of distribution was 5.72 L (Table 2, Table 3 and Table 4 and FIG. 8 and FIG. 9). In FIG. 3, an example of changes in eculizumab clearance (PK profiles) for a 25 kg child receiving 600 mg eculizumab based on different pre-treatment plasma sC5b-9 concentrations using Applicant's pharmacokinetic model is provided. This simulation uses patient's actual weight (kg), eculizumab dose (mg) and pre-treatment plasma sC5b-9 concentration (ng/mL) and allows the exact time (in hours) when the eculizumab serum concentration would decline below the targeted therapeutic level of 99 μg/mL required to suppress CH50<10% to be defined, indicating the time when a subsequent eculizumab dose is needed. For example, in a 25 kg HSCT recipient with TMA with a pre-treatment plasma sC5b-9 concentration of 422 ng/mL, the eculizumab serum concentration is predicted to decline below 99 μg/mL around 48 hours after a first drug dose of 600 mg, while current recommendations in a 25 kg child with aHUS suggest weekly administration of 600 mg doses.[20] Simulations using different body weights and eculizumab doses predicted that eculizumab serum concentration will decline below 99 μg/mL in less than 72 hours in any HSCT recipient who has elevated plasma sC5b-9 concentration above 244 ng/mL.

TABLE 2

Population pharmacokinetic parameter estimates in the induction phase (after first eculizumab dose).

| Parameter | Population estimates Mean (% RSE) | Inter-individual variability (CV %) Mean (% RSE) |
|---|---|---|
| $CL_{pop}$ (mL/h/70 kg) | 98.6 (9%) | 20.3% (26%) |
| $Vd_{pop}$ (L/70 kg) | 5.72 (21%) | 63.1% (21%) |
| Exponent for pre-sC5b-9 | 0.73 (14%) | 0% (fix) |

Final model:
$CL = CL_{pop} \times (WT/70)^{0.75} \times (preC5b9/422)^{0.73}$;
$Vd = Vd_{pop} \times (WT/70)^{1.0}$ wherein
$CL_{pop}$: mean population clearance;
$Vd_{pop}$: mean population volume of distribution;
WT: Actual body weight (kg);
pre-sC5b-9: soluble C5b-9 plasma concentration at initiation of treatment;
Actual body weight (WT) was included using allometric scaling and was identified as a significant covariate for CL and Vd (reduction of objective function value (OFV) by 17.3 (p < 0.01)).
Inclusion of pre-sC5b-9 onto CL led to a reduction of OFV by 9.55 (p < 0.01) with a power exponent estimate of 0.73. See Tables 3 and 4 and FIGS. 2-4 for more details.

TABLE 3

Patient demographics for population pharmacokinetic analysis.

|  | Mean | SD | Median | Range |
|---|---|---|---|---|
| Eculizumab induction dose (mg) 300 mg/600 mg/900 mg | 1/4/5 | | | |
| Sex (male/female) | 6/4 | | | |
| Actual body weight (kg) | 32.8 | 28.9 | 17.5 | 7-80 |
| Age (years) | 10 | 11.5 | 3.8 | 0.5-29.8 |
| Pre-treatment C5b-9 level (ng/mL) | 422 | 240 | 357 | 187-913 |

TABLE 4

Population pharmacokinetic parameter estimates and bootstrap results using the final model.

| Parameter | Population analysis Mean (% RSE) | Bootstrap analysis (n = 1000) Mean | Bootstrap analysis (n = 1000) % diff, 95% CI |
|---|---|---|---|
| Fixed effects | | | |
| $CL_{pop}$ (mL/h/70 kg) | 98.6 (9%) | 99.0 | 0.4% (81.2-116.1) |
| Exponent of allometry for CL | Fixed to 0.75 | — | — |
| $Vd_{pop}$ (L/70 kg) | 5.72 (21%) | 5.57 | 2.6% (3.94-7.50) |
| Exponent of allometry for Vd | Fixed to 1.0 | — | — |
| C5b-9 | 0.73 | 0.76 | 3.5% (0.48-0.98) |
| Inter-individual variability | | | |
| $\omega_{CL}$ (% CV) | 20.3% (26%) | 19.7% | 3.1% (0.0-28.7) |
| $\omega_{vd}$ (% CV) | 63.1% (21%) | 59.1% | 6.3% (35.5-81.9) |
| Random residual variability | | | |
| $\varepsilon_{prop}$ | 0.0329 (24%) | 0.0327 | 0.8% (0.007-0.059) |
| Final model | | | |

$$CL = CL_{pop} \times (WT/70)^{0.75} \times (sC5b9/422)^{\theta C3b9}$$
$$Vd = Vd_{pop} \times (WT/70)^{1.0}$$

$CL_{pop}$; a population mean of eculizumab clearance (mL/h/70 kg) in a typical 70 kg patient with pretreatment sC5b-9 level of 422 ng/mL,
$Vd_{pop}$; a population mean of volume of distribution (L/70 kg) in a typical 70 kg patient with pretreatment sC5b9 level of 422 ng/mL,
$\omega_{CL}$: Inter-individual variance for eculizumab clearance,
$\omega_{Vd}$: Inter-individual variance for eculizumab volume of distribution,
$\varepsilon_{prop}$; proportional random residual variance,
WT; body weight (kg)
Success rate of bootstrap analysis was 98.3%.
WT; body weight (kg)

Success rate of bootstrap analysis was 98.3%. WT; body weight (kg)

Figure 4B:
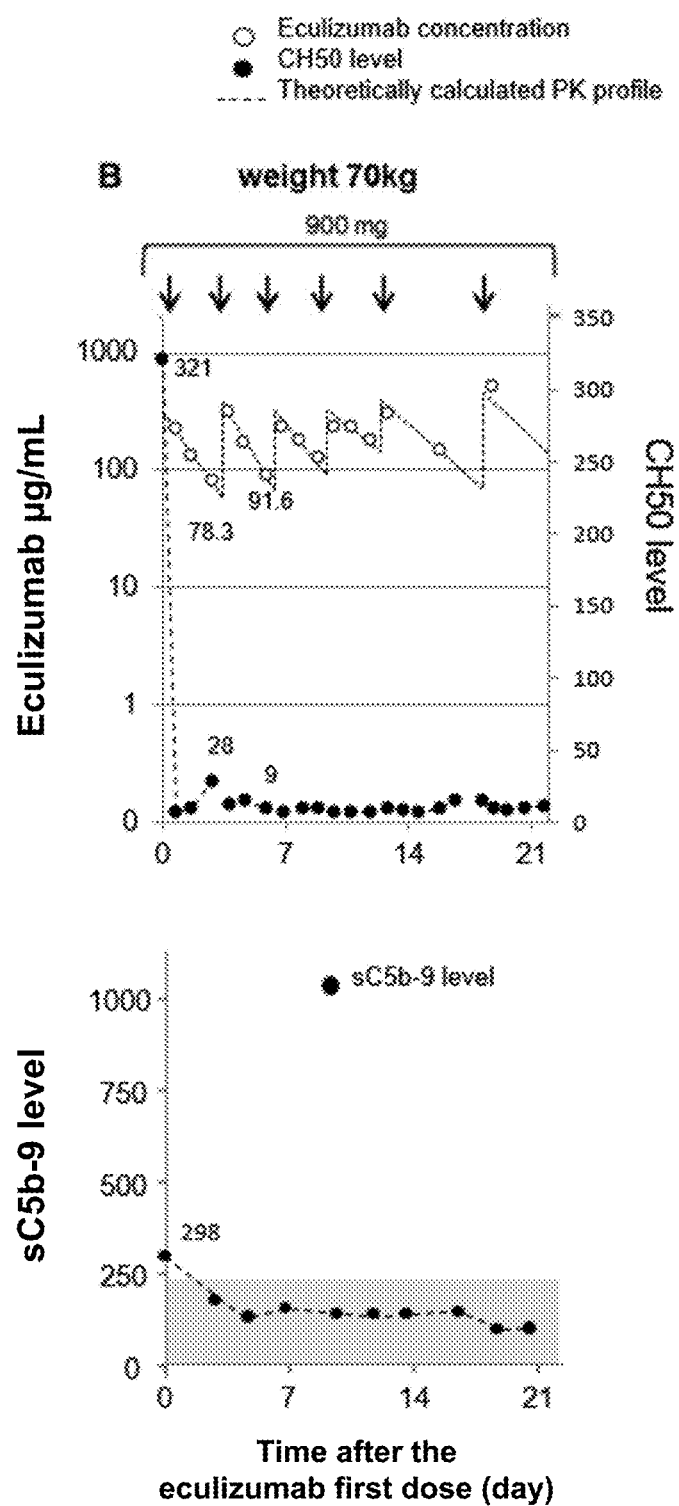
FIG. 4. Correlation of eculizumab serum concentration with blood CH50 and sC5b-9. Eculizumab pharmacokinetic and pharmacodynamic markers are illustrated over time in 2 representative cases during induction therapy. The left and right upper y-axes show eculizumab concentrations and total complement activity (CH50), respectively. The lower y-axis shows plasma sC5b-9 concentration. The x-axis shows time as days from the start of eculizumab therapy. Dosage (mg) and the timing of administration are indicated with arrows on the top of each figure. Open circles in the top panel represent observed eculizumab serum concentrations. Actual measured values are noted beside the circles only when eculizumab serum concentrations were below 99 µg/mL. Dashed lines represent predicted eculizumab pharmacokinetic profiles based on 1-compartmental analysis (see Methods for detail). Shaded circles at the bottom of the same panel represent the CH50. The actual values are listed on the graph only when the CH50 is above 10% of normal value. Shaded circles are connected with solid lines when CH50 measurement are continuous (daily) or dashed lines when intermittent, respectively. Shaded circles show sC5b-9. The actual numbers mark plasma sC5b-9 concentration at initiation of the therapy. The gray boxes mark normal sC5b-9 value of <244 ng/mL. Patients (representative Patient A) with pretreatment sC5b-9 value at least double of normal (>488 ng/mL) require 11 to 13 days of steady eculizumab serum concentration of ≥99 mg/mL with adequately suppressed CH50 (<10% lower limit of normal) to normalize sC5b-9, whereas patients (representative Patient B) with pretreatment sC5b-9 value less than double normal <488 ng/mL take 2 to 5 days to normalize sC5b-9. Clinical response corresponds with normalization of sC5b-9.
Figures 5A, 5B:
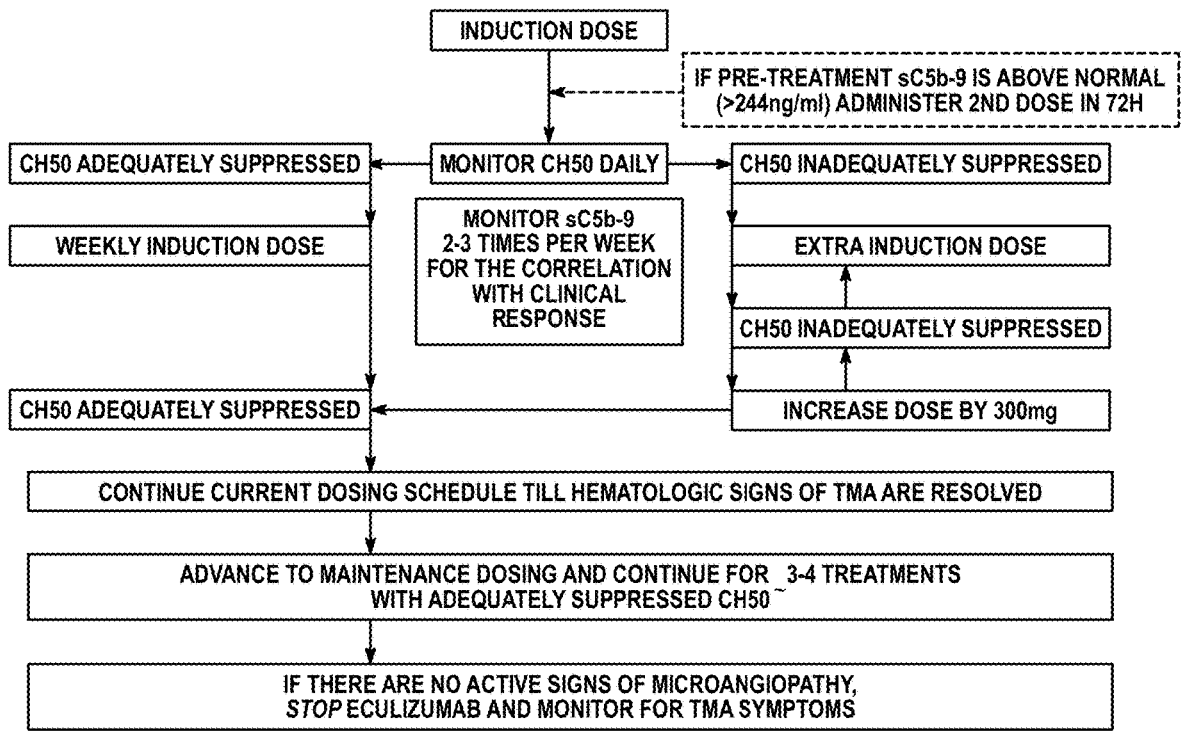
FIG. 5. Eculizumab administration and monitoring schema for HSCT patients with TMA. The first eculizumab dose for HSCT-associated TMA should be given based on patient's weight, as listed in the table (B) according to the eculizumab package insert. If pretreatment plasma sC5b-9 concentration is above normal >244 ng/mL, the second dose should be administered at no later than 72 hours based on personalized PK/PD results. CH50 should be monitored each day during eculizumab induction therapy to determine the subsequent dosing schedule, because patients with TMA often require eculizumab dosing more often than weekly in the beginning of the induction therapy to sustain a therapeutic eculizumab serum concentration (A). To achieve complement blockade in the blood and to maintain therapeutic eculizumab serum concentration of ≥99 μg/mL, CH50 needs to remain adequately suppressed (<10% of the lower limit of normal). Subsequent eculizumab doses need to be given when CH50 becomes inadequately suppressed (rises above 10% of normal laboratory value) but no longer than every 7-day intervals. If CH50 remains inadequately suppressed by dosing at <7-day intervals and sC5b-9 remains elevated, dose should be increased by 300 mg/dose to the maximum of 1200 mg/dose and daily CH50 monitoring should continue. If CH50 is adequately suppressed for at least 6 days, then eculizumab induction doses should be given weekly. When steady CH50 suppression is achieved and hematologic TMA parameters and plasma sC5b-9 normalize, eculizumab should be advanced to a maintenance schedule as listed in the table (B) based on patient's weight, as recommended in eculizumab package insert. CH50 should be checked at least before each eculizumab dose to ensure adequate complement blockade. If TMA remains controlled after 3 to 4 maintenance doses and trough eculizumab level remains above therapeutic, eculizumab may be discontinued. Patients should be carefully monitored with twice a week lactate dehydrogenase, Complete blood count and differential, weekly urinalysis, and twice a week sC5b-9 for 4 weeks after eculizumab therapy is discontinued. Weekly CH50 should be checked until it returns to normal. Antimeningococcal prophylaxis should be provided from the start of the therapy until about 8 weeks after stopping eculizumab and CH50 has returned to normal.

In agreement with the PK/PD modeling, all treated patients in the cohort required eculizumab re-dosing in fewer than 7 days, at least for the first 1-2 weeks of induction therapy, to achieve and sustain CH50<10% and to maintain an eculizumab serum concentration of ≥99 μg/ml. Patients with plasma sC5b-9≥488 ng/mL (>twice normal value) at TMA diagnosis required 11-13 days of therapy with adequately suppressed CH50 to normalize sC5b-9, while patients with plasma sC5b-9<488 ng/mL required 2-5 days to normalize sC5b-9 (FIG. 4). Normalization of plasma sC5b-9 correlated with the beginning of clinical response reflected in hematologic TMA markers and organ function. Based on these data the previously proposed dosing algorithm was updated to include pre-treatment plasma sC5b-9 concentration to determine the need for subsequent dosing during the induction phase of therapy (FIG. 5). A decline in plasma sC5b-9 concentration during eculizumab therapy also correlated with longer intervals of sustained CH50 suppression, indicating slower drug elimination. This was also reflected in advancement of eculizumab dosing intervals to once a week, then once every two weeks and eventually discontinuation of therapy when CH50 remained suppressed <10% for longer than 2 weeks without receiving drug. In responding patients who discontinued therapy, CH50 remained <10% of normal for a median of a 48 days (range 21-81) after the last eculizumab dose, indicating that drug clearance became very slow after TMA was controlled.

Clinical Response to Eculizumab

Eleven of 18 treated patients (61%) achieved complete resolution of TMA with eculizumab therapy. Responders received a median of 16 doses of eculizumab (range 4-38 doses). An HSCT recipient with persistent gastrointestinal bleeding and high drug clearance received the most doses and had the slowest disease response. Median day to hematologic TMA response was 36 days (range 14-90 days), and complete recovery of organ injury occurred in 90 days (range 24-270 days). Proteinuria was the last clinical feature of TMA to resolve. None of the patients received therapeutic plasma exchange (TPE) or fresh frozen plasma (FFP) during eculizumab therapy. TPE was attempted in the first five subjects without adequate response and was stopped prior to starting eculizumab. In subsequent cases, Applicant proceeded directly to eculizumab if supportive measures (withdrawal of calcineurin inhibitors, treatment of GVHD and infections) were not effective.

Eculizumab therapy was discontinued when the following criteria were met: there were no active hematologic TMA symptoms with improvement in overall clinical condition and renal function, sustained normal plasma sC5b-9 concentration <244 ng/mL and CH50 suppression <10% of normal value for longer than two weeks without drug re-dosing. All eleven responders successfully discontinued therapy without TMA recurrence with median follow up of 37 weeks (range 8-128 weeks). One responder died from acute GVHD three months after resolution of TMA. Seven patients (39%) who did not respond to therapy died with active TMA symptoms after receiving a median of four doses of eculizumab (range 2-24 doses). These patients were not able to sustain suppressed CH50<10% and continued to have elevated plasma sC5b-9 concentrations. Five of these seven patients had grade 2-4 acute GVHD at the time of death.

Figure 6:
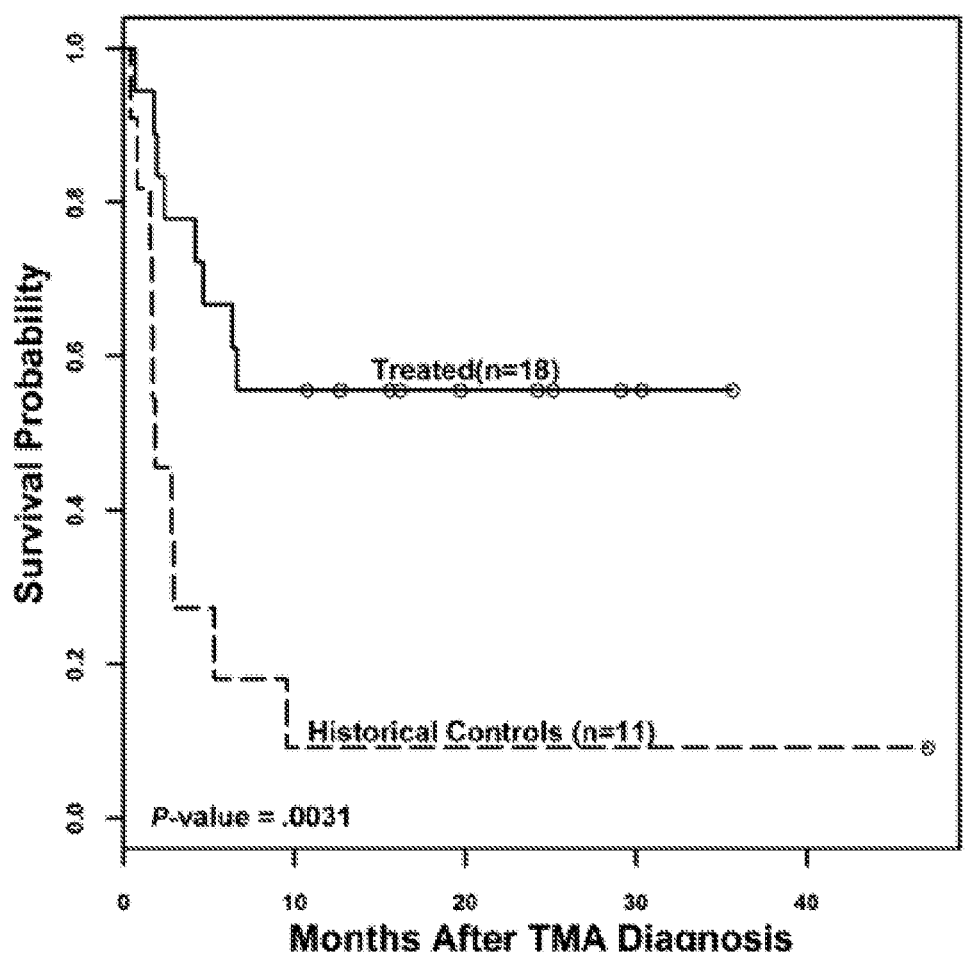
FIG. 6. Survival in HSCT recipients with high-risk TMA. Survival curves for patients with high-risk TMA who were treated with the terminal complement blocker eculizumab ("Treated", n=18) and historical control subjects from prospective observational TMA study with the same high-risk TMA features who did not receive eculizumab ("Historical Controls", n=11) were calculated using Kaplan-Meier and log rank tests starting at TMA diagnosis to assess statistical significance. Patients with high-risk TMA who received eculizumab therapy had better survival than untreated patients who historically are known to have nearly dismal outcome (56% versus 9% at 1 year from TMA diagnosis, P=0.003).

Overall survival one year after TMA diagnosis was 56% in subjects treated with eculizumab while untreated HSCT recipients with the same high-risk TMA features from the separate prospective observational study had 9% survival (p=0.003) (FIG. 6). The primary causes of death in patients treated with eculizumab were GVHD (n=3), pulmonary hemorrhage (n=1), TMA/multi-organ failure (n=2), and fungal infection (n=2). The primary causes of death for the untreated patients from the prospective observational study were TMA/multi-organ failure (n=4), GVHD (n=4), and viral infection (n=2). There were no primary disease relapses and all deaths occurred due to transplant-related mortality. Applicant did not observe any toxicities directly attributed to eculizumab. Infection rates were similar in treated and untreated patients.

Discussion

The PK/PD data indicate that there are significant differences in eculizumab clearance based on TMA activity after HSCT, and personalized pharmacodynamically-directed drug dosing is needed for the best clinical response and most economical use of this expensive drug. While eculizumab clearance in HSCT recipients was much higher at TMA diagnosis than reported in patients with aHUS or PNH, drug clearance became progressively slower as TMA responded to therapy, allowing safe tapering and discontinuation of therapy in all responding patients after TMA resolved. The PK/PD model using the pre-treatment plasma sC5b-9 concentration, actual patient's weight, and the first eculizumab dose (mg) was accurate in predicting eculizumab serum concentration-time profiles and the required dosing schedule for each individual patient in induction therapy when prompt disease control is essential to avoid multi-organ injury. Such a tool, when validated, can be used to predict when the eculizumab serum concentration will decline below levels required to block complement activity and allow accurate determination of the need for subsequent dosing required to sustain complement blockade and to control TMA.

The data show that eculizumab suppresses hemolytic complement activity in the blood, measured as CH50, very quickly, but this suppression is short-lived in HSCT recipients with plasma sC5b-9 concentrations above normal. In addition, the higher sC5b-9 is at the start of therapy, the longer it takes for it to normalize and to achieve a clinical response. Higher pre-treatment sC5b-9 indicates greater tissue injury and inflammation, takes longer to resolve, and requires a more intense dosing regimen, in agreement with Applicant's finding of more severe TMA phenotype and higher mortality in transplant recipients with higher plasma sC5b-9 values.

All subjects with sC5b-9 above normal (>244 ng/mL) cleared eculizumab to <99 µg/mL in less than 72 hours, indicating the need for more frequent dosing than the weekly induction therapy currently recommended for other microangiopathies. Based on these observations, Applicant suggest that HSCT recipients with high-risk TMA should receive personalized dosing for complement blocking agent based on PK/PD monitoring. Notably, in Applicant's cohort, plasma sC5b-9 elevation occurred during conditioning chemotherapy in some cases, while hematologic TMA markers did not become apparent until about 20 days later (range 10-28 days), perhaps indicating early vascular injury from chemotherapy or radiation contributing to TMA etiology. These observations suggest that prospective TMA monitoring and early prompt initiation of therapy may prevent TMA-mediated vascular injury and progression to multi-organ failure. Furthermore, early initiation of therapy when the pre-treatment plasma sC5b-9 concentration is lower, may allow for faster complement blockade and fewer doses of eculizumab to abort TMA.

The PK/PD data showed that eculizumab clearance became progressively slower after normalization of plasma sC5b-9 concentrations, indicating that disease activity was controlled and drug could be dosed at longer intervals. In fact, after five weeks of therapy, initially high drug clearance in HSCT patients became nearly comparable to the drug clearance reported in the maintenance phase for patients with aHUS or PNH. Interestingly, in HSCT recipients who resolved TMA, CH50 remained suppressed after the last eculizumab dose for longer than three weeks, suggesting that drug dosing in the maintenance phase can perhaps be extended over a longer interval than currently recommended for aHUS or PNH and CH50 monitoring could serve as a simple and widely available test for safe tapering of eculizumab therapy.

Notably, drug clearance remained high in a patient with biopsy-proven gastrointestinal TMA associated with severe intestinal bleeding requiring significant blood product support, indicating that personalized eculizumab dosing is needed in HSCT recipients, especially those with other transplant complications. Additionally, the use of plasma containing products (fresh frozen plasma (FFP), or high volumes of platelet products) will increase eculizumab clearance by providing exogenous complement factors, and eculizumab will need to be given more frequently in this setting to maintain complement blockade. None of the study patients received any FFP or therapeutic plasma exchange while on eculizumab therapy. ADAMTS13 activity is often decreased in patients with acute hemolysis and plasma therapy (FFP or TPE) should not be administered in subjects receiving eculizumab who do not meet criteria for a diagnosis of TTP (ADAMTS13<10%).[19,30,31] In Applicant's study, reduced ADAMTS13 levels recovered to normal after resolution of TMA with eculizumab therapy without need for plasma replacement.

Applicant's finding that eculizumab therapy could be successfully discontinued in responding patients indicates a unique mechanism of complement dysregulation in TMA after HSCT occurring in response to triggers like chemotherapy, infections, or GVHD in susceptible individuals. Without intending to be limited by theory, it appears that complement blockade is only required as a temporary measure to abort the TMA process after HSCT, and is not needed as life-long therapy, as currently recommended in aHUS and PNH.

Patients treated with eculizumab for high-risk TMA had much better outcomes than historically reported with this severe HSCT complication. Applicant found that the comparison of cases treated with eculizumab with prior consecutive cases diagnosed with high-risk TMA using identical criteria is un-randomized. However, the striking improvement in survival identified by Applicant supports future prospective studies of efficacy.

Due to variable drug clearance based on disease activity found by Applicant, eculizumab is a potential therapeutic option for HSCT recipients with complement-mediated TMA that benefits from personalized PK/PD guided dosing. Applicant found marked inter-individual variability in clearance of eculizumab, and also found that clinical events such as GI bleeding importantly changed clearance, indicating need for real-time dose adjustment to optimize complement blockade. Moreover, clearance of eculizumab slows as TMA resolves and real-time PK/PD monitoring can reduce the amount of therapy needed. Without intending to be limited by theory, Applicant hypothesizes that initiation of therapy early in the disease course will likely be cost-effective, as these patients should need less frequent dosing and shorter therapy with careful real-time PK/PD monitoring, and will likely avoid severe organ damage.

Patients should be carefully selected for therapy, with early treatment of those with a genetic predisposition to develop TMA after HSCT (Jodele et al, Blood. 2016 Feb. 25; 127(8):989-96. doi: 10.1182/blood-2015-08-663435. Epub 2015 Nov. 24) or severe phenotype, as defined in this study, and observation only for those with mild phenotypes Plasma sC5b-9 concentrations measured prior to therapy can guide eculizumab dosing in induction when prompt disease control is essential to avoid multi-organ injury. Even though HSCT recipients with TMA require frequent dosing initially, eculizumab dosing can be tapered using routine CH50 monitoring and discontinued safely after TMA is controlled resulting in improved long term outcomes.

Validation Data

Patient Demographics

A total of 52 eculizumab observations from 11 patients collected after the first induction dose were used to validate our pilot population pharmacokinetic (PK/PD) model. The patient demographics both for pilot and validation datasets are shown in Table 5.

TABLE 5

Patient demographics in pilot (n = 10) and validation dataset (n = 11)

| | Pilot dataset (n = 10)[*1] | | | Validation dataset (n = 11)[*2] | | |
|---|---|---|---|---|---|---|
| | Mean | SD | Range | Mean | SD | Range |
| Number of patients | 10 | | | 11 | | |
| Number of observations | 29 | | | 52 | | |
| Eculizumab induction dose 300 mg/600 mg/900 mg | 1/4/5 | | | 3/6/2 | | |
| Sex (Male/Female) | 6/4 | | | 8/3 | | |
| Body weight (kg) | 32.8 | 28.9 | 7-80 | 23.7 | 18.9 | 5.5-65 |
| Age (years) | 10 | 11.5 | 0.5-29.8 | 5.5 | 5.0 | 0.6-16 |
| Pre-treatment C5b-9 level (ng/mL) | 422 | 240 | 187-913 | 370 | 273 | 131-1035 |

Figure 11:
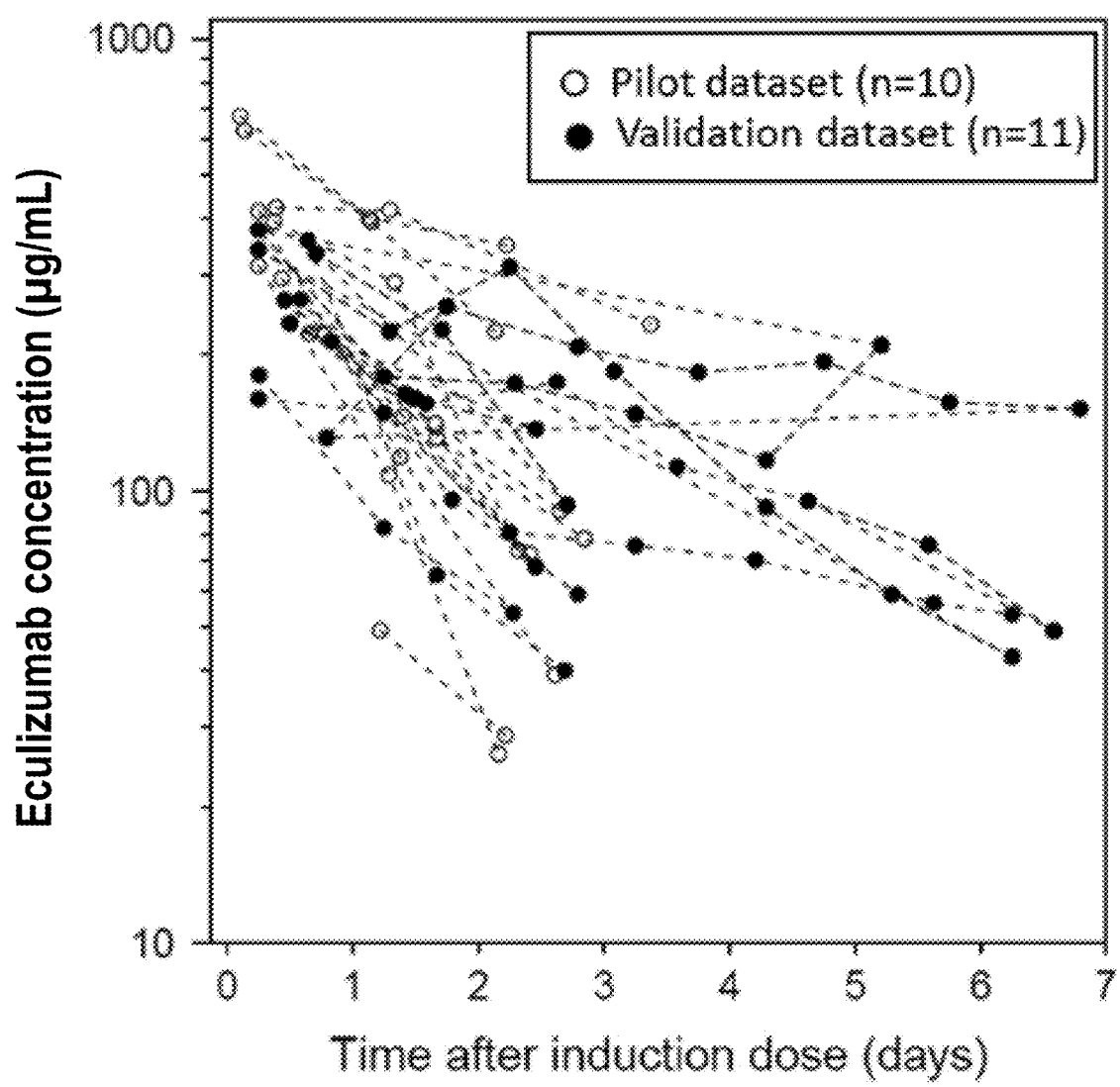
FIG. 11. Eculizumab pharmacokinetic profile after the first dose in pilot (n=10) and validation datasets (n=11), Eculizumab observations in each dataset were plotted over time after the first dose. The y-axis shows eculizumab concentrations and the x-axis shows time after the administration (days). Open circles represent the eculizumab concentrations in the pilot modeling dataset collected from 10 patients, and closed circles represent those in the validation dataset collected from 11 patients.

[*1]: Biol Blood Marrow Transplant 2016, 22(2):307-15
[*2]: Data sampled prospectively after the pilot model development 1-2. Eculizumab Pharmacokinetic Profiles The eculizumab concentration-time profiles from both datasets were visualized over time after the first dose (FIG. 11). The similar eculizumab PK profiles were observed up to 4 hours after the dose in the modeling and validation datasets. No observations were available in the modeling dataset beyond 4 hours after administration.

Figure 12:
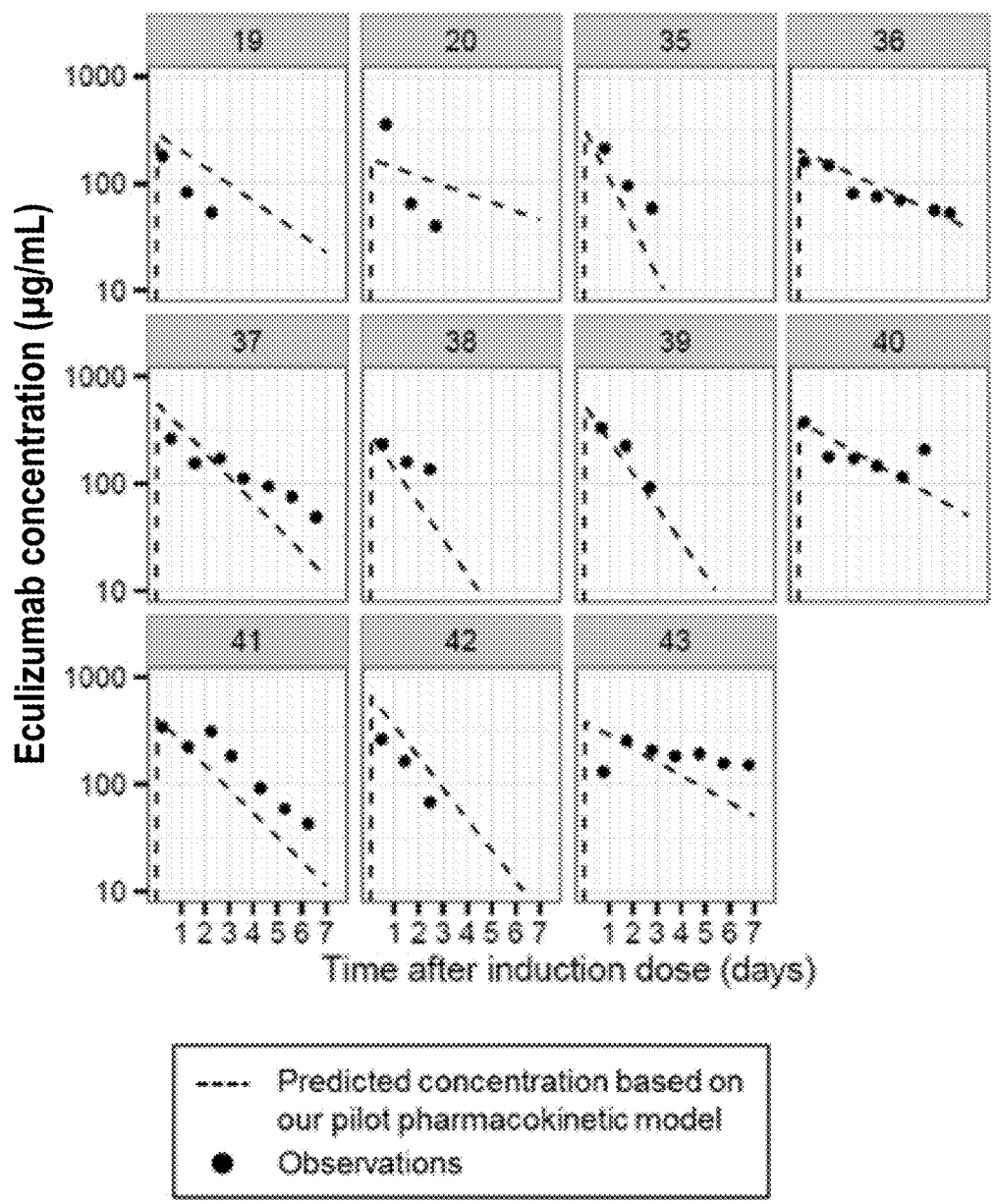
FIG. 12. Individual observations overlaid with pharmacokinetic model predicted profiles. Individual eculizumab pharmacokinetic profiles during induction therapy were predicted based on our pilot model, and were illustrated with actual observations. The y-axis shows eculizumab concentrations after the first dose and the x-axis shows time after the first dose administration (days). Closed circles represent eculizumab observations in validation dataset collected from 11 patients. Dashed lines represent predicted eculizumab pharmacokinetic profiles based on our pilot pharmacokinetic model with their body weight (WT) and pretreatment plasma soluble complement complex C5b-9 (pre-sC5b-9) as follows: CLi (mL/hr)=98.6·(WT/70)$^{0.75}$·(pre-sC5b-91422)$^{0.73}$; Vdi (L)=5.72·(WT/70)$^{1.0}$ where CLi is individual eculizumab clearance and Vdi is individual volume of distribution.
Figure 13:
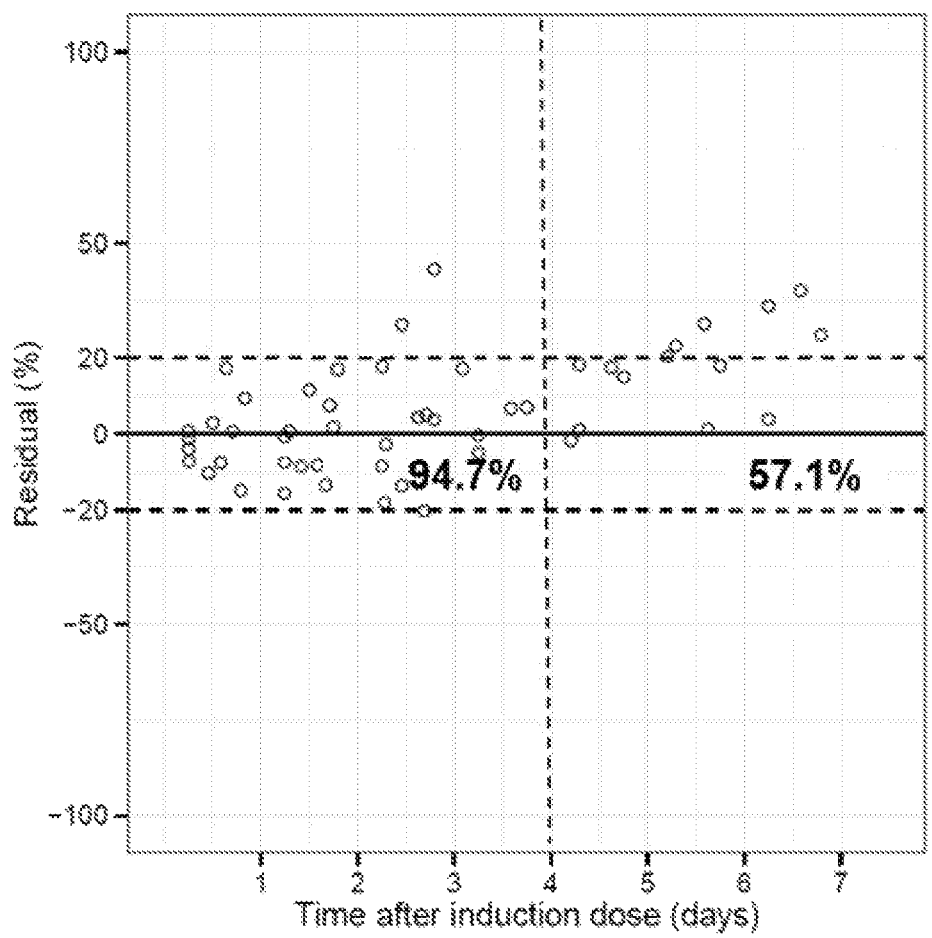
FIG. 13. Residual plot over time after induction dose. Residuals were calculated using the following equation: Residual (%)={Log(OBS)−Log(PRED)}/Log(PRED)×100, where OBS is observed eculizumab concentration, and PRED is model predicted concentration. 94.7% of observations between 0-4 days after the first dose showed less than 20% difference from the model predicted concentrations.
Figure 14A:
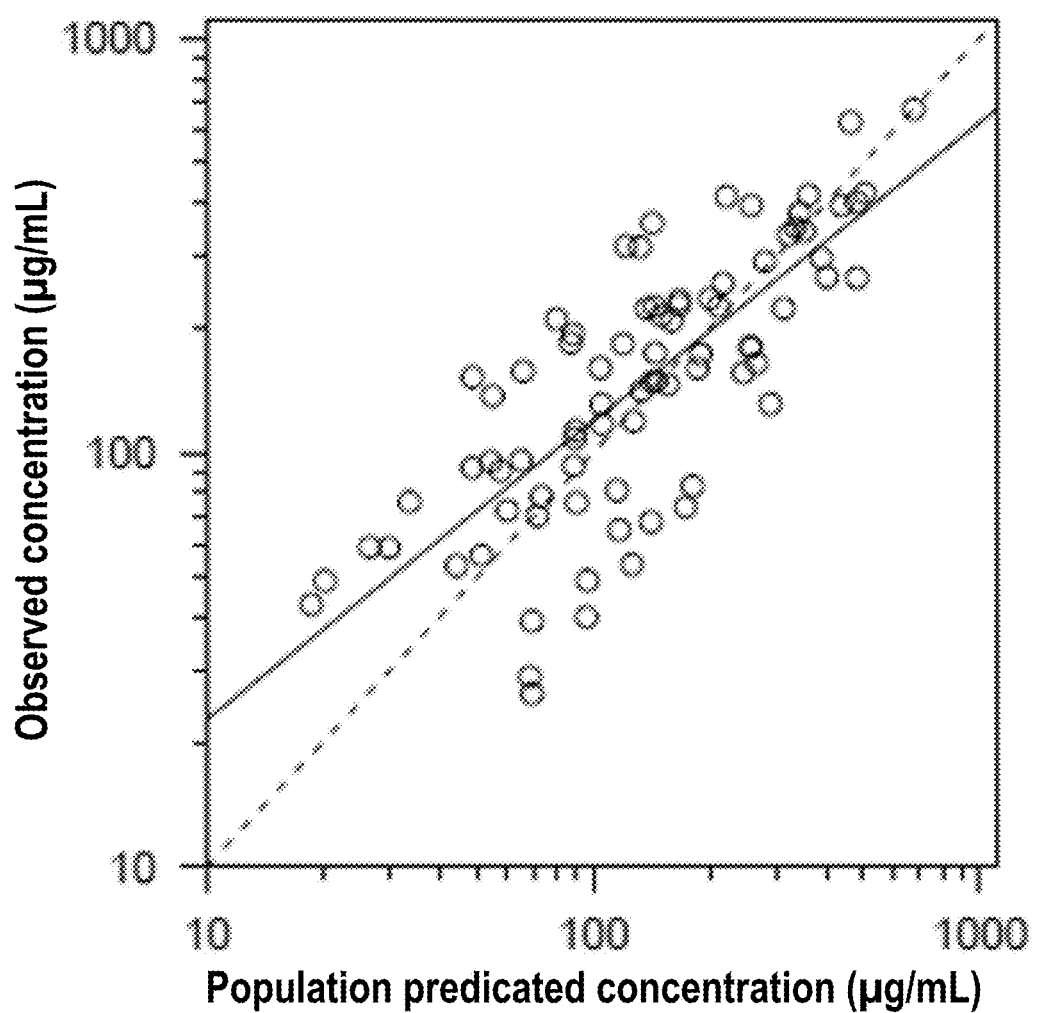
FIG. 14A-D. Goodness-of-fit plots in the final updated pharmacokinetic model (FIG. 14A). Observed versus population model predicted eculizumab concentrations.
Figure 14B:
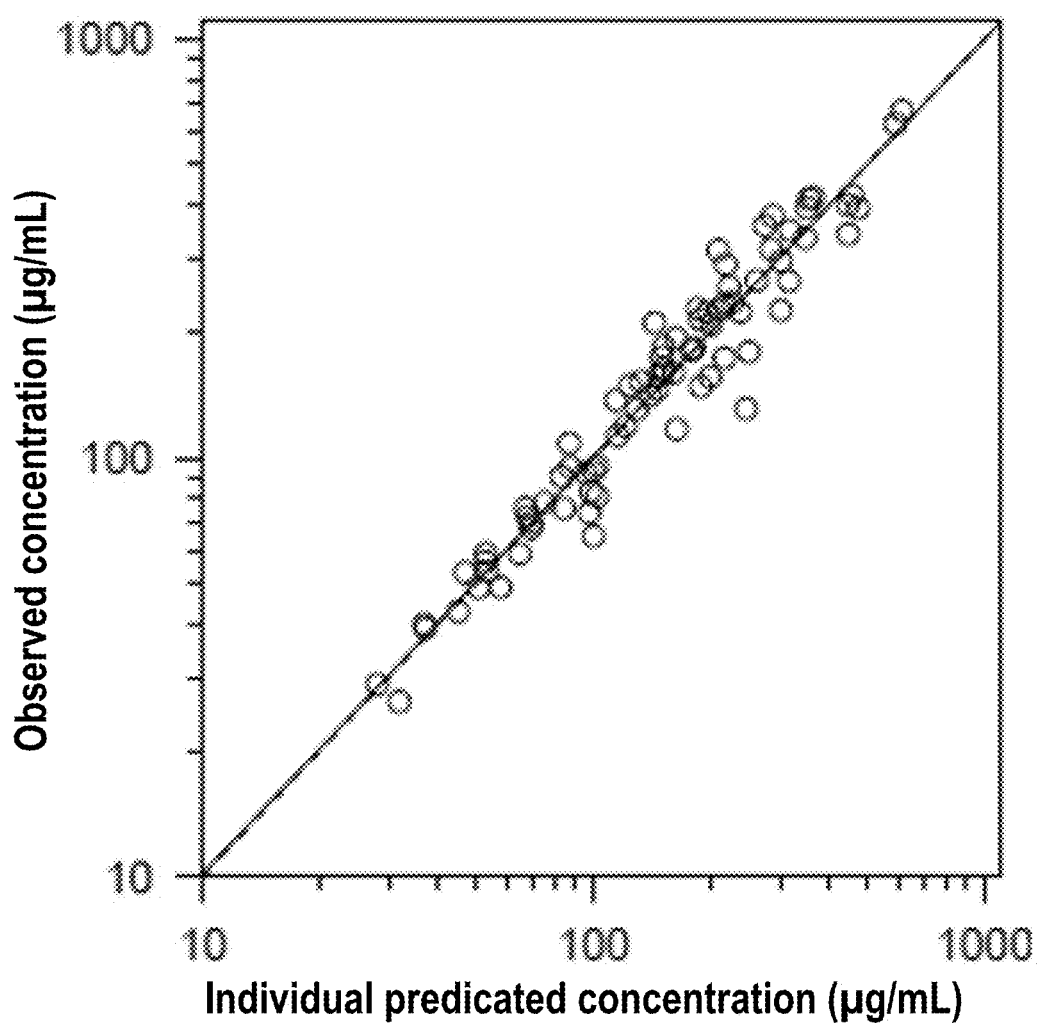
Figure 14C:
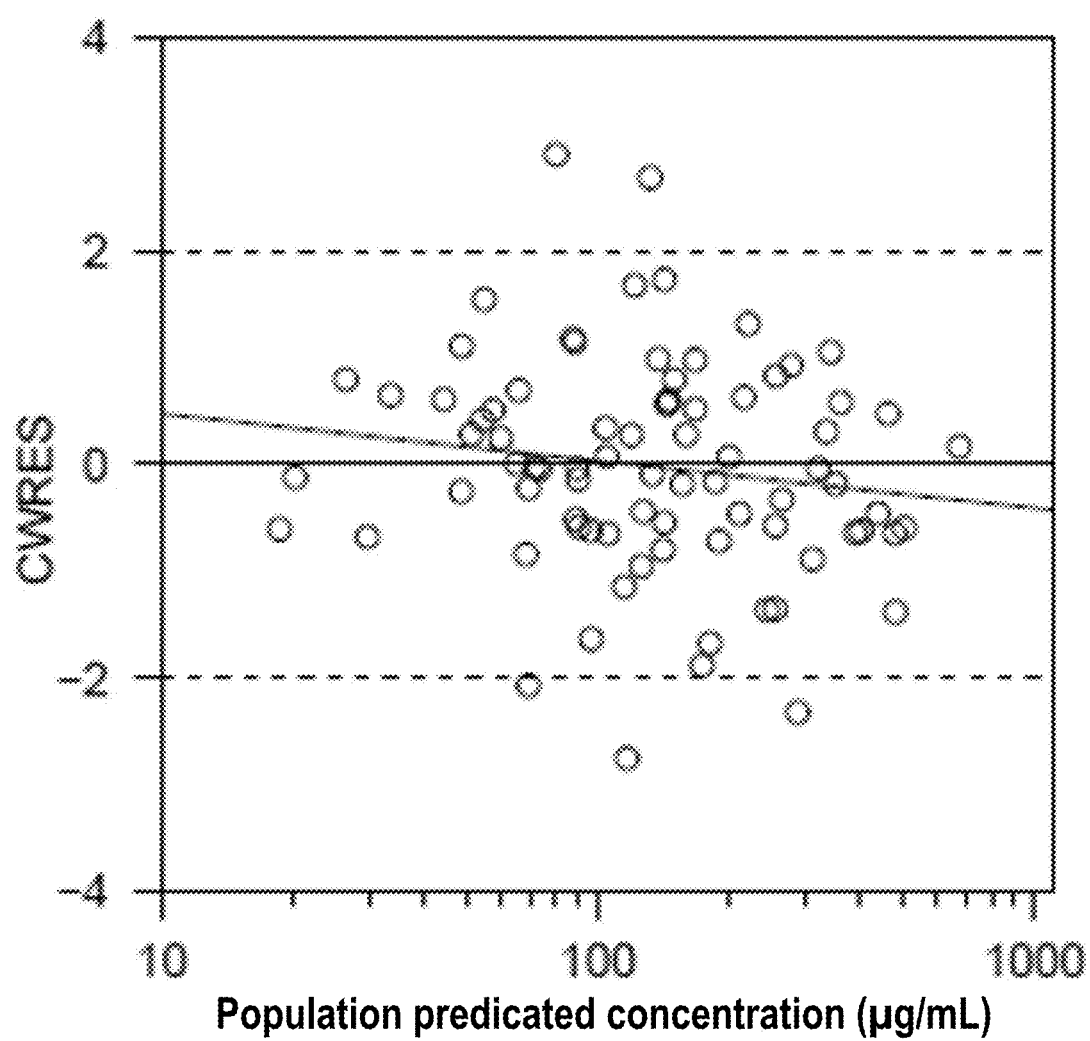
Figure 14D:
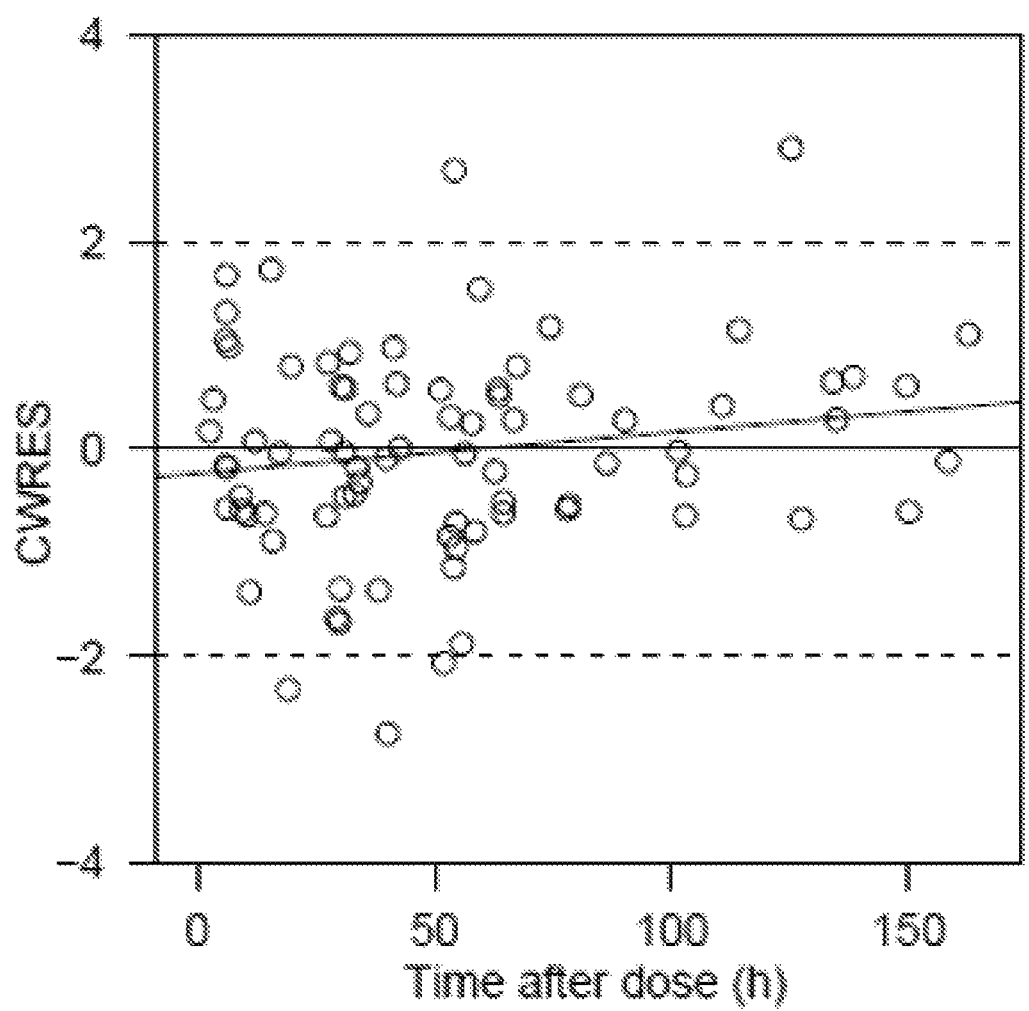

1-3. Model-Fit Plots for Eculizumab Concentrations in the Validation Dataset Fitted to Our Published Pilot Pharmacokinetic Model The precision and accuracy of our published model were evaluated using model-fit-plots in each patient (FIG. 12). The eculizumab concentration profiles were predicted based on our pilot population PK model with actual body weight (WT) and pretreatment soluble complement complex C5b-9 (pre-sC5b9). Importantly, residual plots over the time after the dose showed that 94.7% of observations between 0-4 days showed less than 20% difference from the model predicted concentrations (FIG. 13), suggesting that our pilot pharmacokinetic model was successfully validated with high predictive performance.

Population pharmacokinetic model update using combined pilot and validation dataset (n=21)

2-1 Patient Demographics

A total of 81 eculizumab observations after the induction dose collected from 21 patients were used to update the existing population PK model. The patient demographics both for published and combined datasets are shown in Table 6.

TABLE 6

Patient demographics in combined dataset (n = 21)

| | Combined dataset (n = 21) | | |
|---|---|---|---|
| | Mean | SD | Range |
| Number of patients | | | |
| Number of observations | 81 | | |
| Eculizumab induction dose 300 mg/600 mg/900 mg | 4/10/7 | | |
| Sex (Male/Female) | 14/7 | | |
| Body weight (kg) | 28.0 | 24.0 | 5.5-80 |
| Age (years) | 7.6 | 8.8 | 0.5-29.8 |
| Pre-treatment C5b-9 level (ng/mL) | 395 | 256 | 131-1035 |

2-2 Population PK Model Development

The population PK model was developed using the same method described in our published report (Biol Blood Marrow Transplant. 2016, 22(2):307-15). Final population PK parameter estimates in the previously publication and in this new analysis were shown in Table 7. The population PK parameter estimates generated from the combined dataset (n=21) were less than 15% difference from our previously published pilot model (CL; 7.7%, Vd; 5.7% and power for sC5b9; 14%).

TABLE 7

Final population PK parameter estimates

| Parameter | Pilot model (n = 10) Mean (% RSE) | Updated model (n = 21) Mean (% RSE) |
|---|---|---|
| Fixed effects | | |
| $CL_{pop}$ (mL/h/70 kg) | 98.6 (9%) | 91.0 (10%) |
| Exponent of allometry, for CL | Fixed to 0.75 | Fixed to 0.75 |
| $Vd_{pop}$ (L/70 kg) | 5.72 (21%) | 6.05 (12%) |
| Exponent of allometry for Vd | Fixed to 1.0 | Fixed to 1.0 |
| θC5b-9 | 0.73 (14%) | 0.628 (29%) |
| Inter-individual variability | | |
| $\omega_{CL}$ (% CV) | 20.3% (26%) | 46.5% (15%) |
| $\omega_{vd}$ (% CV) | 63.1% (21%) | 49.3% (20%) |

TABLE 7-continued

Final population PK parameter estimates

| Parameter | Pilot model (n = 10) Mean (% RSE) | Updated model (n = 21) Mean (% RSE) |
|---|---|---|
| Random residual variability | | |
| $\varepsilon_{prop}$ | 0.0329 (24%) | 0.0492 (12%) |
| Final model | | |

$$CL = CL_{pop} \times (WT/70)^{0.75} \times (\text{Pre-sC5b9/average pre-sC5b9})^{\theta C5b9}$$
$$Vd = Vd_{pop} \times (WT/70)^{1.0}$$

$CL_{pop}$: Population mean clearance (mL/h/70 kg),
$Vd_{pop}$: Population mean of the volume of distribution (L/70 kg) WT;
body weight (kg), pre-sC5b9;
Pretreatment soluble complement complex C5b-9. Average sC5b9 in the pilot and updated models were 422 and 395 (ng/mL), respectively.

2-3 Updated Population PK Model Evaluation

Figure 15:
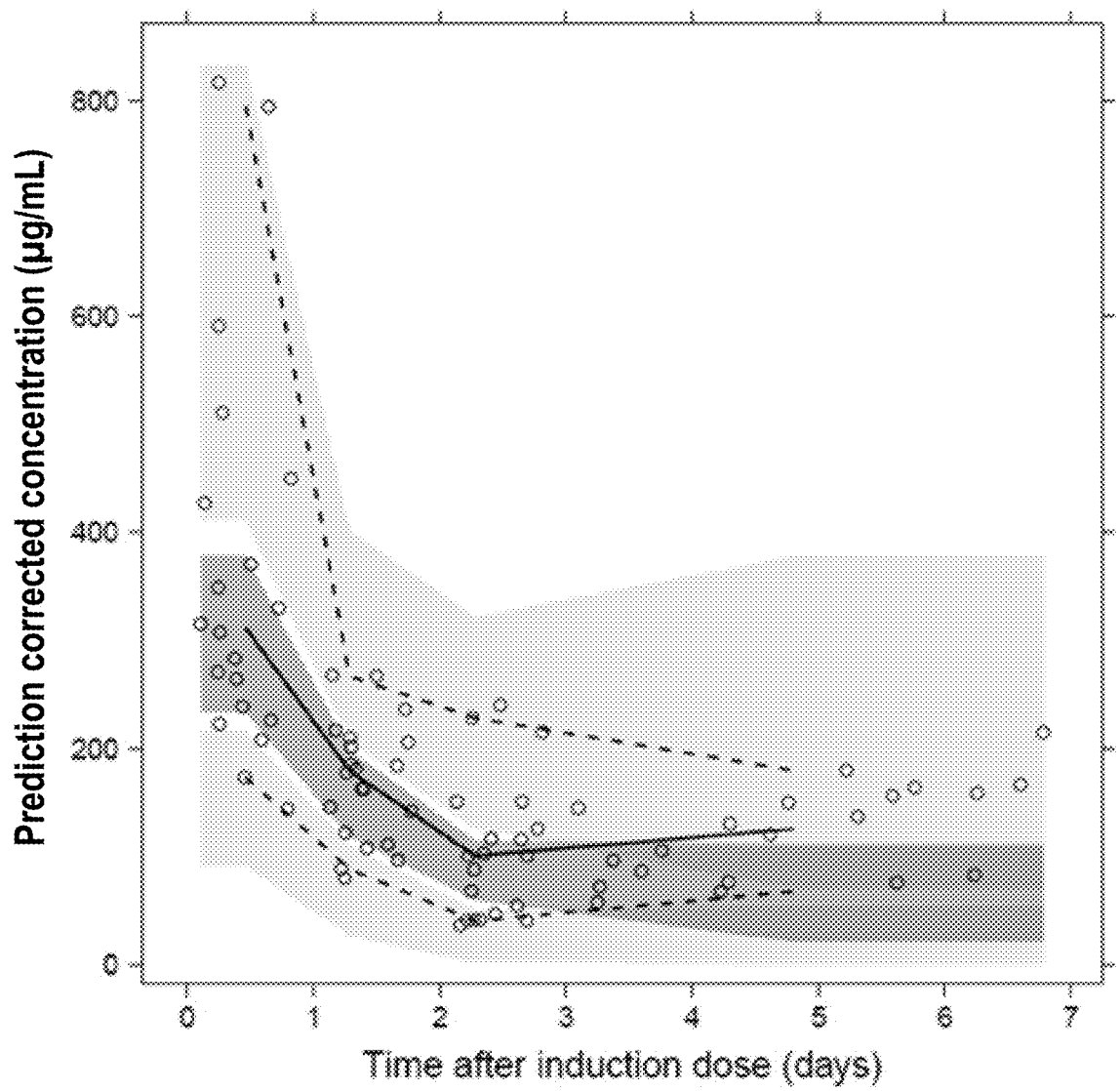
FIG. 15. Prediction corrected visual predictive check in the final updated model using 21 patients' dataset. Open circles represent prediction corrected-observed concentrations. Solid line represents the observed median value, and lower and upper dashed lines represent the observed 5th and 95th percentiles. Shaded areas indicate the confidence intervals of the 5th, 50th and 95th percentile of the simulated values.
Figure 16:
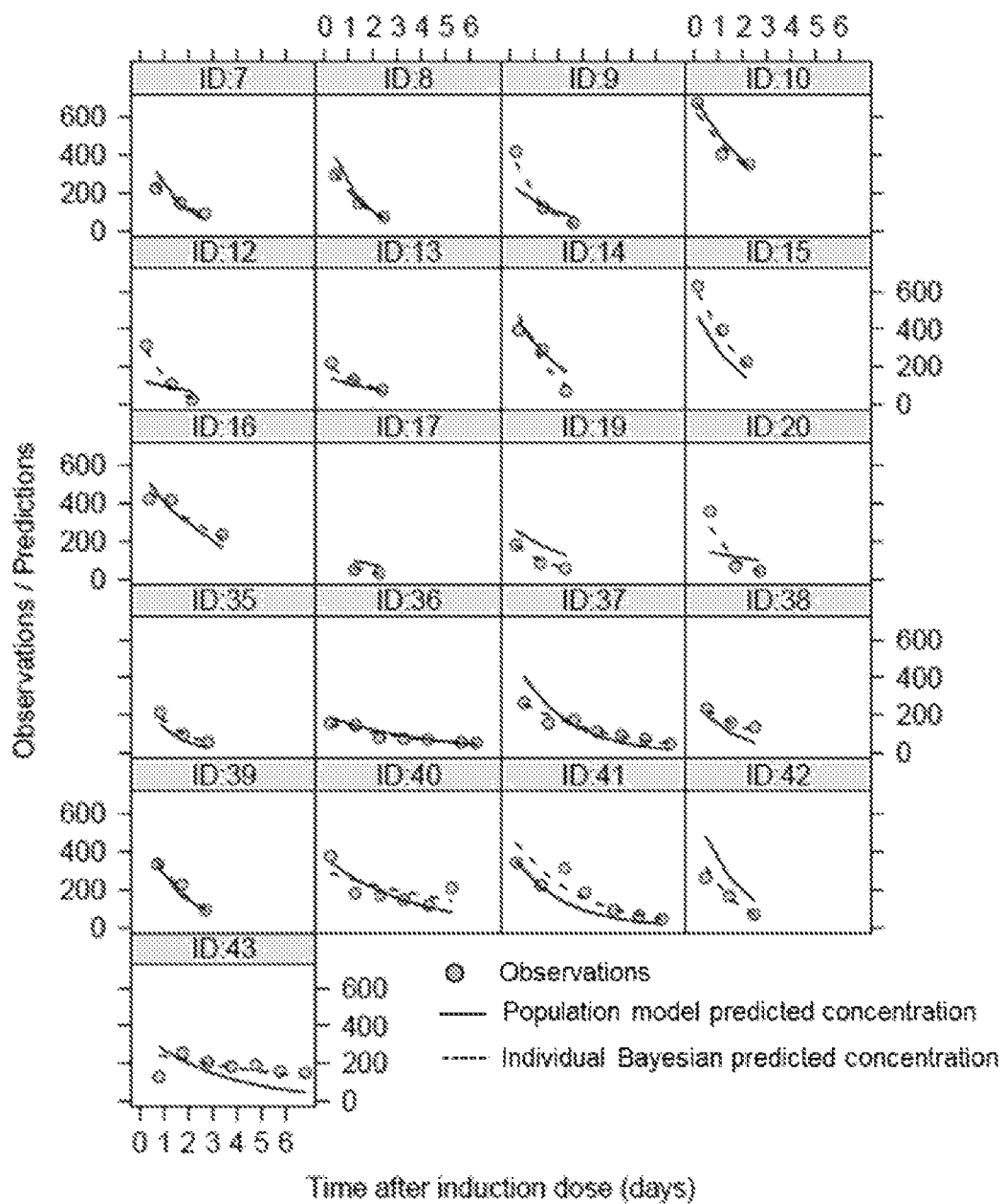
FIG. 16. Individual PK model-fit-plots after the first dose in 21 patients. The y-axis shows eculizumab observed, population model predicted or individual predicted concentrations after the first dose. The x-axis shows time after dose (days). Closed circles represent eculizumab observations collected from 21 patients. Solid lines represent predicted concentrations based on the updated population PK model. Dashed lines represent individual predicted concentrations by using a post-hos Bayesian estimation method. The population PK model used for these predictions are as follows: CLi (mL/hr)=91.0·(WT/70)$^{0.75}$·(pre-sC5b-9/395)$^{0.63}$; Vdi (L)=6.05·(WT/70)$^{1.0}$, where CLi is individual eculizumab clearance and Vdi is individual volume of distribution. Pre-sC5b-9 is pretreatment plasma complement complex soluble C5b-9 and WT is actual body weight.

The final model was evaluated by goodness-of-fit plots (FIG. 14), prediction corrected visual predictive check (FIG. 15) and individual model fit plots (FIG. 16). These figures show our updated model were unbiased.

2-3 PK Simulations

Based on the updated population PK model, PK profiles were simulated in various patients with different body weight and sC5b-9 levels. Initial doses were referred to current body weight-based dosing regimen. Table 8 summarizes time (how many hours) after the first dose when concentrations stayed above 100 μg/mL or 50 μg/mL. For clinical convenience, 24-hour interval was used as time indication. This example table can be used as a practical guidance/algorithm (behind of software) which guides clinicians to find the timing of the second dose.

TABLE 8

Time (hours) after the first dose: 50% of patients keep concentration above the Ctrough of 100 ug/mL (target) or 50 ug/mL

| Initial Dose (mg) | Body Weight (kg) | Time above 100 ug/mL > 50% of patients | | | |
|---|---|---|---|---|---|
| | | C5b-9 200 ng/mL | C5b-9 400 ng/mL | C5b-9 600 ng/mL | C5b-9 800 ng/mL |
| 300 | 3 | 96 | 72 | 48 | 24 |
| | 6 | 72 | 48 | 24 | 24 |
| | 9 | 72 | 48 | 24 | 24 |
| 600 | 10 | 96 | 72 | 48 | 48 |
| | 15 | 72 | 48 | 48 | 24 |
| | 20 | 72 | 48 | 24 | 24 |
| | 25 | 48 | 24 | 24 | 24 |
| | 30 | 48 | 24 | 24 | 24 |
| | 35 | 24 | 24 | <24 | <24 |
| 900 | 40 | 72 | 24 | 24 | 24 |
| | 45 | 48 | 24 | 24 | 24 |
| | 50 | 48 | 24 | 24 | <24 |
| | 55 | 48 | 24 | <24 | <24 |
| | 60 | 24 | 24 | <24 | <24 |
| | 65 | 24 | 24 | <24 | <24 |
| | 70 | 24 | <24 | <24 | <24 |
| | 75 | 24 | <24 | <24 | <24 |
| | 80 | <24 | <24 | <24 | <24 |
| 300 | 3 | 144 | 72 | 72 | 48 |
| | 6 | 120 | 72 | 48 | 48 |
| | 9 | 96 | 72 | 48 | 48 |
| 600 | 10 | 144 | 96 | 72 | 72 |
| | 15 | 120 | 72 | 72 | 48 |
| | 20 | 120 | 72 | 48 | 48 |
| | 25 | 120 | 72 | 48 | 48 |
| | 30 | 96 | 72 | 48 | 48 |
| | 35 | 96 | 48 | 48 | 24 |
| 900 | 40 | 120 | 72 | 48 | 48 |
| | 45 | 120 | 72 | 48 | 48 |
| | 50 | 96 | 72 | 48 | 48 |
| | 55 | 96 | 72 | 48 | 48 |
| | 60 | 96 | 48 | 48 | 24 |
| | 65 | 96 | 48 | 48 | 24 |
| | 70 | 72 | 48 | 48 | 24 |
| | 75 | 72 | 48 | 24 | 24 |
| | 80 | 72 | 48 | 24 | 24 |

Example—SC5b-9 Assay

The MicroView™ SC5b-9 Plus ELISA (available from quidel.com) is for the quantitation of Terminal Complement Complex, SC5b-9, in human plasma. This is a three-step procedure using (1) a microassay plate coated with a mouse monoclonal antibody that binds specifically to the C9 ring of SC5b-9, (2) HRP-conjugated antibodies to antigens of SC5b-9, and (3) a chromogenic substrate. In the first step, standards, controls, and test specimens are added to microassay wells precoated with an anti-SC5b-9 specific monoclonal antibody. SC5b-9 present in the standards, controls, or specimens will bind to the immobilized anti-SC5b-9. After incubation, a wash cycle removes unbound material.

Constituent proteins of the TCC, including C9, do not bind to this antibody and are washed away during the wash cycle. In the second step, horseradish peroxidase (HRP)-conjugated antibodies to antigens on SC5b-9 are added to each test well. The enzyme-conjugated antibodies bind to SC5b-9 that was captured by the monoclonal anti-SC5b-9 bound on the surface of the microassay wells. After incubation, a wash cycle removes unbound conjugate.

In the third step, a chromogenic enzyme substrate is added to each microassay well.

The bound HRP-conjugate reacts with the substrate forming a blue color. After incubation, an $H_2SO_4$ reagent is added to stop color development, resulting in a yellow color. The standard, control, and test specimen absorbances (A450 values) are measured spectrophotometrically. The color intensity of the reaction mixture is proportional to the concentration of SC5b-9 (TCC) present in the test specimens, standards, and controls. The SC5b-9 assay measures the concentration of TCC, thereby giving an indication of the status of the terminal complement pathway in the specimen.

Specimen Collection

Patient Preparation:

No special preparation is required.

Specimen Type:

EDTA plasma. Specimens should be collected aseptically using standard techniques, spun, and plasma removed from cells within 2 hours of collection.

Storage Conditions:

Plasma sample must be tested within 4 hours of collection or frozen at <−70° C. for future testing.

Equipment and Materials
Reagents
MicroVue_SC5b-9 Plus kit (Quidel, Catalog #A020) Store at 2-8° C.
  Supplies
  Nunc-Immuno_Module-clear, Individual strips of 8 wells each (Nunc MaxiSorp #469949)
  Well strip holder plate
  Wash bottle and 8 channel washing system
  Single and multichannel pipettes and tips
  Deionized water
  Timer
  Instrumentation
  BioTek Epoch plate reader
  Lab Line Titer Plate Shaker
Preparation of Reagents
MicroVue SC5b-9 Plus kit:
  20× wash solution—dilute contents of bottle up to 1 liter with deionized water. Stable for 30 days at 2-8° C. If the 20× Wash Solution Concentrate has been stored at 2-8° C., crystals may have formed. To dissolve the crystals, warm the bottle in a 37-50° C. water bath until all crystals have dissolved, and follow by mixing thoroughly.
  Standards A-E. Serum standards, diluted and ready to use. Store at 2-8° C.
  High and Low Controls. Diluted and ready to use. Store at 2-8° C.
  SC5b-9 Plus Conjugate. Ready to use. Store at 2-8° C.
  Substrate Solution. Ready to use. Store at 2-8° C.
  Stop Solution. 2M $H_2SO_4$ Ready to use. Store at 2-8° C.
Performance Parameters
  1. All reagents and kit components must be used before the expiration date stated on the package insert.
  2. If the plate reader or any essential equipment that is necessary for this assay become inoperable, the requesting physician will be notified and the test will be either sent out to another lab for testing or stored for future testing once the equipment is returned to working order.
Storage Requirements
  All reagents should be stored in the original containers at the temperatures stated under preparation of reagents.
Calibration
  1. The plate reader must be calibrated prior to each use.
  2. Standard curve is run with each assay. Plot the absorbance against the concentrations of the SC5b-9 standards using a
    Linear regression curve.
  3. The standard curve must have a correlation coefficient (r): >0.950 or the run must be repeated and/or the procedure should undergo troubleshooting.
Quality Control
  High and low plasma control with known amounts of SC5b-9. Ranges for the controls will be included with each vial and both the high and low control sample results must fall within the published ranges. If both controls do not fall within the 2SD range, one must fall within 2SD and the other within 3SD for the run to be reported. If controls fail, the run should undergo troubleshooting and be repeated.
  Standards A-E containing known amounts of SC5b-9. Concentrations vary slightly from lot to lot and values must be changed on the plate reader template prior to reading the samples. Check each new lot for new ranges.
Procedure
  1. Allow kit components to come to room temperature.
  2. Thaw frozen plasma samples in a 37° C. water bath for 4 minutes and immediately place and maintain on ice.
  3. Record the microassay well positions corresponding to the blank well(s), Standards, and Controls, all test samples, as well as the indicated lot numbers from the vial labels on plate template form.
  4. Assemble and label microassay plate for orientation with only as many strips as needed for number of tests.
  5. Prepare the microassay strips as follows:
    a. Rehydrate microassay wells by adding approximately 300 µL of Wash Solution to each well using a wash bottle or automated filling device.
    b. Incubate at 15-30° C. for two minutes.
    c. Remove/decant the liquid from each well.
    d. Invert the plate and tap firmly on absorbent paper to remove any remaining liquid.
  6. To load the Standards, Controls and diluted specimens into the microassay wells as rapidly as possible, a "replica plating" procedure will be employed.
  Dilute plasma samples 1:10 (30 uL plasma and 270 uL specimen diluent) in uncoated, dilution plate well strips so the order matches the assay plate format with one strip for each duplicate column of assay plate. Dilutions can be made in directly in uncoated wells, or in test tubes and transferred to uncoated wells. Mix thoroughly with pipette before transfer to reagent coated assay plate.
  7. Place 300 uL Sample Diluent for blank, each RTU standard (A-E) and both RTU controls in uncoated, dilution plate well strips so the order matches the assay plate format with one strip for each duplicate column of assay plate.
  8. After all the solutions to be tested have been added to the wells in the uncoated, dilution plate well strips, rapidly transfer 100 µL from the uncoated dilution plate wells to the antibody-coated assay wells, using a multichannel micropipettor, following the template below. Pipette each sample into duplicate columns Discard dilution plate well strips after transfer.

| row 1/2 | row 3/4 | row 5/6 | row 7/8 | row 9/10 | row 11/12 |
|---|---|---|---|---|---|
| ① Blank | ① Pt 1 | ① Pt 9 | ① Pt 17 | ① Pt 25 | ① Pt 33 |
| ② Std A | ② Pt 2 | ② Pt 10 | ② Pt 18 | ② Pt 26 | ② Pt 34 |
| ③ Std B | ③ Pt 3 | ③ Pt 11 | ③ Pt 19 | ③ Pt 27 | ③ Pt 35 |
| ④ Std C | ④ Pt 4 | ④ Pt 12 | ④ Pt 20 | ④ Pt 28 | ④ Pt 36 |
| ⑤ Std D | ⑤ Pt 5 | ⑤ Pt 13 | ⑤ Pt 21 | ⑤ Pt 29 | ⑤ Pt 37 |
| ⑥ Std E | ⑥ Pt 6 | ⑥ Pt 14 | ⑥ Pt 22 | ⑥ Pt 30 | ⑥ Pt 38 |
| ⑦ High Cont | ⑦ Pt 7 | ⑦ Pt 15 | ⑦ Pt 23 | ⑦ Pt 31 | ⑦ Pt 39 |
| ⑧ Low Cont | ⑧ Pt 8 | ⑧ Pt 16 | ⑧ Pt 24 | ⑧ Pt 32 | ⑧ Pt 40 |

9. Incubate at 15-30° C. for 60 (+1) minutes.
  10. Wash the microassay wells as follows:
    a. After the incubation remove/decant the liquid from each well.
    b. Add approximately 300 µL Wash Solution to each well using a wash bottle or automated filling device.
    c. Incubate the wells for 1 minute at 15-30° C.
    d. Remove/decant the liquid from each well. Tap on absorbent paper.
    e. Add approximately 300 µL Wash Solution to each well.
    f. Remove the liquid from each well.
    g. Repeat steps e-f three additional times.
    h. After the fifth wash cycle, invert the plate, and tap firmly on absorbent paper to remove any remaining liquid.
  11. Using a multichannel or repeating pipette, dispense 50 µL of SC5b-9 Plus Conjugate into each washed test well, including the blank well(s).
  12. Incubate the microassay strips at 15-30° C. for 30 (±1) minutes.

13. Wash the microassay wells after the 30-minute incubation as in step 9.

14. Immediately following the wash procedure, dispense 100 µL of the Substrate Solution into each well, including the blank(s).

15. Incubate the microassay strips at 15-30° C. for 15 (±1) minutes.

16. Add 100 µL of Stop Solution to each well to stop the enzymatic reaction. The Stop Solution should be added to the wells in the same order and at the same rate as the Substrate Solution. Gently tap the plate to disperse the color development evenly. NOTE: Optimal results may be obtained by using the plate reader's auto-mix function just prior to reading the plate.

17. Determine the absorbance reading at 450 nm (A450 value) for each test well within 30 minutes after the addition of the Stop Solution. (SC 58)

18. The results of the normal control, the abnormal control and the patient plasmas are determined by interpolation from the linear regression curve.

Calculations

The standard curve for the SC5b-9 Plus EIA is generated using the blank subtracted A450 values for each standard (on the y axis) and the assigned concentration for each standard (on the x axis). The assigned concentration on the standard vials and the control vials are absolute units of SC5b-9 complex. The concentration of SC5b-9 in a specimen is determined by multiplying the determined concentration by the appropriate specimen dilution factor. Example: If a plasma sample is diluted 1:10 for the assay and the linear regression curve yields a concentration of 20 ng/mL, then the concentration of SC5b-9 in the specimen would be 200 ng SC5b-9/mL or (20×10). In order to obtain accurate SC5b-9 concentration determinations for test specimens that yield A450 values greater than that of the SC5b-9 Standard E (or that yield A450 values less than the LLOQ), specimens should be re-assayed at a different dilution so that their new A450 values will be within these limits. In all repeat assays the SC5b-9 standards and controls must also be retested.

Reporting Results

Reference Interval

A reference interval is determined by evaluating SC5b-9 on in-house normal donor plasmas and through literature review of other laboratories running this assay.

Normal ranges:
Male: 72-244 ng/mL
Female: 27-244 ng/mL

Procedures for Reporting Abnormal Results

Results are reported with normal reference intervals. There are no critical values for this assay.

Procedure Notes and Precautions

1. Samples must be diluted so that A450 values observed are above the LLOQ and do not exceed the A450 value of the SC5b9 Kit Plus Standard E. Samples with A450 readings outside this range should be re-assayed at a new dilution.

2. Quidel suggests that serum samples should be diluted 1:40. A 1:200 dilution, or greater, may be required for a sample with high levels of SC5b-9.

3. Do not allow microassay wells to dry once the assay has begun.

4. Thaw frozen specimens rapidly at 37° C. until just thawed. Transfer thawed specimens immediately to ice (for no longer than four hours) to prevent complement activation prior to dilution. Do not leave specimens at 37° C., as complement activation may occur. Do not thaw specimens at room temperature or 4° C. as this can lead to complement activation. Specimens should be tested as soon as possible after thawing.

5. Repeated freezing and thawing is not recommended. If samples are to be refrozen for further analysis, Quidel suggests freezing multiple aliquots of the specimen to prevent multiple freeze/thaw cycles.

6. Treat specimen samples as potentially bio-hazardous material. Follow universal precautions when handling samples.

7. Discard samples, containers, and unused reagents in accordance with Federal, state, and local regulations.

8. Wear gloves and eyewear when handling samples and the chemical components of the kit.

9. Avoid cross-contamination of specimens or reagents.

10. The TMB substrate must be protected from light during storage and incubation.

11. When removing liquid from wells do not scrape or touch the bottom of the wells.

12. In rare necessary situations, citrated samples may be accepted. Results will be reported to include a notation that normal ranges are set on EDTA samples.

Analytical Measurement Range

Limit of detection is 3.7 ng/mL. The lower limit of quantitation is 8.8 ng/mL, the lowest concentration on the standard curve that meets NCCLS criteria for accuracy and precision.

Limitations of the Procedure

The reference ranges of the assay have only been validated for plasma samples from EDTA tubes.

Interfering Substances

Heat-inactivated specimens may yield erroneous results.

Hyperlipemic or contaminated specimens may give erroneous results.

REFERENCES

1. Jodele S, Laskin B L, Dandoy C E, et al. A new paradigm: Diagnosis and management of HSCT-associated thrombotic microangiopathy as multi-system endothelial injury. Blood reviews 2015. May; 29(3):191-204
2. de Fontbrune F S, Galambrun C, Sirvent A, et al. Use of Eculizumab in Patients With Allogeneic Stem Cell Transplant-Associated Thrombotic Microangiopathy: A Study From the SFGM-TC. Transplantation 2015. September; 99(9):1953-9
3. Kim S S, Patel M, Yum K, Keyzner A. Hematopoietic stem cell transplant-associated thrombotic microangiopathy: review of pharmacologic treatment options. Transfusion 2015; 55:452-8.
4. Labrador J, Lopez-Corral L, Lopez-Godino O, et al. Risk factors for thrombotic microangiopathy in allogeneic hematopoietic stem cell recipients receiving GVHD prophylaxis with tacrolimus plus MTX or sirolimus. Bone Marrow Transplant 2014:May; 49(5):684-90.
5. Cho B S, Yahng S A, Lee S E, et al. Validation of recently proposed consensus criteria for thrombotic microangiopathy after allogeneic hematopoietic stem-cell transplantation. Transplantation 2010; 90:918-26.
6. Jodele S, Davies S M, Lane A, et al. Refined diagnostic and risk criteria for HSCT-associated thrombotic microangiopathy: a prospective study in children and young adults. Blood 2014, 124(4):645-653.
7. Laskin B L, Maisel J, Goebel J, et al. Renal Arteriolar C4d Deposition: A Novel Characteristic of Hematopoietic Stem Cell Transplantation-Associated Thrombotic Microangiopathy. Transplantation 2013:Jul. 27; 96(2): 217-23.
8. Jodele S, Licht C, Goebel J, et al. Abnormalities in the alternative pathway of complement in children with hematopoietic stem cell transplant-associated thrombotic microangiopathy. Blood 2013; 122:2003-7.
9. Ricklin D, Cines D B. TMA: beware of complements. Blood 2013; 122:1997-9.
10. Ricklin D, Lambris J D. Complement in immune and inflammatory disorders: pathophysiological mechanisms. J Immunol 2013; 190:3831-8.
11. Meri S. Complement activation in diseases presenting with thrombotic microangiopathy. European Journal of Internal Medicine 2013; 24:496-502.
12. Kojouri K, George J N. Thrombotic microangiopathy following allogeneic hematopoietic stem cell transplantation. Curr Opin Oncol 2007; 19:148-54.
13. Nakamae H, Yamane T, Hasegawa T, et al. Risk factor analysis for thrombotic microangiopathy after reduced-intensity or myeloablative allogeneic hematopoietic stem cell transplantation. American journal of hematology 2006; 81:525-31.
14. Willems E, Baron F, Seidel L, Frere P, Fillet G, Beguin Y. Comparison of thrombotic microangiopathy after allogeneic hematopoietic cell transplantation with high-dose or nomyeloablative conditioning. Bone Marrow Transplant 2010; 45:689-93.
15. Uderzo C, Bonanomi S, Busca A, et al. Risk factors and severe outcome in thrombotic microangiopathy after allogeneic hematopoietic stem cell transplantation. Transplantation 2006; 82:638-44.
16. Jodele S, Davies S M, Lane A, et al. Diagnostic and risk criteria for HSCT-associated thrombotic microangiopathy: a study in children and young adults. Blood 2014; 124:645-53.
17. Jodele S, Fukuda T, Vinks A, et al. Eculizumab Therapy in Children with Severe Hematopoietic Stem Cell Transplantation-Associated Thrombotic Microangiopathy. Biol Blood Marrow Transplant 2014:April; 20(4):518-25.
18. Schmidtko J, Peine S, El-Housseini Y, Pascual M, Meier P. Treatment of atypical hemolytic uremic syndrome and thrombotic microangiopathies: a focus on eculizumab. Am J Kidney Dis 2013; 61:289-99.
19. Shah N, Rutherford C, Matevosyan K, Shen Y M, Sarode R. Role of ADAMTS13 in the management of thrombotic microangiopathies including thrombotic thrombocytopenic purpura (TTP). Br J Haematol 2013; 163:514-9.
20. Legendre C M, Licht C, Muus P, et al. Terminal complement inhibitor eculizumab in atypical hemolytic-uremic syndrome. N Engl J Med 2013; 368:2169-81.
21. Legendre C M, Licht C, Loirat C. Eculizumab in atypical hemolytic-uremic syndrome. N Engl J Med 2013; 369: 1379-80.
22. Jodele S, Fukuda T, Vinks A, et al. Eculizumab Therapy in Children with Severe Hematopoietic Stem Cell Transplantation-Associated Thrombotic Microangiopathy. Biology of blood and marrow transplantation: journal of the American Society for Blood and Marrow Transplantation 2014 April; 20(4):518-25.
23. Peffault de Latour R, Fremeaux-Bacchi V, Porcher R, et al. Assessing complement blockade in patients with paroxysmal nocturnal hemoglobinuria receiving eculizumab Blood 2015; 125:775-83.
24. Prasad K, Karlupia N. Prevention of bacterial meningitis: an overview of Cochrane systematic reviews. Respiratory medicine 2007; 101:2037-43.
25. Youden W J. Index for rating diagnostic tests. Cancer 1950; 3:32-5.
26. Zheng S, Gaitonde P, Andrew M A, Gibbs M A, Lesko L J, Schmidt S. Model-based assessment of dosing strategies in children for monoclonal antibodies exhibiting target-mediated drug disposition. CPT: pharmacometrics & systems pharmacology 2014; 3:e138.
27. Anderson B J, Holford N H. Tips and traps analyzing pediatric P K data.
Paediatric anaesthesia 2011; 21:222-37.
28. Keating G M. Eculizumab a review of its use in atypical haemolytic uraemic syndrome. Drugs 2013; 73:2053-66.
29. McKeage K. Eculizumab: a review of its use in paroxysmal nocturnal haemoglobinuria. Drugs 2011; 71:2327-45.
30. van den Born B J, van der Hoeven N V, Groot E, et al. Association between thrombotic microangiopathy and reduced ADAMTS13 activity in malignant hypertension. Hypertension 2008; 51:862-6.
31. Feng S, Eyler S J, Zhang Y, et al. Partial ADAMTS13 deficiency in atypical hemolytic uremic syndrome. Blood 2013; 122:1487-93.
32. Shayani S, Palmer J, Stiller T, et al. Thrombotic microangiopathy associated with sirolimus level after allogeneic hematopoietic cell transplantation with tacrolimus/sirolimus-based graft-versus-host disease prophylaxis. Biol Blood Marrow Transplant 2013; 19:298-304.
33. Rachakonda S P, Penack O, Dietrich S, et al. Single-Nucleotide Polymorphisms Within the Thrombomodulin Gene (THBD) Predict Mortality in Patients With Graft-Versus-Host Disease. J Clin Oncol 2014; 32:3421-7.
34. Dietrich S, Falk C S, Benner A, et al. Endothelial vulnerability and endothelial damage are associated with risk of graft-versus-host disease and response to steroid treatment. Biol Blood Marrow Transplant 2013; 19:22-7.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating thrombotic microangiopathy (TMA) in an individual having undergone hematopoietic stem cell transplant (HSCT), comprising:
   a) determining a pretreatment plasma complement complex soluble C5b-9 level (pre-sC5b-9), in units of ng/mL, in said individual prior to administration of an initial eculizumab dose (Dose);
   b) administering an initial dose of eculizumab to said individual;
   c) determining a body weight (WT), in units of kilograms, of said individual;
   d) determining systemic clearance of eculizumab (CL) and volume of distribution (Vd) in said individual, wherein CL (systemic clearance of eculizumab, in units of mL/h)=$98.6*(WT/70)^{0.75}*(pre-sC5b-9/422)^{0.73}$ and Vd (volume of distribution, in units of L)=$5.72*(WT/70)^{1}$,
   e) visualizing a plot of predicted eculizumab plasma concentration (Cp) versus time (t) in said individual, wherein Cp (plasma concentration of eculizumab (µg/ml) in said individual)=$(Dose/Vd)*e^{-(CL/Vd)*t}$ and e=a mathematical constant, approximately equal to 2.71828;
   f) determining a time (t) when said eculizumab plasma concentration will decline below a therapeutic level of 100 µg of eculizumab per mL of plasma in said individual based on said plot of predicted eculizumab plasma concentration versus time; and
   g) administering an eculizumab dose subsequent to said initial eculizumab dose to said individual at the determined time (t) in step (f).

2. The method of claim 1, further comprising displaying said plot of predicted eculizumab plasma concentration (Cp) versus time (t) on a device designed to display said plot.

3. The method of claim 2, said device being a handheld device.

* * * * *